(12) United States Patent
Nakanishi et al.

(10) Patent No.: US 7,544,478 B2
(45) Date of Patent: Jun. 9, 2009

(54) METHOD FOR SCREENING FOR COMPOUNDS THAT MODULATE P16 MEDIATED REGULATION OF NMDA RECEPTORS

(75) Inventors: Nobuki Nakanishi, Solana Beach, CA (US); Gang Tong, San Diego, CA (US); Shichun Tu, San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 558 days.

(21) Appl. No.: 10/914,669

(22) Filed: Aug. 9, 2004

(65) Prior Publication Data

US 2005/0037433 A1 Feb. 17, 2005

Related U.S. Application Data

(60) Provisional application No. 60/494,017, filed on Aug. 8, 2003.

(51) Int. Cl.
*G01N 33/567* (2006.01)
*C12N 5/22* (2006.01)

(52) U.S. Cl. .................. 435/7.21; 435/368; 435/375
(58) Field of Classification Search ............... None
See application file for complete search history.

(56) References Cited

U.S. PATENT DOCUMENTS 4,904,681 A 2/1990 Cordi et al.
5,061,721 A 10/1991 Cordi et al.
5,086,072 A 2/1992 Trullas et al.

OTHER PUBLICATIONS

Bourdelles et al, 1994. J Neurochem. 62(6): 2091-2098; abstract only.*
Sasaki et al, 2001. J Neurophysiol. 87: 2052-2063.*
Wang et al. (Nuc. Acids Res. 27: 4609-4618, 1999; p. 4617).*
Kaufman et al (Blood 94: 3178-3184, 1999).*
Wells (Sep. 18, 1990) Biochemistry 29(37): 8509-8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Bork (2000) Genome Research 10:398.*
Skolnick and Fetrow (2000) Trends in Biotech. 18(1): 34.*
Doerks et al. (Jun. 1998) Trends in Genetics 14(6): 248.*
Smith and Zhang (Nov. 1997) Nature Biotechnology 15:1222.*
Brenner (Apr. 1999) Trends in Genetics 15(4): 132.*

(Continued)

*Primary Examiner*—Elizabeth C. Kemmerer
*Assistant Examiner*—Zachary C Howard
(74) *Attorney, Agent, or Firm*—David M. Kohn; Catalyst Law Group, APC

(57) ABSTRACT

Discovered is a novel protein and variants thereof whose activity at the NMDA receptor causes an increased efflux of calcium ions through the channel of said receptor. This activity is downregulated by the NR3A subunit of NMDA. Also discovered are the nucleic acid sequences encoding said novel protein and variants thereof. The discovery is useful for the diagnosing of NMDA receptor dysregulation and the treatment of NMDA receptor dysregulation related disorders. In addition, the discovery is useful for the further discovery of modulators affecting the activity of the novel protein and variants thereof at the NMDA receptor.

7 Claims, 28 Drawing Sheets

OTHER PUBLICATIONS

Bork and Bairoch (Oct. 1996) Trends in Genetics 12(10): 425.*

Yu et al, 1999. Science. 284: 336-339.*

Cho, K.O. et al., The Rat Brain Postsynaptic Density Fraction Contains a Homolog of the Drosphia Discs-Large Tumor Suppressor Protein, Neuron 9:929-942 (1992).

Coward et al., Chimeric G Proteins Allow a High-Throughput Signaling Assay of Gj-Coupled Receptors, Analyt. Biochem. 270:242-248 (1999).

Cull-Candy et al., NMDA Receptor Subunits: Diversity, Development and Disease, Curr. Opin. Neurobiol. 11:327-335 (2001).

Das et al., Increased NMDA current and Spine Density in Mice Lacking the NMDA Receptor Subunit NR3A, Nature 393:377-381 (1998).

Dickenson, A.H., A Cure for Wind Up: NMDA Receptor Antagonists as Potential Analgesics, Trends Pharmacol. Sci., 11. 307-309, (1990).

Eilers et al., in Single-Channel Recording, 2nd Ed., Ch. 9, pp. 213-229, (1995), edited by Bert Sakmann and Erwin, Plunum Press, New York.

Elbashir et al., Duplexes pf 21—Nucleotide RNAs Mediate RNA Interference in Cultures Mammalian Cells, Nature 411:494-498 (2001).

Foster et al., Taking Apart NMDA Receptors, Nature, 329:395-396, (1987).

Galderisi et al., Antisense Oligonucleotides as Therapeutic Agents, J. Cell Physiol. 181:251-257 (1999).

Grynkiewitz et al., A New Generation of $Ca^{2+}$ Indicators With Greatly Improved Fluorescence Properties, J. Biol. Chem. 260:3440-3450 (1985).

Hamill et al., Improved Patch-Clamp Techniques for High-Resolution Current Recording from Cells and cell-Free Membrane Patches, Pflugers Arch. 391:85-100 (1981).

Kim, E., et al., Clustering of Shaker-type K+ Channels by Interaction with a Family if Membrane-associated Guanylate Kinases, Nature 378:85-88 (1995).

Lewin et al., Ribozyme Gene Therapy: Applications for Molecular Medicine, Trends Mol. Med. 7:221-228 (2001).

Li et al., In Vitro Selection of Peptides Acting at a New Site of NMDA Glutamate Receptors, Nature 14:986-991 (1996).

Lipton et al., Excitatory Amino Acids as a Final Common Pathway for Neurologic Disorders, New Engl. J. Med. 330:613-622 (1994).

Miyawaki et al., Dynamic and Quantitative $Ca^{2+}$ Measurements Using Improved Cameleons, Proc. Natl. Acad. Sci. USA 96:2135-2140 (1999).

Moore et al., Isoproterenol Stimulates Rapid Extrusion of Sodium From Isolated Smooth Muscle Cells, Proc. Natl. Acad. Sci. USA 90:8058-8062 (1993).

Paucek et al., Reconstitution and Partial Purification of the Glibenclamide-sensitive, ATP-dependent K+ Channel . . . , J. Biol. Chem., 267:26062-26069 (1992).

Sullivan et al., in Calcium Signal Protocol, Methods in Molecular Biology 114: 125-133, Edited by David G. Lambert, Human Press, Totowa, New Jersey (1999).

Woods, D.F. and Bryant, P.J., ZO-1, DIgA and PSD-95/SAP90: homologous Proteins in Tight, Septate and Synaptic Cell Junctions, Mech. Dev. 44:889 (1993).

Xu et al., Regulation of [Na+]j in Resting and Stimulated Submandibular Salivary Ducts, J. Biol. Chem. 270: 19606-19612 (1995).

* cited by examiner

```
              1          15 16         30 31         45 46         60 61         75 76         90
  PNN1154 MFSWLLRLFQKENGD EGETRPTEKEEGILS HEKGRRKSFWRRHRS ARNTSTQNSKMTKKR SKINELEELKLDMRK ISNDMEEMCGILNLY    90
  PNN1152 MFSWLLRLFQKENGD EGETRPTEKEEGILS HEKGRRKSFWRRHRS ARNTSTQNSKMTKKR SKINELEELKLDMRK ISNDMEEMCGILNLY    90
  PNN1157 MFSWLLRLFQKEHGD EGETRPTEKEEGILS HEKGRRKSFWRRHRS ARNTSTQNSKMTKKR SKINELEELKLDMRK ISNDMEEMCGILNLY    90
  PNN1170 MFSWLLRLFQKENGD EGETRPTEKEEGILS HEKGRRKSFWRRHRS ARNTSTQNSKMTKKR SKINELEELKLDMRK ISNDMEEMCGILNLY    90
  PNN1153 MFSWLLRLFQKETGD EGETRPTEKEEGILS HEKGRRKSFWRRHRS ARNTSTQNSKMTKKR SKINELEELKLDMRK ISNDMEEMCGILNLY    90

PNN1155 MFSWLLRLFQKENGD EGETRPTEKEEGILS HEKGRRKSFWRRHRS ARNTSTQNSKMTKKR SKINELEELKLDMRK ISNDMEEMCGILNLY    90
  PNN1159 MFSWLLRLFQKETGD EGETRPTEKEEGILS HEKGRRKSFWRRHRS ARNTSTQNSKMTKKR SKINELEELKLDMRK ISNDMEEMCGILNLY    90
  PNN1166 MFSWLLRLFQKENGD EGETRPTEKEEGILS HEKGRRKSFWRRHRS ARNTSTQNSKMTKKR SKINELEELKLDMRK ISNDMEEMCGILNLY    90
  PNN1137 --------------- --------------- --------------- ----------MTKKR SKINELEELKLDMRK ISNDMEEMCGILNLY    35
  PNN1176 --------------- --------------- --------------- ----------MTKKR SKINELEELKLDMRK ISNDMEEMCGILNVY    35

PNN1139 --------------- --------------- --------------- ----------MTKKR SKINELEELKLDMRK ISNDIEEMCGILNLY    35
  PNN1105 --------------- --------------- --------------- ----------MTKKR SKINELEELKLDMRK ISNDMEEMGGILNLY    35
  PNN1136 --------------- --------------- --------------- ----------MTKKR SKINELEELKLDMRK ISNDMEEMCGILNLY    35
  PNN1113 --------------- --------------- --------------- ----------MTKKR SKINELEELKLDMRK ISNDMEEMCGILNLY    35
  PNN1168 --------------- --------------- --------------- ----------MTKKR SKRNELEELKLDMRK ISNDMEEMCGILNLY    35

PNN1143 --------------- --------------- --------------- ----------MTKKR SKINELEELKLDMRK ISNDMEEMCGILNLY    35
  PNN1174 ---MAMKERPDQQRR KRESFLKKEEGNHS GEGTGLLEILQ---- -----PKIPKMTKKR SKINELEELKLDMRK ISNDMEEMCGILNLY    78
  PNN1131 --------------- --------------- --------------- ----------MTKKR SKINELEELKLDMRK ISNDMEEMCGILNLY    35
  PNN1149 --------------- --------------- --------------- ----------MTKKR SKRNSLEELKLDMRK ISNDMEEMCGILNLY    35
  PNN1132 --------------- --------------- --------------- ----------MTKQR SKINELEELKLDMRK ISNDMEEMCGILNLY    35

PNN1102 --------------- --------------- --------------- ----------MTKKR SKINELEELKLDMRK ISNDMEEMCGILNLY    35
  PNN1108 --------------- --------------- --------------- ----------MTKKR SKINELEELKLDMRK ISNDMEEMCGILNLY    35
  PNN1196 --------------- --------------- --------------- ----------MTKKR SKINELEELKLDMRK ISNDMEEMCGILNLY    35
  PNN1118 --------------- --------------- --------------- ----------MTKKR SKRNELEELKLDMRK ISNDMEEMCGILNLY    35
  PNN1150 --------------- --------------- --------------- ----------MTKKR SKINELEELKLDMRK ISNDMEEMCGILNLY    35

PNN1183 --------------- --------------- --------------- ----------MTKKR SKRNELEELKLDMRK ISNDMEEMCGILNLY    35
  PNN1130 --------------- --------------- --------------- ----------MTKKR SKRNELEELKLDMRK ISNDMEEMCGILNLY    35
  PNN1165 --------------- --------------- --------------- ----------MTKKR SKRNELEELKLDMRK ISNDMEEMCGILNLY    35
  PNN1104 --------------- --------------- --------------- ----------MTKKR SKINELEELKLDMRK ISNDMEEMCGILNLY    35
  PNN1179 --------------- --------------- --------------- ----------MTKKR SKINELEELKLDMRK ISNDMEEMCGILNLY    35

PNN1103 --------------- --------------- --------------- --------------- -----------MRK ISNDMEEMGGILELY    18
  PNN1101 --------------- --------------- --------------- --------------- -----------MRK ISNDMEEMGGILELY    18
  PNN1128 --------------- --------------- --------------- --------------- -----------MRK ISNDMEEMCGILDLY    18
  PNN1125 --------------- --------------- --------------- --------------- -----------MRK ISNDMEEMCGILDLY    18
```

Figure 4a part 1 of 3

```
            91       105 106        120 121        135 136        150 151        165 166        180
PNN1154 MYEDLNYRMNTEFNI IKSQHEKTMLDMNKM IQSIIGSMQYSKELI EDNYSYSIKEDHLLR ECTQLNENVRILLNE NRRLLVEQAGHKCPV  180
PNN1152 MYEDLNYRMNTEFNI IKSQHEKTMLDMNKM IQSIIGSMQYSKELI EDNYSYSIKEDHLLR ECTQLNENVRILLNE NRRLLVEQAGYKCPV  180
PNN1157 MYEDLNYRMNTEFNI IKSQHEKTMLDMNKM IQSIIGSMQYSKELI EDNYSYSIKEDHLLR ECTQLNENVRILLNE NRRLLVEQAGHKCPV  180
PNN1170 MYEDLNYRMNTEFNI IKSQHEKTMLDMNKM IQSIIGSMQYSKELI EDNYSYSIKEDHLLR ECTQLNENVRILLNE NRRLLVEQAGHKCPV  180
PNN1153 MYEDLNYRMNTEFNI IKSQHEKTMLDMNKM IQSIIGSMQYSKELI EDNYSYSIKEDHLLR ECTQLNENVRILLNE NRRLLVEQAGHKCPV  180

PNN1155 MYEDLNYRMNTEFNI IKSQHEKTMLDMNKM IQSIIGSMQYSMELI EDNYSYSIKEDHLLR ECTQLNENVRILLNE NRRLMVEQAGHKCPV  180
PNN1159 MYEDLNYRMNTEFNI IKSQHEKTMLDMNKM IQSIIGSMQYSKELI EDNYSYRALAGIIGL VGVASQWN---LAGN HQFFFVDQH------  171
PNN1166 MYEDLNYRMNTEFNI IKSQHEKTMLDMNKM IQSIIGSMQYSKELI EDNYSYRALAGIIGL VGVASQWN---LAGN HQFFFVDQH------  171
PNN1137 MYEDLNYRMNTEFNI IKSQHEKTMLDMNKM IQSIIGSMQYSKELI EDNYSYSIKEDHLLR ECTQLHENVRILLNE NRRLLVEQAGHKCPV  125
PNN1176 MYEDLNYRMNTEFNI IKSQHEKTMLDMNKM IQSIIGSMQYSKELI EDNYSYSIKEDHLLR ECTQLHENVRILLNE NRRLLVEQAGHKCPV  125

PNN1139 MYEDLNYRMNTEFNI IKSQHEKTMLDMNKM IQSIIGSMQYSKELI EDNYSYSIKEDHLLR ECTQLHENVRILLNE NRRLLVEQAGHKCPV  125
PNN1105 MYEDLNYRMNTEFNI IKSQHEKTMLDMNKM IQSIIGSMQYSKELI EDNYSYSIKEDHLLR DCTQLNENVRILLNE NRRLLVEQAGHKCPV  125
PNN1136 MYEDLNYRMNTEFNI IKSQHEKTMLDMNKM IQSIIGSMQYSKELI EDNYSYSIKEDHLLR ECTQLNENVRILLNE NRRLLVEQAGHKCPV  125
PNN1113 MYEDLNYRMNTEFNI IKSQHEKTMLDMNKM IQSIIGSMQYSKELI EDNYSYSIKEDHLLR ECTQLHENVRILLNE NRRLLVEQAGHKCPV  125
PNN1168 MYEDLNYRMNTEFNI IKSQHEKTMLDMNKM IQSIIGSMQYSKELI EDNYSYSIKEDHLLR ECTQLHENVRILLNE NRRLLVEQAGHKCPV  125

PNN1143 MYEDLNYRMNTEFNI IKSQHEKTMLDMNKM IQSIIGSMQYSKELI EDNYSYSIKEDHLLR ECTQLNEKVRILLNE NRRLLVEQAGHKCPV  125
PNN1174 MYEDLNYRMNTEFNI IKSQHEKTMLDMNKM IQSIIGSMQYSKELI EDNHSYSIKEDHLLR ECTQLNENVRILLNE NRRLLVEQAGYKCPV  169
PNN1131 MYEDLNYRMNTEFNI IKSQHEKTMLDMNKM IQSIIGSMQYSKELI EDNYSYSIKEDHLLR ECTQLNENVRILLNE NRRLLVEQAGHKCPV  125
PNN1149 MYEDLNYRMNTEFNI IKSQHEKTMLDMNKM IQSIIGSMQYSKELI EDNYSYSIKEDHLLR ECTQLNENVRILLNE NRRLLVEQSGHKCPV  125
PNN1132 MYEDLNYRMNTEFNI IKSQHEKTMLDMNKM IQSIIGSMQYSKELI EDNYSYSIKEDHLLR ECTQLNENVRILLNE NRRLLVEQAGHKCPV  125

PNN1102 MYEDLNYRMNTEFNI IKSQHEKTMLDMNKM IQSIIGSMQYSKELI EDNYSYSIKEDHLLR ECTQLHENVRILLNE NRRLLVEQAGHKCPV  125
PNN1108 MYEDLNYRMNTEFNI IKSQHEKTMLDMNKM IQSITVSMQYSKELI EDNYSYSIKEDHLLR ECTQLHENVRILLNE NRRLLVDQAGHKCPV  125
PNN1196 MYEDLNYRMNTEFNI IKSQHEKTMLDMNKM IQSIIGSMQYSKELI EDNYSYSIKEDHLLR ECTQLHENVRILLNE NRRLLVEQAGHKCPV  125
PNN1118 MYEDLNYRMNTEFNI IKSQHEKTMLDMNKM IQSIIGSMQYSKELI EDNYSYSIKEDHLLR ECTQLHENVRILLNE NRRLLVEQAGHKCPV  125
PNN1150 MYEDLNYRMNTEFNI IKSQHEKTMLDMNKM IQSIIGSMQYSKELI EDNYSYSIKEDHLLR ECTQLHENVRILLNE NRRLLVEQAGHKCPV  125

PNN1183 MYEDLNYRMNTEFNI IKSQHEKTMLDMNKM IQSIIGSMQYSKELI EDNYSYSIKEDHLLR ECTQLHENVRILLNE NRRLLVEQAGHKCPV  125
PNN1130 MYEDLNYRMNTEFNI IKSQHEKTMLDMNKM IQSIIGSMQYSKELI EDNYSYSIKEDHLLR ECTQLNENVRILLNE NRRLLVEQAGHKCPV  125
PNN1165 MYEDLNYRMNTEFNI IKSQHEKTMLDMNKM IQSIIGSMQYSKELI EDNYSYSIKEDHLLR ECTQLHENVRILLNE NRRLLVEQAGHKCPV  125
PNN1104 MYEDLNYRMNTEFNI IKSQHEKTMLDMNKM IQSIIGSMQYSKELI EDNYSYSIKEDHLLR ECTQLHENVRILLNE NEGCWWSRLATSVLW  125
PNN1179 MYEDLNYRMNTEFNI IKSQHEKTMLDMNKM IQSIIGSMQYSKELI EDNYSYSPAESRTWH RPGHDLPQREVLEEE H--------------  111

PNN1103 IYEDLNYRMNTEFNI IKSQHEKTMLDMNEM IQSIIVSMQYSKELI EDNYSYSIKEDHLLR ECTQLSEKVRILLNE NRKLLVEQAGTQLSH  108
PNN1101 IYEDLNYRMNTEFNI IKSQHEKTMLDMNEM IQSIIVSMQYSKELI EDNYSYSV------- --------------- ---------------   71
PNN1128 IYEDLNYRMNTEFNI IKSQHEKTILDMNKM IQSIIGSMQYSKELI EDNYSYSIKEDHLLR ECTQLHENVRILLNE NRRLLVEQAGHKCPV  108
PNN1125 MYEDLNYRMNTEFNI IKSQHEKTMLDMNKM IQSIIGSMQYSKELI EDNYSYSVK------ --------------- ---------------   72
```

Figure 4a part 2 of 3

```
         181         195 196        210 211          225 226
PNN1154  GKKRGSLRKPARTSV SQVPRNSSVK----  ---------------- ---    205
PNN1152  GKKRGSLRRPARTSV SQVPRNSSVK----  ---------------- ---    205
PNN1157  GKKRGSLRRPARTSV SQVPRNSSVI----  ---------------- ---    205
PNN1170  GKKRGSLRRPGSTSV SQVPRNSSVI----  ---------------- ---    205
PNN1153  GKKRGSLRRPARTSV SQVPRNSSVK----  ---------------- ---    205

PNN1155  GKKRGSLRRPARTSV SQVPRNSSPAESRTW HRPGHDLPQREVLEE EH-    227
PNN1159  ---------------  ---------------  ---------------- ---    171
PNN1166  ---------------  ---------------  ---------------- ---    171
PNN1137  GKKRGSLRRPARTSV SQVPRNSSPAESRTW H--------------- ---    156
PNN1176  GKKRGSLRRPARTSV SQVPRNSSPAESRTW HRPGHDLPQREVLEE EH-    172

PNN1139  GKKRGSLRRPARTSV SQVPRNSSPAESRTW HRPGHDLPQREVLEE EH-    172
PNN1105  GKKRGSLRRPARTSV SQVPRNSSPAESRTW HRPGHDLPQREVLEE EH-    172
PNN1136  GKKRGSVRRPARTSV SQVPRNSSPAESRTW HRPGHDLPQREVLEE EH-    172
PNN1113  GKKRGSLRKPDKTSV SQVPRNSSPAESRTW HRPGHDLPQREVLEE EH-    172
PNN1168  GKKRGSLRRPARTSV SQVPRNSSPAESRTW HRPGHDLPQREVLEE EH-    172

PNN1143  GKKRGSLRKPARTSV SQVPRNSSVK----  ---------------- ---    150
PNN1174  GKKRGSLRRPARTSV SQVPRNSSVK----  ---------------- ---    193
PNN1131  GKKRGSLRRPARTSV SQVPRNSSVI----  ---------------- ---    150
PNN1149  GKKRGSLRRPARTSV SQVPRNSSVI----  ---------------- ---    150
PNN1132  GKKRGSLRRPARTSV SQVPRNSS------  ---------------- ---    148

PNN1102  GKKRGSLRRPARTSV PQVPRSSSVI----  ---------------- ---    150
PNN1108  GKKRGSLRRPARTSV SQVPRNTSVK----  ---------------- ---    150
PNN1196  GKKRGSLRRPARTSV SQVPRNTSVK----  ---------------- ---    150
PNN1118  GKKRGSLRRPARTSV SQVPRNTSVI----  ---------------- ---    150
PNN1150  GKKRGSLRRPARTSV SQVPRNTSVI----  ---------------- ---    150

PNN1183  GKKRGSLRRPARTSV SQVPRNSSVK----  ---------------- ---    150
PNN1130  GKKRGSLRRPQEHLC PKCQGTAV------  ---------------- ---    148
PNN1165  GKKVL----------  ---------------  ---------------- ---    131
PNN1104  GRKEVL---------  ---------------  ---------------- ---    131
PNN1179  ---------------  ---------------  ---------------- ---    111

PNN1103  GEEKRFCEEASKNIC ASSAKEQQCVNSSRN RHMAQTTT------- ---    146
PNN1101  ---------------  ---------------  ---------------- ---     71
PNN1128  GRKVVL---------  ---------------  ---------------- ---    114
PNN1125  ---------------  ---------------  ---------------- ---     72.
```

Figure 4a part 3 of 3

```
              0         10        20        30        40        50        60
PNN1154     GGATCCCACGGGTCCATGAGAGGCTCCAGGAGAGGCACCCCAGAAAAGGACCAAGCTGGG
PNN1152     GGATCCCACGGGTCCATGAGAGGCTCCAGGAGAGGCACCCCAGAAAAGGACCAAGCTGGG
PNN1157     GGATCCCACGGGTCCATGAGAGGCTCCAGGAGAGGCACCCCAGAAAAGGACCAAGCTGGG
PNN1170     GGATCCCACGGGTCCATGAGAGGCTCCAGGAGAGGCACCCCAGAAAAGGACCAAGCTGGG
PNN1153     GGATCACACGGGTCCATGAGAAGCTCCAGGAGAGGCACCCCAGAAAGGGACCAAGCTGGG
PNN1155     ------------------------------------------------------------
PNN1159     GGATCACACGGGTCCATGAGAAGCTCCAGGAGAGGCACCCCAGAAAAGGACCAAGCTGGG
PNN1166     ------------------------------------------------------------
PNN1137     ------------------------------------------------------------
PNN1176     ------------------------------------------------------------
PNN1139     ------------------------------------------------------------
PNN1105     ------------------------------------------------------------
PNN1136     ------------------------------------------------------------
PNN1113     ------------------------------------------------------------
PNN1168     ------------------------------------------------------------
PNN1143     ------------------------------------------------------------
PNN1174     GGATCCCACGGGTCCATGAGAGGCTCCAGGAGAGGCACCCCAGAAAAGGACCAAGCTGGG
PNN1131     ------------------------------------------------------------
PNN1149     ------------------------------------------------------------
PNN1132     ------------------------------------------------------------
PNN1102     ------------------------------------------------------------
PNN1108     ------------------------------------------------------------
PNN1196     ------------------------------------------------------------
PNN1118     ------------------------------------------------------------
PNN1150     ------------------------------------------------------------
PNN1183     ------------------------------------------------------------
PNN1130     ------------------------------------------------------------
PNN1165     ------------------------------------------------------------
PNN1104     ------------------------------------------------------------
PNN1179     ------------------------------------------------------------
PNN1103     ------------------------------------------------------------
PNN1101     ------------------------------------------------------------
PNN1128     ------------------------------------------------------------
PNN1126     ------------------------------------------------------------
```

Figure 4b part 1 of 18

```
            60        70         80         90        100        110       120
PNN1154  CAGAACTAGTTAACAGGTAGGTCATGGCAGTTGCTAGTGACATCATCAGTAATGCCTTCC
PNN1152  CAGAACTAGTTAACAGGTAGGTCATGGCAGTTGCTAGTGACATCATCAGTAATGCCTTCC
PNN1157  CAGAACTAGTTAACAGGTAGGTCATGGCAGTTGCTAGTGACATCATCAGTAATGCCTTCC
PNN1170  CAGAACTAGTTAACAGGTAGGTCATGGCAGTTGCTAGTGACATCATCAGTAATGCCTTCC
PNN1153  CAGAACTAGTTAACAGGTAGGTCATGGCAGTTGCTAGTGACATCATCAGTAATGCCTTCC
PNN1155  ------------------------------------------------------------
PNN1159  CAGAACTAGTTAACAGGTAGGTCATGGCAGTTGCTAGTGACATCATCAGTAATGCCTTCC
PNN1166  ------------------------------------------------------------
PNN1137  ------------------------------------------------------------
PNN1176  ------------------------------------------------------------
PNN1139  ------------------------------------------------------------
PNN1105  ------------------------------------------------------------
PNN1136  ------------------------------------------------------------
PNN1113  ------------------------------------------------------------
PNN1168  ------------------------------------------------------------
PNN1143  ------------------------------------------------------------
PNN1174  CAGAACTAGTTAACAGGTAGGTCATGGCAGTTGCTAGTGACATCATCAGTAATGCCTTCC
PNN1131  ------------------------------------------------------------
PNN1149  ------------------------------------------------------------
PNN1132  ------------------------------------------------------------
PNN1102  ------------------------------------------------------------
PNN1108  ------------------------------------------------------------
PNN1196  ------------------------------------------------------------
PNN1118  ------------------------------------------------------------
PNN1150  ------------------------------------------------------------
PNN1183  ------------------------------------------------------------
PNN1130  ------------------------------------------------------------
PNN1165  ------------------------------------------------------------
PNN1104  ------------------------------------------------------------
PNN1179  ------------------------------------------------------------
PNN1103  ------------------------------------------------------------
PNN1101  ------------------------------------------------------------
PNN1128  ------------------------------------------------------------
PNN1125  ------------------------------------------------------------
```

Figure 4b part 2 of 18

```
             120       130       140       150       160       170      180
PNN1154    TTGGAGAATCTCTTGTATCTAGGATAGAACTAGAATCCTCTGCGTTGTCACCTGTGTTGT
PNN1152    TTGGAGAATCTCTTGTATCTAGGATAAAACTAGAATCCTCTGCGTTGTCACCTGTGTTGT
PNN1157    TTGGAGAATCTCTTGTATCTAGGATAGAACTAGAATCTTCTGTGTTGTCACCTGTGTTGT
PNN1170    TTGGAGAATCTCTTGTATCTAGGATAGAACTAGAATCCTCTGTGTTGTCACCTGTGTTGT
PNN1153    TTGGAGAATCTCTTGTATCTAGGATAGAACTAGAATCCTCTGCGTTGTCACCTGTGTTGT
PNN1155    ------------------------GGATCCCACGGGTC--CATGAGAGGCTC
PNN1159    TTGGAGAATCTCTTGTATCTAGGATAGAACTAGAATCCTCTGCGTTGTCACCTGTGTTGT
PNN1166    ------------------------GGATCCCACGGGTC--CATGAGAGGCTC
PNN2137    ------------------------------------------------------------
PNN1176    ----------------------------------CAGGAGCAGTGGCTAAATGT
PNN1139    ------------------------------------------------------------
PNN1105    ------------------------------------------------------------
PNN1136    ------------------------------------------------------------
PNN1113    ------------------------------------------------------------
PNN1168    ------------------------------------------------------------
PNN1143    ------------------------------------------------------------
PNN1174    TTGGAGAATCTCTTGTATCTAGGATAAAACTAGAATCCTCTGCGTTGTCACCTGTGTTGT
PNN1131    ------------------------------------------------------------
PNN1149    ------------------------------------------------------------
PNN1132    ------------------------------------------------------------
PNN1102    ------------------------------------------------------------
PNN1108    ------------------------------------------------------------
PNN1196    ----------------------------------CAGGAGCAGTGGCTAAATGT
PNN1118    ------------------------------------------------------------
PNN1150    ------------------------------------------------------------
PNN1183    ----------------------------------CAGGAGCAGTGG
PNN1130    ------------------------------------------------------------
PNN1165    ------------------------------------------------------------
PNN1104    ------------------------------------------------------------
PNN1179    ----------------------------------CAGGAGCAGTGG
PNN1103    ------------------------------------------------------------
PNN1101    ------------------------------------------------------------
PNN1128    ------------------------------------------------------------
PNN1125    ------------------------------------------------------------
```

Figure 4b part 3 of 18

```
           180       190       200       210       220       230       240
PNN1154  GGTGACAGCAACTGCCTGTGGTTCATCCCTTCTGTTTGCTCTGGGTTCACCAGCAGGAAT
PNN1152  GGTGACAGCAACTGCCTGTGGTTCATCCCTTCTGTTTGCTCTGGGTTCACCAGCAGGAAT
PNN1157  GGTGACAGCAACTGCCTGTGGTTCATCCCTTCTGTTTGCTCTGGGTTCACCAGCAGGAAT
PNN1170  GGTGACAGCAACTGCCTGTGGTTCATCCCTTCTGTTTGCTCTGGGTTCACCAGCAGGAAT
PNN1153  GGTGACAGCAACTGCCTGTGGTTCATCCCTTCTGTTTGCTCTGGGTTCACCAGCAGGAAT
PNN1155  CAGGAGAGGCACC--CCAGAAAAGGACCAAGCTGGACAGAACTAG--TTAAC---AGGAAT
PNN1159  GGTGACAGCAACTGCCTGTGGTTCATCCCTTCTGTTTGCTCTGGGTTCACCAGCAGGAAT
PNN1166  CAGGAGAGGCACC-CCAGAAAAGGACCAAGCTGGGCAGAACTAG--TTAACAGCAGGAAT
PNN1137  ------------------------------------------------------------
PNN1176  TGAACTCTTCAAAACTTGGCGTATG---------GGCTGCTGGTGTACCACCATCATCCCC
PNN1139  ------------------------------------------------------------
PNN1105  ------------------------------------------------------------
PNN1136  ------------------------------------------------------------
PNN1113  ------------------------------------------------------------
PNN1168  ------------------------------------------------------------
PNN1143  ------------------------------------------------------------
PNN1174  GGTGACAGCAACTGCCTGTGGTTCATCCCTTCTGTTTGCTCTGGGTTCACCAGCAGGAAT
PNN1131  ------------------------------------------------------------
PNN1149  ------------------------------------------------------------
PNN1132  ------------------------------------------------------------
PNN1102  ------------------------------------------------------------
PNN1108  ------------------------------------------------------------
PNN1196  TGAACTCTTCAAAACTTGGCGTATG---------GGCTGCTGGTGTACCACCATCATCCCC
PNN1118  ------------------------------------------------------------
PNN1150  ------------------------------------------------------------
PNN1183  CTAAATGTTGAACTCTTCAAAACTTGGCGTATGGGCTGCTGGTGTACCACCATCATCCCC
PNN1130  ------------------------------------------------------------
PNN1165  ------------------------------------------------------------
PNN1104  ------------------------------------------------------------
PNN1179  CTAAATGTTGAACTCTTCAAAACTTGGCGTATGGGCTGCTGGTGTACCACCATCATCCCC
PNN1103  ------------------------------------------------------------
PNN1101  ------------------------------------------------------------
PNN1128  ------------------------------------------------------------
PNN1125  ------------------------------------------------------------
```

Figure 4b part 4 of 18

```
              240       250       260       270       280       290       300
PNN1154   GTTTTCCTGGCTGCTCAGGCTATTTCAGAAAGAGAATGGCGATGAAGGAGAGACCAGACC
PNN1152   GTTTTCCTGGCTGCTCAGGCTATTTCAGAAAGAGAATGGCGATGAAGGAGAGACCAGACC
PNN1157   GTTTTCCTGGCTGCTCAGGCTATTTCAGAAAGAGAATGGCGATGAAGGAGAGACCAGACC
PNN1170   GTTTTCCTGGCTGCTCAGGCTATTTCAGAAAGAGAATGGCGATGAAGGAGAGACCAGACC
PNN1153   GTTTTCCTGGCTGCTCAGGCTATTTCAGAAAGAGACTGGCGATGAAGGAGAGACCAGACC
PNN1155   GTTTTCCTGGCTGCTCAGGCTATTTCAGAAAGAGAATGGCGATGAAGGAGAGACCAGACC
PNN1159   GTTTTCCTGGCTGCTCAGGCTATTTCAGAAAGAGACTGGCGATGAAGGAGAGACCAGACC
PNN1166   GTTTTCCTGGCTGCTCAGGCTATTTCAGAAAGAGAATGGCGATGAAGGAGAGACCAGACC
PNN1137   ------------------------------------------------------------
PNN1176   AACACTCCTGTTCAGAAGATGGGTGAGGAAAGTGGAAAGT--CTAACCAGTCAGCCGATG
PNN1139   ------------------------------------------------------------
PNN1105   ------------------------------------AAGC--CTAACCACTCAGCCGATG
PNN1136   ------------------------------------------------------------
PNN1113   ------------------------------------AAGT--CTAACCAGTCAGCCGATG
PNN1168   ----------------------------------------------GGATCACACGGGTC
PNN1143   ------------------------------------------------------------
PNN1174   GTTTTCCTGGCTGCTCAGGCTATTTCAGAAAGAGAATGGCGATGAAGGAGAGACCAGACC
PNN1131   ------------------------------------------------------------
PNN1149   ------------------------------------------------------------
PNN1132   ------------------------------------------------------------
PNN1102   ------------------------------------AAAGTCTAATCAGTCAGCCGATG
PNN1108   ------------------------------------AAGT--CTAATCAGTCAGCCGATG
PNN1196   AACACTCCTGTTCAGAAGATGGGTGAGGAAAGTGGAAAGT--CTACCCAGTCAGCCGATG
PNN1118   ------------------------------------AAGT--CTAATCAGTCAGCCGATG
PNN1150   ------------------------------------------------------------
PNN1183   AACACTCCTGTTCAGAAGATGGGTGAGGAAAGTGGAAAGT--CTAATCAGTCAGCCGATG
PNN1130   ------------------------------------------------------------
PNN1165   ------------------------------------------------------------
PNN1104   ------------------------------------AAGT--CTACCCAGTCAGCCGATG
PNN1179   AACACTCCTGTTCAGAAGATGGGTGAGGAAAGTGGAAAGT--CTAATCAGTCAGCCGATG
PNN1103   --------------------------------------AAGTCTAATCAGTCAGCCGATG
PNN1101   ------------------------------------AAGT--CTAATCAGTCAGCCGATG
PNN1128   ------------------------------------------------------------
PNN1125   ------------------------------------AAGT--CTAATCAGTCAGCCGATG
```

Figure 4b part 5 of 18

```
              300       310       320       330       340       350       360
PNN1154  AACAGAGAAGGAAGAGGGAATCCTTTCTCATGAAAAAGGAAGAAGGAAATCATTCTGGAG
PNN1152  AACAGAGAAGGAAGAGGGAATCCTTTCTCATGAAAAAGGAAGAAGGAAATCATTCTGGAG
PNN1157  AACAGAGAAGGAAGAGGGAATCCTTTCTCATGAAAAAGGAAGAAGGAAATCATTCTGGAG
PNN1170  AACAGAGAAGGAAGAGGGAATCCTTTCTCATGAAAAAGGAAGAAGGAAATCATTCTGGAG
PNN1153  AACAGAGAAGGAAGAGGGAATCCTTTCTCATGAAAAAGGAAGAAGGAAATCATTCTGGAG
PNN1155  AACAGAGAAGGAAGAGGGAATCCTTTCTCATGAAAAAGGAAGAAGGAAATCATTCTGGAG
PNN1159  AACAGAGAAGGAAGAGGGAATCCTTTCTCATGAAAAAGGAAGAAGGAAATCATTCTGGAG
PNN1166  AACAGAGAAGGAAGAGGGAATCCTTTCTCATGAAAAAGGAAGAAGGAAATCATTCTGGAG
PNN1137  ----GACTCAGAATGGTCTCCCCTGCCCCTGGGCCATCAAGTATGCAAATTCTTTTGTGT
PNN1176  ACCAGTGGGAAAAATGAGCTACAAGATCACCTGATCTTCATCAGTGAGAAAGCTTTGCAC
PNN1139  ----GACTCAGAATGGTCTCCCCTGCCCCTGGGCCATCAAGTATGCAAATTCTTTTGTGT
PNN1105  ACAAGTGGGAAAAATGCGCTACAAGATCACCTGATATTCATCAGTGAGAAAGCTTTGCAC
PNN1136  ----GACTCAGAATGGTCTCCCCTGCCCCTGGGCCATCAAGTATGCAAATTCTTTTGTGT
PNN1113  ACCAGTGGGAACAATGAGCTACAAGATCACCTGATCTTCATCAGTGAGAAAGCTTTGCAC
PNN1168  CAT-GAGAGGCTCCAGGAGAGGCACCCCAGAAAAGGACCAAGCTGGGCAGAACT----AG
PNN1143  ----GACTCAGAATGGTCTCCCCTGCCCCTGGGCCTTCAAGTATGCAAATTCTTTTGTGT
PNN1174  AACAGAGAAGGAAGAGGGAATCCTTTCTCATGAAAAAGGAAGAAGGAAATCATTCTGGAG
PNN1131  ----GACTCAGAATGGTCTCCCCTGCCCCTGGGCCATCAAGTATGCAAATTCTTTTGTGT
PNN1149  ----GACTCAGAATGGTCTCCCCTGCCCCTGGGCCATCAAGTATGCAAATTCTTTTGTGT
PNN1132  ----GACTCAGAATGGTCTCCCCTGCCCCTGGGCCATCAAGTATGCAAATTCTTTTGTGT
PNN1102  ACCAGTGGGAAAAATGAGCTACAAGATCACCTGATCTTCATCAGTGAGAAAGCTTTGCAC
PNN1108  ACCAGTGGGAAAAATGAGCTACAAGATCACCTGATCTTCATCAGTGAGAAAGCTTTGCAC
PNN1196  ACCAGTGGGAAAAATGAGCTACAAGATCACCTGATCTTCATCAGTGAGAAAGCTTTGCAC
PNN1118  ACCAGTGGGAACAATGAGCTACAAGATCACCTGATCTTCATCAGTGAGAAAGCTTTGCAC
PNN1150  ----GACTCAGAATGGTCTCCCCTGCCCCTGGGCCATCAAGTATGCAAATTCTTTTGTGT
PNN1183  ACCAGTGGGAAAAATGAGCTACAAGATCACCTGATCTTCATCAGTGAGAAAGCTTTGCAC
PNN1130  ----GACTCAGAATGGTCTCCCCTGCCCCTGGGCCTTCAAGTATGCAAATTCTTTTGTGT
PNN1165  ----GACTCAGAATGGTCTCCCCTGCCCCTGGGCCATCAAGTATGCAAATTCTTTTGTGT
PNN1104  ACCAGTGGGAAAAATGAGCTACAAGATCACCTGATCTTCATCAGTGAGAAAGCTTTGCAC
PNN1179  ACCAGTGGGAAAAATGAGCTACAAGATCACCTGATCTTCATCAGTGAGAAAGCTTTGCAC
PNN1103  ACCAGTGGGAAAAATGAGCTACAAGATCACCTGATCTTCATCAGTGAGAAAGCTTTGCAC
PNN1101  ACCAGTGGGAAAAATGAGCTACAAGATCACCTGATCTTCATCAGTGAGAAAGCTTTGCAC
PNN1128  ----GACTCAGAATGGTCTCCCCTGCGCCTGGGCCATCAAGTATGCAAATTCTTTTGTGT
PNN1125  ACCAGTGGGAAAAATGAGCTACAAGATCACCTGATCTTCATCAGTGAGAAAGCTTTGCAC
```

Figure 4b part 6 of 18

```
              360       370       380       390       400       410       420
PNN1154    AAGGCAC------AGGTCTGCTAGAAATACTTCAACCCAAAATTCCAAAA-TGACTAAGA
PNN1152    AAGGCAC------AGGTCTGCTAGAAATACTTCAACCCAAAATTCCAAAA-TGACTAAGA
PNN1157    AAGGCAC------AGGTCTGCTAGAAATACTTCAACCCAAAATTCCAAAA-TGACCAAGA
PNN1170    AAGGCAC------AGGTCTGCTAGAAATACTTCAACCCAAAATTCCAAAA-TGACTAAGA
PNN1153    AAGGCAC------AGGTCTGCTAGAAATACTTCAACCCAAAATTCCAAAA-TGACCAAGA
PNN1155    AAGGCAC------AGGTCTGCTAGAAATACTTCAACCCAAAATTCCAAAA-TGACTAAGA
PNN1159    AAGGCAC------AGGTCTGCTAGAAATACTTCAACCCAAAATTCCAAAA-TGACCAAGA
PNN1166    AAGGCAC------AGGTCTGCTAGAAATACTTCAACCCAAAATTCCAAAA-TGACTAAGA
PNN1137    TTACCTATCTGCAGGGTCTGCTAGAAATACTTCAACCCAAAATTCCAAAA-TGACTAAGA
PNN1176    AAGA---------GGGTCTGCTAGAAATACTTCAACCCAAAATTCCAAAA-TGACTAAGA
PNN1139    TTACCTATCTGCAGGGTCTGCTAGAAATACTTCAACCCAAAATTCCAAAA-TGACTAAGA
PNN1105    AAGA---------GGGTCTGCTAGAAATACTTCAACCCAAAATTCCAAAA-TGACTAAGA
PNN1136    TTACCTATCTGCAGGGTCTGCTAGAAATACTTCAACCCAAAATTCCAAAA-TGACTAAGA
PNN1113    AAGA---------GGGTCTGCTAGAAATACTTCAACCCAAAATTCCAAAA-TGACTAAGA
PNN1168    TTAACA-------GGGTCTGCTAGAAATACTTCAACCCAAAATTCCAAAA-TGACTAAGA
PNN1143    TTACCTATCTGCAGGGTCTGCTAGAAATACTTCAACCCAAAATTCCAAAA-TGACTAAGA
PNN1174    AAGGCAC------AGGTCTGCTAGAAATACTTCAACCCAAAATTCCAAAAATGACTAAGA
PNN1131    TTACCTATCTGCAGGGTCTGCTAGAAATACTTCAACCCAAAATTCCAAAA-TGACCAAGA
PNN1149    TTACCTATCTGCAGGGTCTGCTAGAAATACTTCAACCCAAAATTCCAAAA-TGACTAAGA
PNN1132    TTACCTATCTGCAGGGTCTGCTAGAAATACTTCAACCAAAATTCCAAAA-TGACTAAGC
PNN1102    AAGA---------GGGTCTGCTAGAAATACTTCAACCCAAAATTCCAAAA-TGACTAAGA
PNN1108    AAGA---------GGGTCTGCTAGAAATACTTCAACCCAAAATTCCAAAA-TGACTAAGA
PNN1196    AAGA---------GGGTCTGCTAGAAATACTTCAACCCAAAATTCCAAAA-TGACTAAGA
PNN1118    AAGA---------GGGTCTGCTAGAAATACTTCAACCCAAAATTCCAAAA-TGACTAAGA
PNN1150    TTACCTATCTGCAGGGTCTGCTAGAAATACTTCAACCCAAAATTCCAAAA-TGACTAAGA
PNN1183    AAGA---------GGGTCTGCTAGAAATACTTCAACCCAAAATTCCAAAA-TGACTAAGA
PNN1130    TTACCTATCTGCAGGGTCTGCTAGAAATACTTCAACCCAAAATTCCAAAA-TGACCAAGA
PNN1165    TTACCTATCTGCAGGGTCTGCTAGAAATACTTCAACCCAAAATTCCAAAA-TGACTAAGA
PNN1104    AAGA---------GGGTCTGCTAGAAATACTTCAACCCAAAATTCCAAAA-TGACTAAGA
PNN1179    AAGA---------GGGTCTGCTAGAAATACTTCAACCCAAAATTCCAAAA-TGACTAAGA
PNN1103    AAGA---------GGGTCTGCTAGAAATACTTCAACCCAAAATTCCAAAA-TCACTAAGC
PNN1101    AAGA---------GGGTCTGCTAGAAATACTTCAACCCAAAATTCCAAAA-TCACTAAGC
PNN1128    TTATCTATCTGCAGGGTCTGCTAGAAATACTTCAACCCAGAATTCCAAAA-TCACTAAGA
PNN1125    AAGA---------GGATCTGCTAGAAATACTTCAACCCAAAAGTCCAAAA-TCACTAAGC
                        *  *******************  *  ** *******  *  **  ***
```

Figure 4b part 7 of 18

```
         .420       430       440      .450       460       470       480
PNN1154  AGAGATCAAAAATAAATGAACTAGAAGAACTGAAATTGGATATGAGGAAGATCAGCAATG
PNN1152  AGAGATCAAAAATAAATGAACTAGAAGAACTGAAATTGGATATGAGGAAGATCAGCAATG
PNN1157  AGAGATCAAAAATAAATGAACTAGAAGAACTGAAATTGGATATGAGGAAGATCAGCAATG
PNN1170  AGAGATCAAAAATAAATGAACTAGAAGAACTGAAATTGGATATGAGGAAGATCAGCAATG
PNN1153  AGAGATCAAAAATAAATGAACTAGAAGAACTGAAATTGGATATGAGGAAGATCAGCAATG
PNN1155  AGAGATCAAAAATAAATGAACTAGAAGAACTGAAATTGGATATGAGGAAGATCAGCAATG
PNN1159  AGAGATCAAAAATAAATGAACTAGAAGAACTGAAATTGGATATGAGGAAGATCAGCAATG
PNN1166  AGAGATCAAAAATAAATGAACTAGAAGAACTGAAATTGGATATGAGGAAGATCAGCAATG
PNN1137  AGAGATCAAAAATAAATGAACTAGAAGAACTGAAATTGGATATGAGGAAGATCAGCAATG
PNN1176  AGAGATCAAAAATAAATGAACTAGAAGAACTGAAATTGGATATGAGGAAGATCAGCAATG
PNN1139  AGAGATCAAAAATAAATGAACTAGAAGAACTGAAATTGGATATGAGGAAGATCAGCAATG
PNN1105  AGAGATCAAAAATAAATGAACTAGAAGAACTGAAATTGGATATGAGGAAGATCAGCAATG
PNN1136  AGAGATCAAAAATAAATGAACTAGAAGAACTGAAATTGGATATGAGGAAGATCAGCAATG
PNN1113  AGAGATCAAAAATAAATGAACTAGAAGAACTGAAATTGGATATGAGGAAGATCAGCAATG
PNN1168  AGAGATCAAAAAGAAATGAACTAGAAGAACTGAAATTGGATATGAGGAAGATCAGCAATG
PNN1143  AGAGATCAAAAATAAATGAACTAGAAGAACTGAAATTGGATATGAGGAAGATCAGCAATG
PNN1174  AGAGATCAAAAATAAATGAACTAGAAGAACTGAAATTGGATATGAGGAAGATCAGCAATG
PNN1131  AGAGATCAAAAATAAATGAACTAGAAGAACTGAAATTGGATATGAGGAAGATCAGCAATG
PNN1149  AGAGATCAAAAAGAAATGAACTAGAAGAACTGAAATTGGATATGAGGAAGATCAGCAATG
PNN1132  AGAGATCAAAAATAAATGAACTAGAAGAAGTGAAATTGGATATGAGGAAGATCAGCAATG
PNN1102  AGAGATCAAAAATAAATGAACTAGAAGAACTGAAATTGGATATGAGGAAGATCAGCAATG
PNN1108  AGAGATCAAAAATAAATGAACTAGAAGAACTGAAATTGGATATGAGGAAGATCAGCAATG
PNN1196  AGAGATCAAAAATAAATGAACTAGAAGAACTGAAATTGGATATGAGGAAGATCAGCAATG
PNN1118  AGAGATCCAAAAGAAATGAACTAGAAGAACTGAAATTGGATATGAGGAAGATCAGCAATG
PNN1150  AGAGATCAAAAATAAATGAACTAGAAGAACTGAAATTGGATATGAGGAAGATCAGCAATG
PNN1183  AGAGATCAAAAAGAAATGAACTAGAAGAACTGAAATTGGATATGAGGAAGATCAGCAATG
PNN1130  AGAGATCAAAAAGAAATGAACTAGAAGAACTGAAATTGGATATGAGGAAGATCAGCAATG
PNN1165  AGAGATCCAAAAGAAATGAACTAGAAGAACTGAAATTGGATATGAGGAAGATCAGCAATG
PNN1104  AGAGATCAAAAATAAATGAACTAGAAGAACTGAAATTGGATATGAGGAAGATCAGCAATG
PNN1179  AGAGATCAAAAAGAAATGAACTAGAAGAACTGAAATTGGATATGAGGAAGATCAGCAATG
PNN1103  AGAGATCAAAAATAAATGAACTAGAAGAACTGAAATTGGATATGAGGAAGATCAGCAATG
PNN1101  AGAGATCAAAAATAAATGAACTAGAAGAACTGAAATTGGATATGAGGAAGATCAGCAATG
PNN1128  AGAGATCAAAAATAAATGAACTAGAAGAATTGAAATTGGATATGAGGAAGATCAGCAATG
PNN1125  AGAAATCAAATATAAATGAACTAGAAGAATTGAATTTGGATATGAGGAAGATCAGTAATG
         *** *** ** * **********  *** * **** ***********************  ****
```

Figure 4b part 8 of 18

```
              480       490       500       510       520       530       540
PNN1154   ACATGGAGGAAATGTGTGGAATCCTGAACCTTTACATGTATGAGGATTTGAACTACAGGA
PNN1152   ACATGGAGGAAATGTGTGGAATCCTGAACCTTTACATGTATGAGGATTTGAACTACAGGA
PNN1157   ACATGGAGGAAATGTGTGGAATCCTGAACCTTTACATGTATGAGGATTTGAACTACAGGA
PNN1170   ACATGGAGGAAATGTGTGGAATCCTGAACCTTTACATGTATGAGGATTTGAACTACAGGA
PNN1153   ACATGGAGGAAATGTGTGGAATCCTGAACCTTTACATGTATGAGGATTTGAACTACAGGA
PNN1155   ACATGGAGGAAATGTGTGGAATCCTGAACCTTTACATGTATGAGGATTTGAACTACAGGA
PNN1159   ACATGGAGGAAATGTGTGGAATCCTGAACCTTTACATGTATGAGGATTTGAACTACAGGA
PNN1166   ACATGGAGGAAATGTGTGGAATCCTGAACCTTTACATGTATGAGGATTTGAACTACAGGA
PNN1137   ACATGGAGGAAATGTGTGGAATCCTGAACCTTTACATGTATGAGGATTTGAACTACAGGA
PNN1176   ACATGGAGGAAATGTGTGGAATCCTGAACGTTTACATGTATGAGGATTTGAACTACAGGA
PNN1139   ACATTGAGGAAATGTGTGGAATCCTAAACCTTTACATGTATGAGGATTTGAACTACAGGA
PNN1105   ACATGGAGGAAATGGGTGGAATCCTGAACCTTTACATGTATGAGGATTTGAACTACAGGA
PNN1136   ACATGGAGGAAATGTGTGGAATCCTGAACCTTTACATGTATGAGGATTTGAACTACAGGA
PNN1113   ACATGGAGGAAATGTGTGGAATCCTGAACCTTTACATGTATGAGGATTTGAACTACAGGA
PNN1168   ACATGGAGGAAATGTGTGGAATCCTGAACCTTACATGTATGAGGATTTGAACTACAGGA
PNN1143   ACATGGAGGAAATGTGTGGAATCCTGAACCTTTACATGTATGAGGATTTGAACTACAGGA
PNN1174   ACATGGAGGAAATGTGTGGAATCCTGAACCTTTACATGTATGAGGATTTGAACTACAGGA
PNN1131   ACATGGAGGAAATGTGTGGAATCCTGAACCTTTACATGTATGAGGATTTGAACTACAGGA
PNN1149   ACATGGAGGAAATGTGTGGAATCCTGAACCTTTACATGTATGAGGATTTGAACTACAGGA
PNN1132   ACATGGAGGAAATGTGTGGAATCCTGAACGTTTACATGTATGAGGATTTGAACTACAGGA
PNN1102   ACATGGAGGAAATGTGTGGAATCCTGAACCTTTACATGTATGAGGATTTGAACTACAGGA
PNN1108   ACATGGAGGAAATGTGTGGAATCCTGAACCTTTACATGTATGAGGATTTGAACTACAGGA
PNN1196   ACATGGAGGAAATGTGTGGAATCCTGAACGTTTACATGTATGAGGATTTGAACTACAGGA
PNN1118   ACATGGAGGAAATGTGTGGAATCCTGAACCTTTACATGTATGAGGATTTGAACTACAGGA
PNN1150   ACATGGAGGAAATGTGTGGAATCCTGAACCTTTACATGTATGAGGATTTGAACTACAGGA
PNN1183   ACATGGAGGAAATGTGTGGAATCCTGAACCTTTACATGTATGAGGATTTGAACTACAGGA
PNN1130   ACATGGAGGAAATGTGTGGAATCCTGAACCTTTACATGTATGAGGATTTGAACTACAGGA
PNN1165   ACATGGAGGAAATGTGTGGAATCCTGAACCTTTACATGTATGAGGATTTGAACTACAGGA
PNN1104   ACATGGAGGAAATGTGTGGAATCCTGAACCTTTACATGTATGAGGATTTGAACTACAGGA
PNN1179   ACATGGAGGAAATGTGTGGAATCCTGAACCTTTACATGTATGAGGATTTGAACTACAGGA
PNN1103   ACATGGAGGAAATGGGTGGAATCCTGGAACTTTACATATATGAGGATTTGAACTACAGGA
PNN1101   ACATGGAGGAAATGGGTGGAATCCTGGAACTTTACATATATGAGGATTTGAACTACAGGA
PNN1128   ACATGGAGGAAATGTGTGGAATCCTGGACCTTTACATATATGAGGATTTGAACTACAGGA
PNN1125   ACATGGAGGAAATGTGTGGAATCCTGGACGTTTACATGTATGAGGATTTGAACTACAGGA
          ****  ********* *********  *  ******* * ******************
```

Figure 4b part 9 of 18

```
                540       550       560       570       580       590       600
PNN1154   TGAACACTGAATTCAACATCATTAAATCACAACATGAGAAGACAATGTTGGATATGAATA
PNN1152   TGAACACTGAATTCAACATCATTAAATCACAACATGAGAAGACAATGTTGGATATGAATA
PNN1157   TGAACACTGAATTCAACATCATTAAATCACAACATGAGAAGACAATGTTGGATATGAATA
PNN1170   TGAACACTGAATTCAACATCATTAAATCACAACATGAGAAGACAATGTTGGATATGAATA
PNN1153   TGAACACTGAATTCAACATCATTAAATCACAACATGAGAAGACAATGTTGGATATGAATA
PNN1155   TGAACACTGAATTCAACATCATTAAATCACAACATGAGAAGACAATGTTGGATATGAATA
PNN1159   TGAACACTGAATTCAACATCATTAAATCACAACATGAGAAGACAATGTTGGATATGAATA
PNN1166   TGAACACTGAATTCAACATCATTAAATCACAACATGAGAAGACAATGTTGGATATGAATA
PNN1137   TGAACACTGAATTCAACATCATTAAATCACAACATGAGAAGACAATGTTGGATATGAATA
PNN1176   TGAACACTGAATTCAACATCATTAAATCACAACATGAGAAGACAATGTTGGATATGAATA
PNN1139   TGAACACTGAATTCAACATCATTAAATCACAACATGAGAAGACAATGTTGGATATGAATA
PNN1105   TGAACACTGAATTCAACATCATTAAATCACAACATGAGAAGACAATGTTGGATATGAATA
PNN1136   TGAACACTGAATTCAACATCATTAAATCACAACATGAGAAGACAATGTTGGATATGAATA
PNN1113   TGAACACTGAATTCAACATCATTAAATCACAACATGAGAAGACAATGTTGGATATGAATA
PNN1168   TGAACACTGAATTCAACATCATTAAATCACAACATGAGAAGACAATGTTGGATATGAATA
PNN1143   TGAACACTGAATTCAACATCATTAAATCACAACATGAGAAGACAATGTTGGATATGAATA
PNN1174   TGAACACTGAATTCAACATCATTAAATCACAACATGAGAAGACAATGTTGGATATGAATA
PNN1131   TGAACACTGAATTCAACATCATTAAATCACAACATGAGAAGACAATGTTGGATATGAATA
PNN1149   TGAACACTGAATTCAACATCATTAAATCACAACATGAGAAGACAATGTTGGATATGAATA
PNN1132   TGAACACTGAATTCAACATCATTAAATCACAACATGAGAAGACAATGTTGGATATGAATA
PNN1102   TGAACACTGAATTCAACATCATTAAATCACAACATGAGAAGACAATGTTGGATATGAATA
PNN1108   TGAACACTGAATTCAACATCATTAAATCACAACATGAGAAGACAATGTTGGATATGAATA
PNN1196   TGAACACTGAATTCAACATCATTAAATCACAACATGAGAAGACAATGTTGGATATGAATA
PNN1118   TGAACACTGAATTCAACATCATTAAATCACAACATGAGAAGACAATGTTGGATATGAATA
PNN1150   TGAACACTGAATTCAACATCATTAAATCACAACATGAGAAGACAATGTTGGATATGAATA
PNN1183   TGAACACTGAATTCAACATCATTAAATCACAACATGAGAAGACAATGTTGGATATGAATA
PNN1130   TGAACACTGAATTCAACATCATTAAATCACAACATGAGAAGACAATGTTGGATATGAATA
PNN1165   TGAACACTGAATTCAACATCATTAAATCACAACATGAGAAGACAATGTTGGATATGAATA
PNN1104   TGAACACTGAATTCAACATCATTAAATCACAACATGAGAAGACAATGTTGGATATGAATA
PNN1179   TGAACACTGAATTCAACATCATTAAATCACAACATGAGAAGACAATGTTGGATATGAATA
PNN1103   TGAACACTGAATTCAACATCATTAAATCACAACATGAGAAGACAATGTTGGATATGAATG
PNN1101   TGAACACTGAATTCAACATCATTAAATCACAACATGAGAAGACAATGTTGGATATGAATG
PNN1128   TGAACACTGAATTCAACATCATTAAATCACAACATGAGAAGACAATATTGGATATGAATA
PNN1125   TGAACACTGAATTCAACATCATTAAATCACAACATGAGAAGACAATGTTGGATATGAATA
```

Figure 4b part 10 of 18

```
              600        610        620        630        640        650        660
PNN1154   AAATGATCCAGTCCATAATTGGTTCCATGCAGTACTCCAAGGAACTGATAGAAGATAACT
PNN1152   AAATGATCCAGTCCATAATTGGTTCCATGCAGTACTCCAAGGAACTGATAGAAGATAACT
PNN1157   AAATGATCCAGTCCATAATTGGTTCCATGCAGTACTCCAAGGAACTGATAGAAGATAACT
PNN1170   AAATGATCCAGTCCATAATTGGTTCCATGCAGTATTCCAAGGAACTGATAGAAGATAACT
PNN1153   AAATGATCCAGTCCATAATTGGTTCCATGCAGTACTCCAAGGAACTGATAGAAGATAACT
PNN1155   AAATGATCCAGTCCATAATTGGTTCCATGCAGTACTCCATGGAACTGATAGAAGATAACT
PNN1159   AAATGATCCAGTCCATAATTGGTTCCATGCAGTACTCCAAGGAACTGATAGAAGATAACT
PNN1166   AAATGATCCAGTCCATAATTGGTTCCATGCAGTATTCCAAGGAACTGATAGAAGATAACT
PNN1137   AAATGATCCAGTCAATAATTGGTTCCATGCAGTACTCTAAGGAACTGATAGAAGATAACT
PNN1176   AAATGATCCAGTCCATAATTGGTTCCATGCAGTACTCCAAGGAACTGATAGAAGATAACT
PNN1139   AAATGATCCAGTCAATAATTGGTTCCATGCAGTACTCTAAGGAACTGATAGAAGATAACT
PNN1105   AAATGATCCAGTCAATAATTGGTTCCATGCAGTACTCTAAGGAACTGATAGAAGATAACT
PNN1136   AAATGATCCAGTCCATAATTGGTTCCATGCAGTACTCCAAGGAACTGATAGAAGATAACT
PNN1113   AAATGATCCAGTCCATAATTGGTTCCATGCAGTACTCCAAGGAACTGATAGAAGATAACT
PNN1168   AAATGATCCAGTCCATAATTGGTTCCATGCAGTATTCCAAGGAACTGATAGAAGATAACT
PNN1143   AAATGATCCAGTCCATAATTGGTTCCATGCAGTACTCCAAGGAACTGATAGAAGATAACT
PNN1174   AAATGATCCAGTCCATAATTGGTTCCATGCAGTACTCCAAGGAACTGATAGAAGATAACC
PNN1131   AAATGATCCAGTCCATAATTGGTTCCATGCAGTACTCCAAGGAACTGATAGAAGATAACT
PNN1149   AAATGATCCAGTCCATAATTGGTTCCATGCAGTACTCCAAGGAACTGATAGAAGATAACT
PNN1132   AAATGATCCAGTCCATAATTGGTTCCATGCAGTACTCCAAGGAACTGATAGAAGATAACT
PNN1102   AAATGATCCAGTCCATAATTGGTTCCATGCAGTACTCCAAGGAACTGATAGAAGATAACT
PNN1108   AAATGATCCAGTCCATAATTGTTTCCATGCAGTACTCCAAGGAACTGATAGAAGATAACT
PNN1196   AAATGATCCAGTCCATAATTGGTTCCATGCAGTACTCCAAGGAACTGATAGAAGATAACT
PNN1118   AAATGATCCAGTCCATAATTGGTTCCATGCAGTACTCCAAGGAACTGATAGAAGATAACT
PNN1150   AAATGATCCAGTCCATAATTGGTTCCATGCAGTACTCCAAGGAACTGATAGAAGATAACT
PNN1183   AAATGATCCAGTCCATAATTGGTTCCATGCAGTATTCCAAGGAACTGATAGAAGATAACT
PNN1130   AAATGATCCAGTCCATAATTGGTTCCATGCAGTACTCCAAGGAACTGATAGAAGATAACT
PNN1165   AAATGATCCAGTCCATAATTGGTTCCATGCAGTACTCCAAGGAACTGATAGAAGATAACT
PNN1104   AAATGATCCAGTCCATAATTGGTTCCATGCAGTACTCCAAGGAACTGATAGAAGATAACT
PNN1179   AAATGATCCAGTCCATAATTGGTTCCATGCAGTATTCCAAGGAACTGATAGAAGATAACT
PNN1103   AAATGATCCAGTCCATAATTGTTTCCATGCAGTACTCCAAGGAACTGATAGAAGATAACT
PNN1101   AAATGATCCAGTCCATAATTGTTTCCATGCAGTACTCCAAGGAACTGATAGAAGATAACT
PNN1128   AAATGATCCAGTCCATAATTGGTTCCATGCAGTACTCCAAGGAACTGATAGAAGATAACT
PNN1125   AAATGATCCAGTCCATAATTGGTTCCATGCAGTACTCCAAGGAACTGATAGAAGATAACT
          ************** ******* ************** ** * ****************
```

Figure 4b part 11 of 18

```
            660       670       680       690       700       710       720
PNN1154   ATTCCTACAG---------------------------------------------------------
PNN1152   ATTCCTACAG---------------------------------------------------------
PNN1151   ATTCCTACAG---------------------------------------------------------
PNN1170   ATTCCTACAG---------------------------------------------------------
PNN1153   ATTCCTACAG---------------------------------------------------------
PNN1155   ATTCCTACAG---------------------------------------------------------
PNN1159   ATTCCTACAGGGCCCTTGCAGGGATCATAGGACTTGTAGGAGTGGCAAGCCAATGGAATC
PNN1166   ATTCCTACAGGGCCCTTGCAGGGATCATAGGACTTGTACGAGTGGCAAGCCAATGGAATC
PNN1137   ATTCCTACAG---------------------------------------------------------
PNN1176   ATTCCTACAG---------------------------------------------------------
PNN1139   ATTCCTACAG---------------------------------------------------------
PNN1105   ATTCCTACAG---------------------------------------------------------
PNN1136   ATTCCTACAG---------------------------------------------------------
PNN1113   ATTCCTACAG---------------------------------------------------------
PNN1168   ATTCCTACAG---------------------------------------------------------
PNN1143   ATTCCTACAG---------------------------------------------------------
PNN1174   ATTCCTACAG---------------------------------------------------------
PNN1131   ATTCCTACAG---------------------------------------------------------
PNN1149   ATTCCTACAG---------------------------------------------------------
PNN1132   ATTCCTACAG---------------------------------------------------------
PNN1102   ATTCCTACAG---------------------------------------------------------
PNN1108   ATTCCTACAG---------------------------------------------------------
PNN1196   ATTCCTACAG---------------------------------------------------------
PNN1118   ATTCCTACAG---------------------------------------------------------
PNN1150   ATTCCTACAG---------------------------------------------------------
PNN1183   ATTCCTACAG---------------------------------------------------------
PNN1130   ATTCCTACAG---------------------------------------------------------
PNN1165   ATTCCTACAG---------------------------------------------------------
PNN1104   ATTCCTACAG---------------------------------------------------------
PNN1179   ATTCCTACAGT--------------------------------------------------------
PNN1103   ATTCCTACAG---------------------------------------------------------
PNN1101   ATTCCTACAGTGTGTAA--------------------------------------------------
PNN1128   ATTCCTACAG---------------------------------------------------------
PNN1125   ATTCCTACAGTGTGAAAT-------------------------------------------------
          **********
```

Figure 4b part 12 of 18

```
          720       730       740       750       760       770       780
PNN1154   ------------------------------------CATTAAGGAGGACCACCTCCTCCGT
PNN1152   ------------------------------------CATTAAGGAGGACCACCTCCTCCGT
PNN1157   ------------------------------------CATTAAGGAGGACCACCTCCTCCGT
PNN1170   ------------------------------------CATTAAGGAGGACCACCTCCTCCGT
PNN1153   ------------------------------------CATTAAGGAGGACCACCTCCTCCGT
PNN1155   ------------------------------------CATTAAGGAGGACCACCTCCTCCGT
PNN1159   TGGCTGGGAATCACCAATTTTTCTTTGTGGATCAGCATTAAGGAGGACCACCTCCTCCGT
PNN1166   TGGCTGGGAATCACCAATTTTTCTTTGTGGATCAGCATTAAGGAGGACCACCTCCTCCGT
PNN1137   ------------------------------------CATTAAGGAGGACCACCTCCTCCGT
PNN1176   ------------------------------------CATTAAGGAGGACCACCTCCTCCGT
PNN1139   ------------------------------------CATTAAGGAGGACCACCTCCTCCGT
PNN1105   ------------------------------------CATTAAGGAGGACCACCTCCTCCGT
PNN1136   ------------------------------------CATTAAGGAGGACCACCTCCTCCGT
PNN2113   ------------------------------------CATTAAGGAGGACCACCTCCTCCGT
PNN1168   ------------------------------------CATTAAGGAGGACCACCTCCTCCGT
PNN1143   ------------------------------------CATTAAGGAGGACCACCTCCTCCGT
PNN1174   ------------------------------------CATTAAGGAGGACCACCTCCTCCGT
PNN1131   ------------------------------------CATTAAGGAGGACCACCTCCTCCGT
PNN1149   ------------------------------------CATTAAGGAGGACCACCTCCTCCGT
PNN1132   ------------------------------------CATTAAGGAGGACCACCTCCTCCGT
PNN1102   ------------------------------------CATTAAGGAGGACCACCTCCTCCGT
PNN1108   ------------------------------------CATTAAGGAGGACCACCTCCTCCGT
PNN1196   ------------------------------------CATTAAGGAGGACCACCTCCTCCGT
PNN1118   ------------------------------------CATTAAGGAGGACCACCTCCTCCGT
PNN1150   ------------------------------------CATTAAGGAGGACCACCTCCTCCGT
PNN1183   ------------------------------------CATTAAGGAGGACCACCTCCTCCGT
PNN1130   ------------------------------------CATTAAGGAGGACCACCTCCTCCGT
PNN1165   ------------------------------------CATTAAGGAGGACCACCTCCTCCGT
PNN1104   ------------------------------------CATTAAGGAGGACCACCTCCTCCGT
PNN1179   ---------------------------------CCAGCAGAAAGCAGAACATGGCACAG
PNN1103   ------------------------------------CATTAAGGAGGACCACCTCCTCCGT
PNN1101   --------------------------------ACTCCAGTAGAAACCGGAACATGGCACAG
PNN1128   ------------------------------------CATTAAGGAGGACCACCTCCTCCGT
PNN1125   -------------------------------AGGCAGGCAGAAAGCAGAACATGGCACAG
                                         *  *    ** *    *
```

Figure 4b part 13 of 18

```
                     780       790       800       810       820       830       840
PNN1154:     GAGTGCACTCAACTCAACGAAAACGTAAGGATATTACTGAATGAGAACAGAAGGCTGCTG
PNN1152      GAGTGCACTCAACTCAACGAAAACGTAAGGATATTACTGAATGAGAACAGAAGGCTGCTG
PNN1157      GAGTGCACTCAACTCAACGAAAACGTAAGGATATTACTGAATGAGAACAGAAGGCTGCTG
PNN1170      GAGTGCACTCAACTCAACGAAAACGTAAGGATATTACTGAATGAGAACAGAAGGCTGCTG
PNN1153      GAGTGCACTCAACTCAACGAAAACGTAAGGATATTACTGAATGAGAACAGAAGGCTGCTG
PNN1155      GAGTGCACTCAACTCAACGAAAACGTAAGGATATTACTGAATGAGAACAGAAGGCTGATG
PNN1159      GAGTGCACTCAACTCAACGAAAACGTAAGGATATTACTGAATGAGAACAGAAGGCTGCTG
PNN1166      GAGTGCACTCAACTCAACGAAAACGTAAGGATATTACTGAATGAGAACAGAAGGCTGCTG
PNN1137      GAGTGCACTCAACTCCACGAAAACGTAAGGATATTACTGAATGAGAACAGAAGGCTGCTG
PNN1176      GAGTGCACTCAACTCCACGAAAACGTAAGGATATTACTGAATGAGAACAGAAGGCTGCTG
PNN1139      GAGTGCACTCAACTCCACGAAAACGTAAGGATATTACTGAATGAGAACAGAAGGCTGCTG
PNN1105      GACTGCACTCAACTCCACGAAAACGTAAGGATATTACTGAATGAGAACAGAAGGCTGCTG
PNN1136      GAGTGCACTCAACTCAACGAAAACGTAAGGATATTACTGAATGAGAACAGAAGGCTGCTG
PNN1113      GAGTGCACTCAACTCCACGAAAACGTAAGGATATTACTGAATGAGAACAGAAGGCTGCTG
PNN1168      GAGTGCACTCAACTCCACGAAAATGTAAGGATATTACTGAATGAGAACAGAAGGCTGCTG
PNN1143      GAGTGCACTCAACTCAACGAAAAGTAAGGATATTACTGAATGAGAACAGAAGGCTGCTG
PNN1174      GAGTGCACTCAACTCAACGAAAACGTAAGGATATTACTGAATGAGAACAGAAGGCTGCTG
PNN1131      GAGTGCACTCAACTCAACGAAAACGTAAGGATATTACTGAATGAGAACAGAAGGCTGCTG
PNN1149      GAGTGCACTCAACTCAACGAAAACGTAAGGATATTACTGAATGAGAACAGAAGGCTGCTG
PNN1132      GAGTGCACTCAACTCAACGAAAACGTAAGGATATTACTGAATGAGAACAGAAGGCTGCTG
PNN1102      GAGTGCACTCAACTCCACGAAAACGTAAGGATATTACTGAATGAGAACAGAAGGCTGCTG
PNN1108      GAGTGCACTCAACTCCACGAAAATGTAAGGATATTACTGAATGAGAACAGAAGGCTGCTG
PNN1196      GAGTGCACTCAACTCCACGAAAACGTAAGGATATTACTGAATGAGAACAGAAGGCTGCTG
PNN1118      GAGTGCACTCAACTCCACGAAAACGTAAGGATATTACTGAATGAGAACAGAAGGCTGCTG
PNN1150      GAGTGCACTCAACTCCACGAAAACGTAAGGATATTACTGAATGAGAACAGAAGGCTGCTG
PNN1183      GAGTGCACTCAACTCCACGAAAATGTAAGGATATTACTGAATGAGAACAGAAGGCTGCTG
PNN1130      GAGTGCACTCAACTCAACGAAAACGTAAGGATATTACTGAATGAGAACAGAAGGCTGCTG
PNN1165      GAGTGCACTCAACTCCACGAAAACGTAAGGATATTACTGAATGAGAACAGAAGGCTGCTG
PNN1104      GAGTGCACTCAACTCCACGAAAACGTAAGGATATTACTGAATGAGAAC-GAAGGCTGCTG
PNN1179      ACCAGGACATGATCTCCCTCAAAGAGAAG--TGCTGGAGGAAGAGCACTGAGTG-TGCA-
PNN1103      GAGTGCACTCAACTCAGCGAAAAGTAAGGATATTACTGAATGAGAACAGAAAGCTGCTA
PNN1101      ACCACGACATGATCTCCCTCAAAGAGAAG--TGCTGGAGGAAGAGCACTGAGTG-TGCA-
PNN1128      GAGTGCACTCAACTCCACGAAAACGTAAGGATATTACTGAATGAGAACAGAAGGCTGCTG
PNN1125      ACCAGGACATGATCTCCCTCAAAGAGAAG--TGCTGGAGGAAGAGCACTGAGTG-TGCA-
              **  *      *  ***  ***  *   *  * *** **  **    * **
```

Figure 4b part 14 of 18

```
                    840       850       860       870       880       890       900
PNN1154    GTGGAGCAGGCTGGC-CATAAGTGTCCTGTGGGGAAGAAAAGAGGTTCTCTGAGGAAGCC
PNN1152    GTGGAGCAGGCTGGC-TATAAGTGTCCTGTGGGGAAGAAAAGAGGTTCTCTGAGGAGGCC
PNN1157    GTGGAGCAGGCTGGC-CATAAGTGTCCTGTGGGGAAGAAAAGAGGTTCTCTGAGGAGGCC
PNN1170    GTGGAGCAGGCTGGC-CATAAGTGTCCTGTGGGAAGAAAAGAGGTTCTCTGAGGAGGCC
PNN1153    GTGGAGCAGGCTGGC-CATAAGTGTCCTGTGGGGAAGAAAAGAGGTTCTCTGAGGAGGCC
PNN1155    GTGGAGCAGGCTGGC-CATAAGTGTCCTGTGGGAAGAAAAGAGGTTCTCTGAGGAGGCC
PNN1159    GTGGAGCAGGCTGGC-CATAAGTGTCCTGTGGGGAAGAAAAGAGGTTCTCTGAGGAGGCC
PNN1166    GTGGAGCAGGCTGGC-CATAAGTGTCCTGTGGGGAAGAAAAGAGGTTCTCTGAGGAGGCC
PNN1137    GTGGAGCAGGCTGGC-CACAAGTGTCCTGTGGGGAAGAAAAGAGGTTCTCTGAGGAGGCC
PNN1176    GTGGAGCAGGCTGGC-CACAAGTGTCCTGTGGGGAAGAAAAGAGGTTCTCTGAGGAGGCC
PNN1139    GTGGAGCAGGCTGGC-CACAAGTGTCCTGTGGGGAAGAAAAGAGGTTCTCTGAGGAGGCC
PNN1105    GTGGAGCAGGCTGGC-CACAAGTGTCCTGTGGGGAAGAAAAGAGGTTCTCTGAGGAGGCC
PNN1136    GTGGAGCAGGCTGGC-CATAAGTGTCCTGTGGGGAAGAAAAGAGGTTCTGTGAGGAGGCC
PNN1113    GTGGAGCAGGCTGGC-CACAAGTGTCCTGTGGGGAAGAAAAGAGGTTCTCTGAGGATGCC
PNN1168    GTGGAGCAGGCTGGC-CACAAGTGTCCTGTGGGGAAGAAAAGAGGTTCTCTGAGGAGGCC
PNN1143    GTGGAGCAGGCTGGC-CATAAGTGTCCTGTGGGGAAGAAAAGAGGTTCTCTGAGGAAGCC
PNN1174    GTGGAGCAGGCTGGC-TATAAGTGTCCTGTGGGGAAGAAAAGAGGTTCTCTGAGGAGGCC
PNN1131    GTGGAGCAGGCTGGC-CATAAGTGTCCTGTGGGGAAGAAAAGAGGTTCTCTGAGGAGGCC
PNN1149    GTGGAGCAGTCTGGC-CATAAGTGTCCTGTGGGGAAGAAAAGAGGTTCTCTGAGGAGGCC
PNN1132    GTGGAGCAGGCTGGC-CATAAGTGTCCTGTGGGGAAGAAAAGAGGTTCTCTGAGGAGGCC
PNN1102    GTGGAGCAGGCTGGC-CACAAGTGTCCTGTGGGGAAGAAAAGAGGTTCTCTGAGGAGGCC
PNN1108    GTGGATCAGGCTGGC-CACAAGTGTCCTGTGGGGAAGAAAAGAGGTTCTCTGAGGAGGCC
PNN1196    GTGGAGCAGGCTGGC-CACAAGTGTCCTGTGGGGAAGAAAAGAGGTTCTCTGAGGAGGCC
PNN1118    GTGGAGCAGGCTGGC-CACAAGTGTCCTGTGGGGAAGAAAAGAGGTTCTCTGAGGAGGCC
PNN1150    GTGGAGCAGGCTGGC-CACAAGTGTCCTGTGGGGAAGAAAAGAGGTTCTCTGAGGAGGCC
PNN1183    GTGGAGCAGGCTGGC-CACAAGTGTCCTGTGGGGAAGAAAAGAGGTTCTCTGAGGAGGCC
PNN1130    GTGGAGCAGGCTGGC-CATAAGTGTCCTGTGGGGAAGAAAAGAGGTTCTCTGAGGAGGCC
PNN1165    GTGGAGCAGGCTGGC-CACAAGTGTCCTGTGGGGAAGAAAA-AGGTTCTCTGAGGAGGCC
PNN1104    GTGGAGCAGGCTGGC-CACAAGTGTCCTGTGGGGAAGAAAAGAGGTTCTCTGAGGAGGCG
PNN1179    ------------------------------------------------------------
PNN1103    GTGGAGCAGGCTGGAACGCAATTGTCTCATGGGAAGAAAAGAGGTTCTGTGAGGAGGCC
PNN1101    ------------------------------------------------------------
PNN1128    GTGGAGCAGGCTGGC-CACAAGTGTCCTGTGGG-AAGAAAAGTGGTTCTCTGAGGAGGCC
PNN1125    ------------------------------------------------------------
```

Figure 4b part 15 of 18

```
          '900       910       920       930       940       950       960
PNN1154   AGCAAGAACATCTGTGTCCCAAGTGCCAAGGAACAGCAG-----TGTGAAATAGTCCAGC
PNN1152   AGCAAGAACATCTGTGTCCCAAGTGCCAAGGAACAGCAG-----TGTGAAATAGTCCAGC
PNN1157   AGCAAGAACATCTGTGTCCCAAGTGCCAAGGAACAGCAG-----TGTGATATAGTCCAGC
PNN1170   AGGAAGTACATCTGTGTCCCAAGTGCCAAGGAACAGCAG-----TGTGATATAGTCCAGC
PNN1153   AGCAAGAACATCTGTGTCCCAAGTGCCAAGGAACAGCAG-----TGTGAAATAGTCCAAC
PNN1155   AGCAAGAACATCTGTGTCCCAAGTGCCAAGGAACAGCAG-----T----------CCAGC
PNN1159   AGCAAGAACATCTGTGTCCCAAGTGCCAAGGAACAGCAG-----TGTGAAATAGTCCAAC
PNN1166   AGGAAGTACATCTGTGTCCCAAGTGCCAAGGAACAGCAG-----TGTGATATAGTCCAGC
PNN1137   AGCAAGAACATCTGTGTCCCAAGTGCCAAGGAACAGCAG---------------TCCAGC
PNN1176   AGCAAGAACATCTGTGTCCCAAGTGCCAAGGAACAGCAGT---------------CCAGC
PNN1139   AGCAAGAACATCTGTGTCCCAAGTGCCAAGGAACAGCAG---------------TCCAGC
PNN1105   AGCAAGAACATCTGTGTCCCAAGTGCCAAGGAACAGCAGT---------------CCAGC
PNN1136   AGCAAGAACATCTGTGTCCCAAGTGCCAAGGAACAGCAG---------------TCCAGC
PNN1113   AGATAGAACATCTGTGTCCCAAGTGCCAAGGAACAGCAGT---------------CCAGC
PNN1168   AGCAAGAACATCTGTGTCCCAAGTCCCAAGGAACAGCAG-----T----------CCAGC
PNN1143   AGCAAGAACATCTGTGTCCCAAGTGCCAAGGAACAGCAG-----TGTGAAATAGTCCAGC
PNN1174   AGCAAGAACATCTGTGTCCCAAGTGCCAAGGAACAGCAG-----TGTGAAATAGTCCAGC
PNN1131   AGCAAGAACATCTGTGTCCCAAGTGCCAAGGAACAGCAG-----TGTGATATAGTCCAGC
PNN1149   AGCAAGAACATCTGTGTCCCAAGTGCCAAGGAACAGCAG-----TGTGATATAGTCCAGC
PNN1132   AGCAAGAACATCTGTGTCCCAAGTGCCAAGGAACAGCAGCTAAGTGTGAAATAGTCCAGC
PNN1102   AGCAAGAACATCTGTGCCTCAAGTGCCAAGGAGCAGCAG-----TGTGATATAGTCCAGC
PNN1108   AGCAAGAACATCTGTGTCCCAAGTGCCAAGGAACACCAG-----TGTGAAATAGTCCAGC
PNN1196   AGCAAGAACATCTGTGTCCCAAGTGCCAAGGAACACCAGTG-----TGAAATAGTCCAGC
PNN1118   AGCAAGAACATCTGTGTCCCAAGTGCCAAGGAACACCAG-----TGTGATATAGTCCAGC
PNN1150   AGCAAGAACATCTGTGTCCCAAGTGCCAAGGAACACCAG-----TGTGATATAGTCCAGC
PNN1183   AGCAAGAACATCTGTGTCCCAAGTCCCAAGGAACAGCAG-----TGTGAAATAGTCCAGC
PNN1130   A-CAAGAACATCTGTGTCCCAAGTGCCAAGGAACAGCAG-----TGTGATATAGTCCAGC
PNN1165   AGCAAGAACATCTGTGTCCCAAGTGCCAAGGAACACCAG-----TGTGATATAGTCTAGC
PNN1104   AGCAAGAACATCTGTGTCCCAAGTGCCAAGGAACAGCAGT---------------CCAGC
PNN1179   ------------------------------------------------------------
PNN1103   AGCAAGAACATCTGTGCCTCAAGTGCCAAGGAGCAGCAG-----TGTGTAA-ACTCCAGT
PNN1101   ------------------------------------------------------------
PNN1128   AGCAAGAACATCTGTGTCCCAAGTGCCAAGGAACAGCAG-----TGTGAAATAGTCCAGC
PNN1125   ------------------------------------------------------------
```

Figure 4b part 16 of 18

```
             960       970       980       990      1000      1010      1020
PNN1154  AGAAAGCAGAACACGGCACAGACCACGACATGATCTCCCTCAAAGAGAA-GTGCTGGAGG
PNN1152  TGAAAGCAGAACATGGCACAGACCAGGACATGATCTCCCTCAAAGAGAA-GTGCTGGAGG
PNN1157  AGAAAGCAGAACATGGCACAGACCACGACATGATCTCCCTCAAAGAGAA-GTGCTGGAGG
PNN1170  AGAAAGCAGAACATGGCACAGACCACGGCATGATCTCCCTCAAAGAGAA-GTGCTGGAGG
PNN1153  AGAAAGCAGAACATGGCACAGACCACGACATGATCTCCCTCAAAGAGAA-GTGCTGGAGG
PNN1155  AGAAAGCAGAACATGGCACAGACCAGGAAATGATCTCCCTCAAAGAGAA-GTGCTGGAGG
PNN1159  AGAAAGCAGAACATGGCACAGACCACGACATGATCTCCCTC-------------------
PNN1166  AGAAAGCAGAACATGGCACAGACCACGACATGATCTCCCTCAAAGAGAA-GTGCTGGAGG
PNN1137  AGAAAGCAGAACATGGCACTGACCACGACATGATCTCCCTCAAAGAGAA-GTGCTGGAGG
PNN1176  AGAAAGCAGAACATGGCACAGACCAGGACATGATCTCCCTCAAAGAGAA-GTGCTGGAGG
PNN1139  AGAAAGCAGAACATGGCACAGACCAGGACATGATCTCCCTCAAAGAGAA-GTGCTGGAGG
PNN1105  AGAAAGCAGAACATGGCACAGACCAGGACATGATCTCCCTCAAAGAGAA-GTGCTGGAGG
PNN1136  AGAAAGCAGAACATGGCACAGACCAGGACATGATCTCCCTCAAAGAGAA-GTGCTGGAGG
PNN1113  AGAAAGCAGAACATGGCACAGACCAGGACATGATCTCCCTCAAAGAGAA-GTGCTGGAGG
PNN1168  AGAAAGCAGAACATGGCACAGACCAGGACATGATCTCCCTCAAAGAGAA-GTGCTGGAGG
PNN1143  AGAAAGCAGAACATGGCACTGACCACGACATGATCTCCCTCAAAGAGAA-GTGCTGGAGG
PNN1174  TGAAAGCAGAACATGGCACAGACCAGGACATGATCTCCCTCAAAGAGAA-GTGCTGGAGG
PNN1131  AGAAAGCAGAACATGGCACAGACCACGACATGATCTCCCTCAAAGAGAA-GTGCTGGAGG
PNN1149  AGAAAGCAGAACATGGCACAGACCACGACATGATCTCCCTCAAAGAGAA-GTGCTGGAGG
PNN1132  TGAAAGCAGAACATGGCACAGACCAGGACATGATCTCCCTCAAAGAGAA-GTGCTGGAGG
PNN1102  AGAAAGCAGAACATGGCACAGACCACGACATGATCTCCCTCAAAGAGAA-GTGCTGGAGG
PNN1108  AGAAAGCAGAACATGGCACAGACCAGGACATGATCTCCCTCAAAGAGAA-GTGCTGGAGG
PNN1196  AGAAAGCAGAACATGGCACAGACCAGGACATGATCTCCCTCAAAGAGAA-GTGCTGGAGG
PNN1118  AGAAAGCAGAACATGGCACAGACCACGACATGATCTCCCTCAAAGAGAA-GTGCTGGAGG
PNN1150  AGAAAGCAGAACATGGCACAGACCATGATCTCCTCCCTCAAAGAGAA-GTGCTGGAGG
PNN1183  AGAAAGCAGAACATGGCACAGACCAGGACATGATCTCCCTCAAAGAGAA-GTGCTGGAGG
PNN1130  AGAAAGCAGAACATGGCACAGACCACGACATGATCTCCCTCAAAGAGAA-GTGCTGGAGG
PNN1165  AGAAAGCAGAACATGGCACAGACCACGACATGATCTCCCACAAAGAGAA-GTGCTGGAGG
PNN1104  AGAAAGCAGAACATGGCACAGACCAGGACATGATCTCCCTCAAAGAGAA-GTGCTGGAGG
PNN1179  ------------------------------------------------------------
PNN1103  AGAAACCGGAACATGGCACAGACCACGACATGATCTCCCTCAAAGAGAA-GTGCTGGAGG
PNN1101  ------------------------------------------------------------
PNN1128  AGAAAGCAGAACATGGCACAGACCAGGACATGATCTCCCTCAAAGAGAA-GTGCTGGAGG
PNN1125  ------------------------------------------------------------
```

Figure 4b part 17 of 18

```
                1020      1030      1038
PNN1154    AAGAGCACTGAGTGTGCA
PNN1152    AAGAGCACTGAGTGTGCA
PNN1157    AAGAGCACTGAGTGTGCA
PNN1170    AAGAGCACTGAGTGTGCA
PNN1153    AAGAGCACTGAGTGTGCA
PNN1155    AAGAGCACTGAGTGTGCA
PNN1159    ------------------
PNN1166    AAGAGCACTGAGTGTGCA
PNN1137    AAGAGCACTGAGTGTGCA
PNN1176    AAGAGCACTGAGTGTGCA
PNN1139    AAGAGCACTGAGTGTGCA
PNN1105    AAGAGCACTGAGTGTGCA
PNN1136    AAGAGCACTGAGTGTGCA
PNN1113    AAGAGCACTGAGTGTGCA
PNN1168    AAGAGCACTGAGTGTGCA
PNN1143    AAGAGCACTGAGTGTGCA
PNN1174    AAGAGCACTGAGTGTGCA
PNN1131    AAGAGCACTGAGTGTGCA
PNN1149    AAGAGCACTGAGTGTGCA
PNN1132    AAGAGCACTGAGTGTGCA
PNN1102    AAGAGCACTGAGTGTGCA
PNN1108    AAGAGCACTGAGTGTGCA
PNN1196    AAGAGCACTGAGTGTGCA
PNN1118    AAGAGCACTGAGTGTGCA
PNN1150    AAGAGCACTGAGTGTGCA
PNN1183    AAGAGCACTGAGTGTGCA
PNN1130    AAGAGCACTGAGTGTGCA
PNN1165    AAGAGCACTGAGTGTGCA
PNN1104    AAGAGCACTGAGTGTGCA
PNN1179    ------------------
PNN1103    AGGAGCACTGAGTGTGCA
PNN1101    ------------------
PNN1128    AAGAGCACTGAGTGTGCA
PNN1125    ------------------
```

Figure 4b part 18 of 18

SEQUENCE LISTING

<160> NUMBER OF SEQ ID NOS: 96

<210> SEQ ID NO 1
<211> LENGTH: 1992
<212> TYPE: DNA
<213> ORGANISM: mouse

<400> SEQUENCE: 1

```
ggcttggatc ccagagccca gcctgggagg aaccggggct cctggtgtac catcatcatc      60
cccaacactc ctgttcagaa gatgggtgag gaaagtggaa agtctaacca gtcagccgat     120
gaccagtggg aaaaatgagc tacaagatca cctgatcttc atcagtgaga aagctttgca     180
caagagggtc tgctagaaat acttcaaccc aaaattccaa aatgaccaag aagagatcaa     240
aaataaatga actagaagaa ctgaaattgg atatgaggaa gatcagcaat gacatggagg     300
aaatgtgtgg aatcctgaac ctttacatgt atgaggattt gaactacagg atgaacactg     360
aattcaacat cattaaatca caacatgaga agacaatgtt ggatatgaat aaaatgatcc     420
agtccataat tggttccatg cagtactcca aggaactgat agaagataac tattcctaca     480
gcattaagga ggaccacctc ctccgtgagt gcactcaact caacgaaaac gtaaggatat     540
tactgaatga gaacagaagg ctgctggtgg agcaggctgg ccataagtgt cctgtgggga     600
agaaaagagg ttctgtgagg aggccagcaa gaacatctgt gtcccaagtg ccaaggaaca     660
gcagtgtgat atagtccagc agaaagcaga acatggcaca gaccacgaca tgatctccct     720
caaagagaag tgctggagga agagcactga gtgtgcacag gaaatacacc actgttgcct     780
ctcatcccta ataaccatgg ctgtaatggg ctgtatgctc ctctttatt ttgtttcttt     840
ggtatgaaca ggccttaatt tcatctagcc tctggcccag gaagagtgca catttaaagg     900
gactcagaga aatgctgaga cacatcaaga gctgctgggc atccaggaag attctgagag     960
tttatattta tcttttcctg atgggtcatc atcaataatt acatggagat cagtcaacaa    1020
aattgtaaaa ccttggatcc aagtctacaa catgtgttct gctttgactt gggaggccat    1080
atccttcaga cccacactcc aaaaggagag tgttgcttaa atttctcctg caaagtttgt    1140
tacctccagg aactactttt ctactaagtt gccaaggaca gccacaggct gtaagtctgt    1200
gctacaaaat gagcagacta agaattttgc tttgcacaat ttttgtggtt tgattttggt    1260
ttgagttttg attagtttag ttatttgttt tttcttgttt tcattcaaag ttttgttatt    1320
tattggttat ttattgttct tttaattaat ttgatatttt gataaggtta tacacagtac    1380
atattgactg tcagctttca gttacaattg agtacattgc attttttctt atgactaaca    1440
cagtgatctc caactcttca ctctaagagc cttgttattt cagttgtgat catgaaatcc    1500
cacagatatc agacccagat ggatctctgc actcttcatg ggacttgggc tccatagttt    1560
cttctgagcc ggacttaact acaaagtcct tcatacattc agtatggaga gttttctaa    1620
ctgtctgtat aggaacttaa tgatggaaaa cttacccatg ctgcatcgtt gctgtcaaat    1680
atttagctac tgtgaaaatc ctgtggatta tggtgttgaa cgcattaatg gcaaatacat    1740
cagtatttct gtaatagctc tcattaaatc aaagcatagt ctaagggaat aaaaagctgt    1800
cagaaaacac agcagtgtat gcttctgcgt tccttcaaat atacaatcac tggtaattgc    1860
aagtggtttc tgtggggtc cttcaatgtt cattttatta ctttatgatt cacctgtgtc    1920
tgccaaaaaa catcactcaa aaacaatgaa gattgtaatt aggtatcatc ctataaaatc    1980
ctaacaaatg cc                                                        1992
```

<210> SEQ ID NO 2
<211> LENGTH: 453
<212> TYPE: DNA
<213> ORGANISM: Mouse

<400> SEQUENCE: 2

```
atgaccaaga agagatcaaa aataaatgaa ctagaagaac tgaaattgga tatgaggaag      60
atcagcaatg acatggagga aatgtgtgga atcctgaacc tttacatgta tgaggatttg     120
```

```
aactacagga tgaacactga attcaacatc attaaatcac aacatgagaa gacaatgttg    180
gatatgaata aaatgatcca gtccataatt ggttccatgc agtactccaa ggaactgata    240
gaagataact attcctacag cattaaggag gaccacctcc tccgtgagtg cactcaactc    300
aacgaaaacg taaggatatt actgaatgag aacagaaggc tgctggtgga gcaggctggc    360
cataagtgtc ctgtggggaa gaaaagaggt tctgtgagga ggccagcaag aacatctgtg    420
tcccaagtgc caaggaacag cagtgtgata tag                                 453
```

<210> SEQ ID NO 3
<211> LENGTH: 150
<212> TYPE: PRT
<213> ORGANISM: mouse

<400> SEQUENCE: 3

```
Met Thr Lys Lys Arg Ser Lys Ile Asn Glu Leu Glu Glu Leu Lys Leu
1               5                   10                  15

Asp Met Arg Lys Ile Ser Asn Asp Met Glu Glu Met Cys Gly Ile Leu
            20                  25                  30

Asn Leu Tyr Met Tyr Glu Asp Leu Asn Tyr Arg Met Asn Thr Glu Phe
        35                  40                  45

Asn Ile Ile Lys Ser Gln His Glu Lys Thr Met Leu Asp Met Asn Lys
    50                  55                  60

Met Ile Gln Ser Ile Ile Gly Ser Met Gln Tyr Ser Lys Glu Leu Ile
65                  70                  75                  80

Glu Asp Asn Tyr Ser Tyr Ser Ile Lys Glu Asp His Leu Leu Arg Glu
                85                  90                  95

Cys Thr Gln Leu Asn Glu Asn Val Arg Ile Leu Leu Asn Glu Asn Arg
            100                 105                 110

Arg Leu Leu Val Glu Gln Ala Gly His Lys Cys Pro Val Gly Lys Lys
        115                 120                 125

Arg Gly Ser Val Arg Arg Pro Ala Arg Thr Ser Val Ser Gln Val Pro
    130                 135                 140

Arg Asn Ser Ser Val Ile
145                 150
```

<210> SEQ ID NO 4
<211> LENGTH: 205
<212> TYPE: PRT
<213> ORGANISM: Mouse

<400> SEQUENCE: 4

```
Met Phe Ser Trp Leu Leu Arg Leu Phe Gln Lys Glu Asn Gly Asp Glu
1               5                   10                  15

Gly Glu Thr Arg Pro Thr Glu Lys Glu Gly Ile Leu Ser His Glu
            20                  25                  30

Lys Gly Arg Arg Lys Ser Phe Trp Arg Arg His Arg Ser Ala Arg Asn
        35                  40                  45

Thr Ser Thr Gln Asn Ser Lys Met Thr Lys Arg Ser Lys Ile Asn
    50                  55                  60

Glu Leu Glu Glu Leu Lys Leu Asp Met Arg Lys Ile Ser Asn Asp Met
65                  70                  75                  80

Glu Glu Met Cys Gly Ile Leu Asn Leu Tyr Met Tyr Glu Asp Leu Asn
                85                  90                  95

Tyr Arg Met Asn Thr Glu Phe Asn Ile Ile Lys Ser Gln His Glu Lys
            100                 105                 110
```

```
Thr Met Leu Asp Met Asn Lys Met Ile Gln Ser Ile Ile Gly Ser Met
        115                 120                 125

Gln Tyr Ser Lys Glu Leu Ile Glu Asp Asn Tyr Ser Tyr Ser Ile Lys
        130                 135                 140

Glu Asp His Leu Leu Arg Glu Cys Thr Gln Leu Asn Glu Asn Val Arg
145                 150                 155                 160

Ile Leu Leu Asn Glu Asn Arg Arg Leu Leu Val Glu Gln Ala Gly His
                165                 170                 175

Lys Cys Pro Val Gly Lys Lys Arg Gly Ser Leu Arg Lys Pro Ala Arg
                180                 185                 190

Thr Ser Val Ser Gln Val Pro Arg Asn Ser Ser Val Lys
        195                 200                 205

<210> SEQ ID NO 5
<211> LENGTH: 205
<212> TYPE: PRT
<213> ORGANISM: Mouse

<400> SEQUENCE: 5

Met Phe Ser Trp Leu Leu Arg Leu Phe Gln Lys Glu Asn Gly Asp Glu
1               5                   10                  15

Gly Glu Thr Arg Pro Thr Glu Lys Glu Glu Gly Ile Leu Ser His Glu
            20                  25                  30

Lys Gly Arg Arg Lys Ser Phe Trp Arg Arg His Arg Ser Ala Arg Asn
        35                  40                  45

Thr Ser Thr Gln Asn Ser Lys Met Thr Lys Lys Arg Ser Lys Ile Asn
    50                  55                  60

Glu Leu Glu Glu Leu Lys Leu Asp Met Arg Lys Ile Ser Asn Asp Met
65                  70                  75                  80

Glu Glu Met Cys Gly Ile Leu Asn Leu Tyr Met Tyr Glu Asp Leu Asn
                85                  90                  95

Tyr Arg Met Asn Thr Glu Phe Asn Ile Ile Lys Ser Gln His Glu Lys
                100                 105                 110

Thr Met Leu Asp Met Asn Lys Met Ile Gln Ser Ile Ile Gly Ser Met
        115                 120                 125

Gln Tyr Ser Lys Glu Leu Ile Glu Asp Asn Tyr Ser Tyr Ser Ile Lys
        130                 135                 140

Glu Asp His Leu Leu Arg Glu Cys Thr Gln Leu Asn Glu Asn Val Arg
145                 150                 155                 160

Ile Leu Leu Asn Glu Asn Arg Arg Leu Leu Val Glu Gln Ala Gly Tyr
                165                 170                 175

Lys Cys Pro Val Gly Lys Arg Gly Ser Leu Arg Arg Pro Ala Arg
                180                 185                 190

Thr Ser Val Ser Gln Val Pro Arg Asn Ser Ser Val Lys
        195                 200                 205

<210> SEQ ID NO 6
<211> LENGTH: 205
<212> TYPE: PRT
<213> ORGANISM: Mouse

<400> SEQUENCE: 6

Met Phe Ser Trp Leu Leu Arg Leu Phe Gln Lys Glu Asn Gly Asp Glu
1               5                   10                  15

Gly Glu Thr Arg Pro Thr Glu Lys Glu Glu Gly Ile Leu Ser His Glu
            20                  25                  30
```

Lys Gly Arg Arg Lys Ser Phe Trp Arg Arg His Arg Ser Ala Arg Asn
            35                  40                  45

Thr Ser Thr Gln Asn Ser Lys Met Thr Lys Lys Arg Ser Lys Ile Asn
        50                  55                  60

Glu Leu Glu Glu Leu Lys Leu Asp Met Arg Lys Ile Ser Asn Asp Met
65                  70                  75                  80

Glu Glu Met Cys Gly Ile Leu Asn Leu Tyr Met Tyr Glu Asp Leu Asn
                85                  90                  95

Tyr Arg Met Asn Thr Glu Phe Asn Ile Ile Lys Ser Gln His Glu Lys
                100                 105                 110

Thr Met Leu Asp Met Asn Lys Met Ile Gln Ser Ile Ile Gly Ser Met
            115                 120                 125

Gln Tyr Ser Lys Glu Leu Ile Glu Asp Asn Tyr Ser Tyr Ser Ile Lys
        130                 135                 140

Glu Asp His Leu Leu Arg Glu Cys Thr Gln Leu Asn Glu Asn Val Arg
145                 150                 155                 160

Ile Leu Leu Asn Glu Asn Arg Arg Leu Leu Val Glu Gln Ala Gly His
                165                 170                 175

Lys Cys Pro Val Gly Lys Lys Arg Gly Ser Leu Arg Arg Pro Ala Arg
                180                 185                 190

Thr Ser Val Ser Gln Val Pro Arg Asn Ser Ser Val Ile
            195                 200                 205

<210> SEQ ID NO 7
<211> LENGTH: 205
<212> TYPE: PRT
<213> ORGANISM: Mouse

<400> SEQUENCE: 7

Met Phe Ser Trp Leu Leu Arg Leu Phe Gln Lys Glu Asn Gly Asp Glu
1               5                   10                  15

Gly Glu Thr Arg Pro Thr Glu Lys Glu Glu Gly Ile Leu Ser His Glu
            20                  25                  30

Lys Gly Arg Arg Lys Ser Phe Trp Arg Arg His Arg Ser Ala Arg Asn
        35                  40                  45

Thr Ser Thr Gln Asn Ser Lys Met Thr Lys Lys Arg Ser Lys Ile Asn
    50                  55                  60

Glu Leu Glu Glu Leu Lys Leu Asp Met Arg Lys Ile Ser Asn Asp Met
65                  70                  75                  80

Glu Glu Met Cys Gly Ile Leu Asn Leu Tyr Met Tyr Glu Asp Leu Asn
                85                  90                  95

Tyr Arg Met Asn Thr Glu Phe Asn Ile Ile Lys Ser Gln His Glu Lys
                100                 105                 110

Thr Met Leu Asp Met Asn Lys Met Ile Gln Ser Ile Ile Gly Ser Met
            115                 120                 125

Gln Tyr Ser Lys Glu Leu Ile Glu Asp Asn Tyr Ser Tyr Ser Ile Lys
        130                 135                 140

Glu Asp His Leu Leu Arg Glu Cys Thr Gln Leu Asn Glu Asn Val Arg
145                 150                 155                 160

Ile Leu Leu Asn Glu Asn Arg Arg Leu Leu Val Glu Gln Ala Gly His
                165                 170                 175

Lys Cys Pro Val Gly Lys Lys Arg Gly Ser Leu Arg Arg Pro Gly Ser
                180                 185                 190

Thr Ser Val Ser Gln Val Pro Arg Asn Ser Ser Val Ile

```
                 195                 200                 205

<210> SEQ ID NO 8
<211> LENGTH: 205
<212> TYPE: PRT
<213> ORGANISM: Mouse

<400> SEQUENCE: 8

Met Phe Ser Trp Leu Leu Arg Leu Phe Gln Lys Glu Thr Gly Asp Glu
1               5                   10                  15

Gly Glu Thr Arg Pro Thr Glu Lys Glu Gly Ile Leu Ser His Glu
            20                  25                  30

Lys Gly Arg Arg Lys Ser Phe Trp Arg Arg His Arg Ser Ala Arg Asn
        35                  40                  45

Thr Ser Thr Gln Asn Ser Lys Met Thr Lys Lys Arg Ser Lys Ile Asn
    50                  55                  60

Glu Leu Glu Glu Leu Lys Leu Asp Met Arg Lys Ile Ser Asn Asp Met
65                  70                  75                  80

Glu Glu Met Cys Gly Ile Leu Asn Leu Tyr Met Tyr Glu Asp Leu Asn
                85                  90                  95

Tyr Arg Met Asn Thr Glu Phe Asn Ile Ile Lys Ser Gln His Glu Lys
            100                 105                 110

Thr Met Leu Asp Met Asn Lys Met Ile Gln Ser Ile Ile Gly Ser Met
        115                 120                 125

Gln Tyr Ser Lys Glu Leu Ile Glu Asp Asn Tyr Ser Tyr Ser Ile Lys
    130                 135                 140

Glu Asp His Leu Leu Arg Glu Cys Thr Gln Leu Asn Glu Asn Val Arg
145                 150                 155                 160

Ile Leu Leu Asn Glu Asn Arg Arg Leu Leu Val Glu Gln Ala Gly His
                165                 170                 175

Lys Cys Pro Val Gly Lys Lys Arg Gly Ser Leu Arg Arg Pro Ala Arg
            180                 185                 190

Thr Ser Val Ser Gln Val Pro Arg Asn Ser Ser Val Lys
        195                 200                 205

<210> SEQ ID NO 9
<211> LENGTH: 227
<212> TYPE: PRT
<213> ORGANISM: Mouse

<400> SEQUENCE: 9

Met Phe Ser Trp Leu Leu Arg Leu Phe Gln Lys Glu Asn Gly Asp Glu
1               5                   10                  15

Gly Glu Thr Arg Pro Thr Glu Lys Glu Gly Ile Leu Ser His Glu
            20                  25                  30

Lys Gly Arg Arg Lys Ser Phe Trp Arg Arg His Arg Ser Ala Arg Asn
        35                  40                  45

Thr Ser Thr Gln Asn Ser Lys Met Thr Lys Lys Arg Ser Lys Ile Asn
    50                  55                  60

Glu Leu Glu Glu Leu Lys Leu Asp Met Arg Lys Ile Ser Asn Asp Met
65                  70                  75                  80

Glu Glu Met Cys Gly Ile Leu Asn Leu Tyr Met Tyr Glu Asp Leu Asn
                85                  90                  95

Tyr Arg Met Asn Thr Glu Phe Asn Ile Ile Lys Ser Gln His Glu Lys
            100                 105                 110

Thr Met Leu Asp Met Asn Lys Met Ile Gln Ser Ile Ile Gly Ser Met
```

-continued

```
                115                 120                 125
Gln Tyr Ser Met Glu Leu Ile Glu Asp Asn Tyr Ser Tyr Ser Ile Lys
    130                 135                 140

Glu Asp His Leu Leu Arg Glu Cys Thr Gln Leu Asn Glu Asn Val Arg
145                 150                 155                 160

Ile Leu Leu Asn Glu Asn Arg Arg Leu Met Val Glu Gln Ala Gly His
                165                 170                 175

Lys Cys Pro Val Gly Lys Lys Arg Gly Ser Leu Arg Arg Pro Ala Arg
            180                 185                 190

Thr Ser Val Ser Gln Val Pro Arg Asn Ser Ser Pro Ala Glu Ser Arg
            195                 200                 205

Thr Trp His Arg Pro Gly Asn Asp Leu Pro Gln Arg Glu Val Leu Glu
    210                 215                 220

Glu Glu His
225

<210> SEQ ID NO 10
<211> LENGTH: 171
<212> TYPE: PRT
<213> ORGANISM: Mouse

<400> SEQUENCE: 10

Met Phe Ser Trp Leu Leu Arg Leu Phe Gln Lys Glu Thr Gly Asp Glu
1               5                   10                  15

Gly Glu Thr Arg Pro Thr Glu Lys Glu Glu Gly Ile Leu Ser His Glu
            20                  25                  30

Lys Gly Arg Arg Lys Ser Phe Trp Arg Arg His Arg Ser Ala Arg Asn
        35                  40                  45

Thr Ser Thr Gln Asn Ser Lys Met Thr Lys Lys Ser Lys Ile Asn
    50                  55                  60

Glu Leu Glu Glu Leu Lys Leu Asp Met Arg Lys Ile Ser Asn Asp Met
65                  70                  75                  80

Glu Glu Met Cys Gly Ile Leu Asn Leu Tyr Met Tyr Glu Asp Leu Asn
                85                  90                  95

Tyr Arg Met Asn Thr Glu Phe Asn Ile Ile Lys Ser Gln His Glu Lys
            100                 105                 110

Thr Met Leu Asp Met Asn Lys Met Ile Gln Ser Ile Ile Gly Ser Met
        115                 120                 125

Gln Tyr Ser Lys Glu Leu Ile Glu Asp Asn Tyr Ser Tyr Arg Ala Leu
    130                 135                 140

Ala Gly Ile Ile Gly Leu Val Gly Val Ala Ser Gln Trp Asn Leu Ala
145                 150                 155                 160

Gly Asn His Gln Phe Phe Val Asp Gln His
                165                 170

<210> SEQ ID NO 11
<211> LENGTH: 171
<212> TYPE: PRT
<213> ORGANISM: Mouse

<400> SEQUENCE: 11

Met Phe Ser Trp Leu Leu Arg Leu Phe Gln Lys Glu Asn Gly Asp Glu
1               5                   10                  15

Gly Glu Thr Arg Pro Thr Glu Lys Glu Glu Gly Ile Leu Ser His Glu
            20                  25                  30

Lys Gly Arg Arg Lys Ser Phe Trp Arg Arg His Arg Ser Ala Arg Asn
```

```
                 35                  40                  45

Thr Ser Thr Gln Asn Ser Lys Met Thr Lys Arg Ser Lys Ile Asn
         50                  55                  60

Glu Leu Glu Glu Leu Lys Leu Asp Met Arg Lys Ile Ser Asn Asp Met
 65                  70                  75                  80

Glu Glu Met Cys Gly Ile Leu Asn Leu Tyr Met Tyr Glu Asp Leu Asn
                 85                  90                  95

Tyr Arg Met Asn Thr Glu Phe Asn Ile Ile Lys Ser Gln His Glu Lys
                100                 105                 110

Thr Met Leu Asp Met Asn Lys Met Ile Gln Ser Ile Ile Gly Ser Met
                115                 120                 125

Gln Tyr Ser Lys Glu Leu Ile Glu Asp Asn Tyr Ser Tyr Arg Ala Leu
            130                 135                 140

Ala Gly Ile Ile Gly Leu Val Gly Val Ala Ser Gln Trp Asn Leu Ala
145                 150                 155                 160

Gly Asn His Gln Phe Phe Phe Val Asp Gln His
                165                 170

<210> SEQ ID NO 12
<211> LENGTH: 156
<212> TYPE: PRT
<213> ORGANISM: Mouse

<400> SEQUENCE: 12

Met Thr Lys Lys Arg Ser Lys Ile Asn Glu Leu Glu Glu Leu Lys Leu
 1               5                  10                  15

Asp Met Arg Lys Ile Ser Asn Asp Met Glu Glu Met Cys Gly Ile Leu
                20                  25                  30

Asn Leu Tyr Met Tyr Glu Asp Leu Asn Tyr Arg Met Asn Thr Glu Phe
            35                  40                  45

Asn Ile Ile Lys Ser Gln His Glu Lys Thr Met Leu Asp Met Asn Lys
         50                  55                  60

Met Ile Gln Ser Ile Ile Gly Ser Met Gln Tyr Ser Lys Glu Leu Ile
 65                  70                  75                  80

Glu Asp Asn Tyr Ser Tyr Ser Ile Lys Glu Asp His Leu Leu Arg Glu
                85                  90                  95

Cys Thr Gln Leu His Glu Asn Val Arg Ile Leu Leu Asn Glu Asn Arg
                100                 105                 110

Arg Leu Leu Val Glu Gln Ala Gly His Lys Cys Pro Val Gly Lys Lys
            115                 120                 125

Arg Gly Ser Leu Arg Arg Pro Ala Arg Thr Ser Val Ser Gln Val Pro
        130                 135                 140

Arg Asn Ser Ser Pro Ala Glu Ser Arg Thr Trp His
145                 150                 155

<210> SEQ ID NO 13
<211> LENGTH: 172
<212> TYPE: PRT
<213> ORGANISM: Mouse

<400> SEQUENCE: 13

Met Thr Lys Lys Arg Ser Lys Ile Asn Glu Leu Glu Glu Leu Lys Leu
 1               5                  10                  15

Asp Met Arg Lys Ile Ser Asn Asp Met Glu Glu Met Cys Gly Ile Leu
                20                  25                  30

Asn Val Tyr Met Tyr Glu Asp Leu Asn Tyr Arg Met Asn Thr Glu Phe
```

-continued

```
                35                  40                  45
Asn Ile Ile Lys Ser Gln His Glu Lys Thr Met Leu Asp Met Asn Lys
             50                  55                  60
Met Ile Gln Ser Ile Ile Gly Ser Met Gln Tyr Ser Lys Glu Leu Ile
 65                  70                  75                  80
Glu Asp Asn Tyr Ser Tyr Ser Ile Lys Glu Asp His Leu Leu Arg Glu
                 85                  90                  95
Cys Thr Gln Leu His Glu Asn Val Arg Ile Leu Leu Asn Glu Asn Arg
                100                 105                 110
Arg Leu Leu Val Glu Gln Ala Gly His Lys Cys Pro Val Gly Lys Lys
            115                 120                 125
Arg Gly Ser Leu Arg Arg Pro Ala Arg Thr Ser Val Ser Gln Val Pro
        130                 135                 140
Arg Asn Ser Ser Pro Ala Glu Ser Arg Thr Trp His Arg Pro Gly His
145                 150                 155                 160
Asp Leu Pro Gln Arg Glu Val Leu Glu Glu His
                165                 170

<210> SEQ ID NO 14
<211> LENGTH: 172
<212> TYPE: PRT
<213> ORGANISM: Mouse

<400> SEQUENCE: 14

Met Thr Lys Lys Arg Ser Lys Ile Asn Glu Leu Glu Glu Leu Lys Leu
  1               5                  10                  15
Asp Met Arg Lys Ile Ser Asn Asp Ile Glu Glu Met Cys Gly Ile Leu
             20                  25                  30
Asn Leu Tyr Met Tyr Glu Asp Leu Asn Tyr Arg Met Asn Thr Glu Phe
         35                  40                  45
Asn Ile Ile Lys Ser Gln His Glu Lys Thr Met Leu Asp Met Asn Lys
     50                  55                  60
Met Ile Gln Ser Ile Ile Gly Ser Met Gln Tyr Ser Lys Glu Leu Ile
 65                  70                  75                  80
Glu Asp Asn Tyr Ser Tyr Ser Ile Lys Glu Asp His Leu Leu Arg Glu
                 85                  90                  95
Cys Thr Gln Leu His Glu Asn Val Arg Ile Leu Leu Asn Glu Asn Arg
                100                 105                 110
Arg Leu Leu Val Glu Gln Ala Gly His Lys Cys Pro Val Gly Lys Lys
            115                 120                 125
Arg Gly Ser Leu Arg Arg Pro Ala Arg Thr Ser Val Ser Gln Val Pro
        130                 135                 140
Arg Asn Ser Ser Pro Ala Glu Ser Arg Thr Trp His Arg Pro Gly His
145                 150                 155                 160
Asp Leu Pro Gln Arg Glu Val Leu Glu Glu His
                165                 170

<210> SEQ ID NO 15
<211> LENGTH: 172
<212> TYPE: PRT
<213> ORGANISM: Mouse

<400> SEQUENCE: 15

Met Thr Lys Lys Arg Ser Lys Ile Asn Glu Leu Glu Glu Leu Lys Leu
  1               5                  10                  15
Asp Met Arg Lys Ile Ser Asn Asp Met Glu Glu Met Gly Gly Ile Leu
```

-continued

```
                    20                  25                  30
Asn Leu Tyr Met Tyr Glu Asp Leu Asn Tyr Arg Met Asn Thr Glu Phe
                35                  40                  45
Asn Ile Ile Lys Ser Gln His Glu Lys Thr Met Leu Asp Met Asn Lys
             50                  55                  60
Met Ile Gln Ser Ile Ile Gly Ser Met Gln Tyr Ser Lys Glu Leu Ile
 65                  70                  75                  80
Glu Asp Asn Tyr Ser Tyr Ser Ile Lys Glu Asp His Leu Leu Arg Asp
                 85                  90                  95
Cys Thr Gln Leu His Glu Asn Val Arg Ile Leu Leu Asn Glu Asn Arg
            100                 105                 110
Arg Leu Leu Val Glu Gln Ala Gly His Lys Cys Pro Val Gly Lys Lys
            115                 120                 125
Arg Gly Ser Leu Arg Arg Pro Ala Arg Thr Ser Val Ser Gln Val Pro
        130                 135                 140
Arg Asn Ser Ser Pro Ala Glu Ser Arg Thr Trp His Arg Pro Gly His
145                 150                 155                 160
Asp Leu Pro Gln Arg Glu Val Leu Glu Glu His
                165                 170
```

<210> SEQ ID NO 16
<211> LENGTH: 172
<212> TYPE: PRT
<213> ORGANISM: Mouse

<400> SEQUENCE: 16

```
Met Thr Lys Lys Arg Ser Lys Ile Asn Glu Leu Glu Glu Leu Lys Leu
  1               5                  10                  15
Asp Met Arg Lys Ile Ser Asn Asp Met Glu Met Cys Gly Ile Leu
                 20                  25                  30
Asn Leu Tyr Met Tyr Glu Asp Leu Asn Tyr Arg Met Asn Thr Glu Phe
             35                  40                  45
Asn Ile Ile Lys Ser Gln His Glu Lys Thr Met Leu Asp Met Asn Lys
         50                  55                  60
Met Ile Gln Ser Ile Ile Gly Ser Met Gln Tyr Ser Lys Glu Leu Ile
 65                  70                  75                  80
Glu Asp Asn Tyr Ser Tyr Ser Ile Lys Glu Asp His Leu Leu Arg Glu
                 85                  90                  95
Cys Thr Gln Leu Asn Glu Asn Val Arg Ile Leu Leu Asn Glu Asn Arg
            100                 105                 110
Arg Leu Leu Val Glu Gln Ala Gly His Lys Cys Pro Val Gly Lys Lys
            115                 120                 125
Arg Gly Ser Val Arg Arg Pro Ala Arg Thr Ser Val Ser Gln Val Pro
        130                 135                 140
Arg Asn Ser Ser Pro Ala Glu Ser Arg Thr Trp His Arg Pro Gly His
145                 150                 155                 160
Asp Leu Pro Gln Arg Glu Val Leu Glu Glu His
                165                 170
```

<210> SEQ ID NO 17
<211> LENGTH: 172
<212> TYPE: PRT
<213> ORGANISM: Mouse

<400> SEQUENCE: 17

Met Thr Lys Lys Arg Ser Lys Ile Asn Glu Leu Glu Glu Leu Lys Leu

```
                 1               5                  10                 15
Asp Met Arg Lys Ile Ser Asn Asp Met Glu Glu Met Cys Gly Ile Leu
                20                 25                 30

Asn Leu Tyr Met Tyr Glu Asp Leu Asn Tyr Arg Met Asn Thr Glu Phe
                35                 40                 45

Asn Ile Ile Lys Ser Gln His Glu Lys Thr Met Leu Asp Met Asn Lys
                50                 55                 60

Met Ile Gln Ser Ile Ile Gly Ser Met Gln Tyr Ser Lys Glu Leu Ile
65                     70                 75                     80

Glu Asp Asn Tyr Ser Tyr Ser Ile Lys Glu Asp His Leu Leu Arg Glu
                85                 90                 95

Cys Thr Gln Leu His Glu Asn Val Arg Ile Leu Leu Asn Glu Asn Arg
                100                105                110

Arg Leu Leu Val Glu Gln Ala Gly His Lys Cys Pro Val Gly Lys Lys
                115                120                125

Arg Gly Ser Leu Arg Met Pro Asp Arg Thr Ser Val Ser Gln Val Pro
                130                135                140

Arg Asn Ser Ser Pro Ala Glu Ser Arg Thr Trp His Arg Pro Gly His
145                    150                155                    160

Asp Leu Pro Gln Arg Glu Val Leu Glu Glu His
                165                170

<210> SEQ ID NO 18
<211> LENGTH: 172
<212> TYPE: PRT
<213> ORGANISM: Mouse

<400> SEQUENCE: 18

Met Thr Lys Lys Arg Ser Lys Arg Asn Glu Leu Glu Glu Leu Lys Leu
1               5                  10                 15

Asp Met Arg Lys Ile Ser Asn Asp Met Glu Glu Met Cys Gly Ile Leu
                20                 25                 30

Asn Leu Tyr Met Tyr Glu Asp Leu Asn Tyr Arg Met Asn Thr Glu Phe
                35                 40                 45

Asn Ile Ile Lys Ser Gln His Glu Lys Thr Met Leu Asp Met Asn Lys
                50                 55                 60

Met Ile Gln Ser Ile Ile Gly Ser Met Gln Tyr Ser Lys Glu Leu Ile
65                     70                 75                     80

Glu Asp Asn Tyr Ser Tyr Ser Ile Lys Glu Asp His Leu Leu Arg Glu
                85                 90                 95

Cys Thr Gln Leu His Glu Asn Val Arg Ile Leu Leu Asn Glu Asn Arg
                100                105                110

Arg Leu Leu Val Glu Gln Ala Gly His Lys Cys Pro Val Gly Lys Lys
                115                120                125

Arg Gly Ser Leu Arg Arg Pro Ala Arg Thr Ser Val Ser Gln Val Pro
                130                135                140

Arg Asn Ser Ser Pro Ala Glu Ser Arg Thr Trp His Arg Pro Gly His
145                    150                155                    160

Asp Leu Pro Gln Arg Glu Val Leu Glu Glu His
                165                170

<210> SEQ ID NO 19
<211> LENGTH: 150
<212> TYPE: PRT
<213> ORGANISM: Mouse
```

```
<400> SEQUENCE: 19

Met Thr Lys Lys Arg Ser Lys Ile Asn Glu Leu Glu Glu Leu Lys Leu
1               5                   10                  15

Asp Met Arg Lys Ile Ser Asn Asp Met Glu Glu Met Cys Gly Ile Leu
            20                  25                  30

Asn Leu Tyr Met Tyr Glu Asp Leu Asn Tyr Arg Met Asn Thr Glu Phe
        35                  40                  45

Asn Ile Ile Lys Ser Gln His Glu Lys Thr Met Leu Asp Met Asn Lys
50                  55                  60

Met Ile Gln Ser Ile Ile Gly Ser Met Gln Tyr Ser Lys Glu Leu Ile
65                  70                  75                  80

Glu Asp Asn Tyr Ser Tyr Ser Ile Lys Glu Asp His Leu Leu Arg Glu
                85                  90                  95

Cys Thr Gln Leu Asn Glu Lys Val Arg Ile Leu Leu Asn Glu Asn Arg
            100                 105                 110

Arg Leu Leu Val Glu Gln Ala Gly His Lys Cys Pro Val Gly Lys Lys
        115                 120                 125

Arg Gly Ser Leu Arg Lys Pro Ala Arg Thr Ser Val Ser Gln Val Pro
130                 135                 140

Arg Asn Ser Ser Val Lys
145                 150

<210> SEQ ID NO 20
<211> LENGTH: 193
<212> TYPE: PRT
<213> ORGANISM: Mouse

<400> SEQUENCE: 20

Met Ala Met Lys Glu Arg Pro Asp Gln Gln Arg Arg Lys Arg Glu Ser
1               5                   10                  15

Phe Leu Met Lys Lys Glu Glu Gly Asn His Ser Gly Glu Gly Thr Gly
            20                  25                  30

Leu Leu Glu Ile Leu Gln Pro Lys Ile Pro Lys Met Thr Lys Lys Arg
        35                  40                  45

Ser Lys Ile Asn Glu Leu Glu Glu Leu Lys Leu Asp Met Arg Lys Ile
50                  55                  60

Ser Asn Asp Met Glu Glu Met Cys Gly Ile Leu Asn Leu Tyr Met Tyr
65                  70                  75                  80

Glu Asp Leu Asn Tyr Arg Met Asn Thr Glu Phe Asn Ile Ile Lys Ser
                85                  90                  95

Gln His Glu Lys Thr Met Leu Asp Met Asn Lys Met Ile Gln Ser Ile
            100                 105                 110

Ile Gly Ser Met Gln Tyr Ser Lys Glu Leu Ile Glu Asp Asn His Ser
        115                 120                 125

Tyr Ser Ile Lys Glu Asp His Leu Leu Arg Glu Cys Thr Gln Leu Asn
130                 135                 140

Glu Asn Val Arg Ile Leu Leu Asn Glu Asn Arg Arg Leu Leu Val Glu
145                 150                 155                 160

Gln Ala Gly Tyr Lys Cys Pro Val Gly Lys Lys Arg Gly Ser Leu Arg
                165                 170                 175

Arg Pro Ala Arg Thr Ser Val Ser Gln Val Pro Arg Asn Ser Ser Val
            180                 185                 190

Lys
```

<210> SEQ ID NO 21
<211> LENGTH: 150
<212> TYPE: PRT
<213> ORGANISM: Mouse

<400> SEQUENCE: 21

Met Thr Lys Lys Arg Ser Lys Ile Asn Glu Leu Glu Glu Lys Leu
1               5                   10                  15

Asp Met Arg Lys Ile Ser Asn Asp Met Glu Glu Met Cys Gly Ile Leu
            20                  25                  30

Asn Leu Tyr Met Tyr Glu Asp Leu Asn Tyr Arg Met Asn Thr Glu Phe
        35                  40                  45

Asn Ile Ile Lys Ser Gln His Glu Lys Thr Met Leu Asp Met Asn Lys
    50                  55                  60

Met Ile Gln Ser Ile Ile Gly Ser Met Gln Tyr Ser Lys Glu Leu Ile
65                  70                  75                  80

Glu Asp Asn Tyr Ser Tyr Ser Ile Lys Glu Asp His Leu Leu Arg Glu
                85                  90                  95

Cys Thr Gln Leu Asn Glu Asn Val Arg Ile Leu Leu Asn Glu Asn Arg
            100                 105                 110

Arg Leu Leu Val Glu Gln Ala Gly His Lys Cys Pro Val Gly Lys Lys
        115                 120                 125

Arg Gly Ser Leu Arg Arg Pro Ala Arg Thr Ser Val Ser Gln Val Pro
    130                 135                 140

Arg Asn Ser Ser Val Ile
145                 150

<210> SEQ ID NO 22
<211> LENGTH: 150
<212> TYPE: PRT
<213> ORGANISM: Mouse

<400> SEQUENCE: 22

Met Thr Lys Lys Arg Ser Lys Arg Asn Glu Leu Glu Glu Lys Leu
1               5                   10                  15

Asp Met Arg Lys Ile Ser Asn Asp Met Glu Glu Met Cys Gly Ile Leu
            20                  25                  30

Asn Leu Tyr Met Tyr Glu Asp Leu Asn Tyr Arg Met Asn Thr Glu Phe
        35                  40                  45

Asn Ile Ile Lys Ser Gln His Glu Lys Thr Met Leu Asp Met Asn Lys
    50                  55                  60

Met Ile Gln Ser Ile Ile Gly Ser Met Gln Tyr Ser Lys Glu Leu Ile
65                  70                  75                  80

Glu Asp Asn Tyr Ser Tyr Ser Ile Lys Glu Asp His Leu Leu Arg Glu
                85                  90                  95

Cys Thr Gln Leu Asn Glu Asn Val Arg Ile Leu Leu Asn Glu Asn Arg
            100                 105                 110

Arg Leu Leu Val Glu Gln Ser Gly His Lys Cys Pro Val Gly Lys Lys
        115                 120                 125

Arg Gly Ser Leu Arg Arg Pro Ala Arg Thr Ser Val Ser Gln Val Pro
    130                 135                 140

Arg Asn Ser Ser Val Ile
145                 150

<210> SEQ ID NO 23
<211> LENGTH: 148
<212> TYPE: PRT

<213> ORGANISM: Mouse

<400> SEQUENCE: 23

Met Thr Lys Gln Arg Ser Lys Ile Asn Glu Leu Glu Glu Leu Lys Leu
1               5                   10                  15

Asp Met Arg Lys Ile Ser Asn Asp Met Glu Met Cys Gly Ile Leu
            20                  25                  30

Asn Leu Tyr Met Tyr Glu Asp Leu Asn Tyr Arg Met Asn Thr Glu Phe
        35                  40                  45

Asn Ile Ile Lys Ser Gln His Glu Lys Thr Met Leu Asp Met Asn Lys
    50                  55                  60

Met Ile Gln Ser Ile Ile Gly Ser Met Gln Tyr Ser Lys Glu Leu Ile
65                  70                  75                  80

Glu Asp Asn Tyr Ser Tyr Ser Ile Lys Glu Asp His Leu Leu Arg Glu
                85                  90                  95

Cys Thr Gln Leu Asn Glu Asn Val Arg Ile Leu Leu Asn Glu Asn Arg
            100                 105                 110

Arg Leu Leu Val Glu Gln Ala Gly His Lys Cys Pro Val Gly Lys Lys
        115                 120                 125

Arg Gly Ser Leu Arg Arg Pro Ala Arg Thr Ser Val Ser Gln Val Pro
    130                 135                 140

Arg Asn Ser Ser
145

<210> SEQ ID NO 24
<211> LENGTH: 150
<212> TYPE: PRT
<213> ORGANISM: Mouse

<400> SEQUENCE: 24

Met Thr Lys Lys Arg Ser Lys Ile Asn Glu Leu Glu Glu Leu Lys Leu
1               5                   10                  15

Asp Met Arg Lys Ile Ser Asn Asp Met Glu Met Cys Gly Ile Leu
            20                  25                  30

Asn Leu Tyr Met Tyr Glu Asp Leu Asn Tyr Arg Met Asn Thr Glu Phe
        35                  40                  45

Asn Ile Ile Lys Ser Gln His Glu Lys Thr Met Leu Asp Met Asn Lys
    50                  55                  60

Met Ile Gln Ser Ile Ile Gly Ser Met Gln Tyr Ser Lys Glu Leu Ile
65                  70                  75                  80

Glu Asp Asn Tyr Ser Tyr Ser Ile Lys Glu Asp His Leu Leu Arg Glu
                85                  90                  95

Cys Thr Gln Leu His Glu Asn Val Arg Ile Leu Leu Asn Glu Asn Arg
            100                 105                 110

Arg Leu Leu Val Glu Gln Ala Gly His Lys Cys Pro Val Gly Lys Lys
        115                 120                 125

Arg Gly Ser Leu Arg Arg Pro Ala Arg Thr Ser Val Pro Gln Val Pro
    130                 135                 140

Arg Ser Ser Ser Val Ile
145                 150

<210> SEQ ID NO 25
<211> LENGTH: 150
<212> TYPE: PRT
<213> ORGANISM: Mouse

<400> SEQUENCE: 25

```
Met Thr Lys Lys Arg Ser Lys Ile Asn Glu Leu Glu Glu Leu Lys Leu
1               5                   10                  15

Asp Met Arg Lys Ile Ser Asn Asp Met Glu Glu Met Cys Gly Ile Leu
            20                  25                  30

Asn Leu Tyr Met Tyr Glu Asp Leu Asn Tyr Arg Met Asn Thr Glu Phe
        35                  40                  45

Asn Ile Ile Lys Ser Gln His Glu Lys Thr Met Leu Asp Met Asn Lys
    50                  55                  60

Met Ile Gln Ser Ile Ile Val Ser Met Gln Tyr Ser Lys Glu Leu Ile
65                  70                  75                  80

Glu Asp Asn Tyr Ser Tyr Ser Ile Lys Glu Asp His Leu Leu Arg Glu
                85                  90                  95

Cys Thr Gln Leu His Glu Asn Val Arg Ile Leu Leu Asn Glu Asn Arg
            100                 105                 110

Arg Leu Leu Val Asp Gln Ala Gly His Lys Cys Pro Val Gly Lys Lys
            115                 120                 125

Arg Gly Ser Leu Arg Arg Pro Ala Arg Thr Ser Val Ser Gln Val Pro
        130                 135                 140

Arg Asn Thr Ser Val Lys
145                 150

<210> SEQ ID NO 26
<211> LENGTH: 150
<212> TYPE: PRT
<213> ORGANISM: Mouse

<400> SEQUENCE: 26

Met Thr Lys Lys Arg Ser Lys Ile Asn Glu Leu Glu Glu Leu Lys Leu
1               5                   10                  15

Asp Met Arg Lys Ile Ser Asn Asp Met Glu Glu Met Cys Gly Ile Leu
            20                  25                  30

Asn Leu Tyr Met Tyr Glu Asp Leu Asn Tyr Arg Met Asn Thr Glu Phe
        35                  40                  45

Asn Ile Ile Lys Ser Gln His Glu Lys Thr Met Leu Asp Met Asn Lys
    50                  55                  60

Met Ile Gln Ser Ile Ile Gly Ser Met Gln Tyr Ser Lys Glu Leu Ile
65                  70                  75                  80

Glu Asp Asn Tyr Ser Tyr Ser Ile Lys Glu Asp His Leu Leu Arg Glu
                85                  90                  95

Cys Thr Gln Leu His Glu Asn Val Arg Ile Leu Leu Asn Glu Asn Arg
            100                 105                 110

Arg Leu Leu Val Glu Gln Ala Gly His Lys Cys Pro Val Gly Lys Lys
            115                 120                 125

Arg Gly Ser Leu Arg Arg Pro Ala Arg Thr Ser Val Ser Gln Val Pro
        130                 135                 140

Arg Asn Thr Ser Val Lys
145                 150

<210> SEQ ID NO 27
<211> LENGTH: 150
<212> TYPE: PRT
<213> ORGANISM: Mouse

<400> SEQUENCE: 27

Met Thr Lys Lys Arg Ser Lys Arg Asn Glu Leu Glu Glu Leu Lys Leu
1               5                   10                  15
```

Asp Met Arg Lys Ile Ser Asn Asp Met Glu Glu Met Cys Gly Ile Leu
            20                  25                  30

Asn Leu Tyr Met Tyr Glu Asp Leu Asn Tyr Arg Met Asn Thr Glu Phe
        35                  40                  45

Asn Ile Ile Lys Ser Gln His Glu Lys Thr Met Leu Asp Met Asn Lys
    50                  55                  60

Met Ile Gln Ser Ile Ile Gly Ser Met Gln Tyr Ser Lys Glu Leu Ile
65                  70                  75                  80

Glu Asp Asn Tyr Ser Tyr Ser Ile Lys Glu Asp His Leu Leu Arg Glu
                85                  90                  95

Cys Thr Gln Leu His Glu Asn Val Arg Ile Leu Leu Asn Glu Asn Arg
            100                 105                 110

Arg Leu Leu Val Glu Gln Ala Gly His Lys Cys Pro Val Gly Lys Lys
        115                 120                 125

Arg Gly Ser Leu Arg Arg Pro Ala Arg Thr Ser Val Ser Gln Val Pro
    130                 135                 140

Arg Asn Thr Ser Val Ile
145                 150

<210> SEQ ID NO 28
<211> LENGTH: 150
<212> TYPE: PRT
<213> ORGANISM: Mouse

<400> SEQUENCE: 28

Met Thr Lys Lys Arg Ser Lys Ile Asn Glu Leu Glu Glu Leu Lys Leu
1               5                   10                  15

Asp Met Arg Lys Ile Ser Asn Asp Met Glu Glu Met Cys Gly Ile Leu
            20                  25                  30

Asn Leu Tyr Met Tyr Glu Asp Leu Asn Tyr Arg Met Asn Thr Glu Phe
        35                  40                  45

Asn Ile Ile Lys Ser Gln His Glu Lys Thr Met Leu Asp Met Asn Lys
    50                  55                  60

Met Ile Gln Ser Ile Ile Gly Ser Met Gln Tyr Ser Lys Glu Leu Ile
65                  70                  75                  80

Glu Asp Asn Tyr Ser Tyr Ser Ile Lys Glu Asp His Leu Leu Arg Glu
                85                  90                  95

Cys Thr Gln Leu His Glu Asn Val Arg Ile Leu Leu Asn Glu Asn Arg
            100                 105                 110

Arg Leu Leu Val Glu Gln Ala Gly His Lys Cys Pro Val Gly Lys Lys
        115                 120                 125

Arg Gly Ser Leu Arg Arg Pro Ala Arg Thr Ser Val Ser Gln Val Pro
    130                 135                 140

Arg Asn Thr Ser Val Ile
145                 150

<210> SEQ ID NO 29
<211> LENGTH: 150
<212> TYPE: PRT
<213> ORGANISM: Mouse

<400> SEQUENCE: 29

Met Thr Lys Lys Arg Ser Lys Arg Asn Glu Leu Glu Glu Leu Lys Leu
1               5                   10                  15

Asp Met Arg Lys Ile Ser Asn Asp Met Glu Glu Met Cys Gly Ile Leu
            20                  25                  30

```
Asn Leu Tyr Met Tyr Glu Asp Leu Asn Tyr Arg Met Asn Thr Glu Phe
            35                  40                  45

Asn Ile Ile Lys Ser Gln His Glu Lys Thr Met Leu Asp Met Asn Lys
 50                  55                  60

Met Ile Gln Ser Ile Ile Gly Ser Met Gln Tyr Ser Lys Glu Leu Ile
65                  70                  75                  80

Glu Asp Asn Tyr Ser Tyr Ser Ile Lys Glu Asp His Leu Leu Arg Glu
                85                  90                  95

Cys Thr Gln Leu His Glu Asn Val Arg Ile Leu Leu Asn Glu Asn Arg
            100                 105                 110

Arg Leu Leu Val Glu Gln Ala Gly His Lys Cys Pro Val Gly Lys Lys
            115                 120                 125

Arg Gly Ser Leu Arg Arg Pro Ala Arg Thr Ser Val Ser Gln Val Pro
130                 135                 140

Arg Asn Ser Ser Val Lys
145                 150

<210> SEQ ID NO 30
<211> LENGTH: 148
<212> TYPE: PRT
<213> ORGANISM: Mouse

<400> SEQUENCE: 30

Met Thr Lys Lys Arg Ser Lys Arg Asn Glu Leu Glu Glu Leu Lys Leu
1               5                   10                  15

Asp Met Arg Lys Ile Ser Asn Asp Met Glu Glu Met Cys Gly Ile Leu
            20                  25                  30

Asn Leu Tyr Met Tyr Glu Asp Leu Asn Tyr Arg Met Asn Thr Glu Phe
            35                  40                  45

Asn Ile Ile Lys Ser Gln His Glu Lys Thr Met Leu Asp Met Asn Lys
 50                  55                  60

Met Ile Gln Ser Ile Ile Gly Ser Met Gln Tyr Ser Lys Glu Leu Ile
65                  70                  75                  80

Glu Asp Asn Tyr Ser Tyr Ser Ile Lys Glu Asp His Leu Leu Arg Glu
                85                  90                  95

Cys Thr Gln Leu Asn Glu Asn Val Arg Ile Leu Leu Asn Glu Asn Arg
            100                 105                 110

Arg Leu Leu Val Glu Gln Ala Gly His Lys Cys Pro Val Gly Lys Lys
            115                 120                 125

Arg Gly Ser Leu Arg Arg Pro Gln Glu His Leu Cys Pro Lys Cys Gln
130                 135                 140

Gly Thr Ala Val
145

<210> SEQ ID NO 31
<211> LENGTH: 131
<212> TYPE: PRT
<213> ORGANISM: Mouse

<400> SEQUENCE: 31

Met Thr Lys Lys Arg Ser Lys Arg Asn Glu Leu Glu Glu Leu Lys Leu
1               5                   10                  15

Asp Met Arg Lys Ile Ser Asn Asp Met Glu Glu Met Cys Gly Ile Leu
            20                  25                  30

Asn Leu Tyr Met Tyr Glu Asp Leu Asn Tyr Arg Met Asn Thr Glu Phe
            35                  40                  45
```

Asn Ile Ile Lys Ser Gln His Glu Lys Thr Met Leu Asp Met Asn Lys
            50                  55                  60

Met Ile Gln Ser Ile Ile Gly Ser Met Gln Tyr Ser Lys Glu Leu Ile
 65                  70                  75                  80

Glu Asp Asn Tyr Ser Tyr Ser Ile Lys Glu Asp His Leu Leu Arg Glu
                85                  90                  95

Cys Thr Gln Leu His Glu Asn Val Arg Ile Leu Leu Asn Glu Asn Arg
                100                 105                 110

Arg Leu Leu Val Glu Gln Ala Gly His Lys Cys Pro Val Gly Lys Lys
            115                 120                 125

Lys Val Leu
    130

<210> SEQ ID NO 32
<211> LENGTH: 131
<212> TYPE: PRT
<213> ORGANISM: Mouse

<400> SEQUENCE: 32

Met Thr Lys Lys Arg Ser Lys Ile Asn Glu Leu Glu Glu Leu Lys Leu
 1               5                   10                  15

Asp Met Arg Lys Ile Ser Asn Asp Met Glu Glu Met Cys Gly Ile Leu
            20                  25                  30

Asn Leu Tyr Met Tyr Glu Asp Leu Asn Tyr Arg Met Asn Thr Glu Phe
        35                  40                  45

Asn Ile Ile Lys Ser Gln His Glu Lys Thr Met Leu Asp Met Asn Lys
            50                  55                  60

Met Ile Gln Ser Ile Ile Gly Ser Met Gln Tyr Ser Lys Glu Leu Ile
 65                  70                  75                  80

Glu Asp Asn Tyr Ser Tyr Ser Ile Lys Glu Asp His Leu Leu Arg Glu
                85                  90                  95

Cys Thr Gln Leu His Glu Asn Val Arg Ile Leu Leu Asn Glu Asn Glu
                100                 105                 110

Gly Cys Trp Trp Ser Arg Leu Ala Thr Ser Val Leu Trp Gly Arg Lys
            115                 120                 125

Glu Val Leu
    130

<210> SEQ ID NO 33
<211> LENGTH: 111
<212> TYPE: PRT
<213> ORGANISM: Mouse

<400> SEQUENCE: 33

Met Thr Lys Lys Arg Ser Lys Arg Asn Glu Leu Glu Glu Leu Lys Leu
 1               5                   10                  15

Asp Met Arg Lys Ile Ser Asn Asp Met Glu Glu Met Cys Gly Ile Leu
            20                  25                  30

Asn Leu Tyr Met Tyr Glu Asp Leu Asn Tyr Arg Met Asn Thr Glu Phe
        35                  40                  45

Asn Ile Ile Lys Ser Gln His Glu Lys Thr Met Leu Asp Met Asn Lys
            50                  55                  60

Met Ile Gln Ser Ile Ile Gly Ser Met Gln Tyr Ser Lys Glu Leu Ile
 65                  70                  75                  80

Glu Asp Asn Tyr Ser Tyr Ser Pro Ala Glu Ser Arg Thr Trp His Arg
                85                  90                  95

Pro Gly His Asp Leu Pro Gln Arg Glu Val Leu Glu Glu His
            100                 105                 110

<210> SEQ ID NO 34
<211> LENGTH: 146
<212> TYPE: PRT
<213> ORGANISM: Mouse

<400> SEQUENCE: 34

Met Arg Lys Ile Ser Asn Asp Met Glu Glu Met Gly Gly Ile Leu Glu
1               5                   10                  15

Leu Tyr Ile Tyr Glu Asp Leu Asn Tyr Arg Met Asn Thr Glu Phe Asn
            20                  25                  30

Ile Ile Lys Ser Gln His Glu Lys Thr Met Leu Asp Met Asn Glu Met
        35                  40                  45

Ile Gln Ser Ile Ile Val Ser Met Gln Tyr Ser Lys Glu Leu Ile Glu
    50                  55                  60

Asp Asn Tyr Ser Tyr Ser Ile Lys Glu Asp His Leu Leu Arg Glu Cys
65                  70                  75                  80

Thr Gln Leu Ser Glu Lys Val Arg Ile Leu Leu Asn Glu Asn Arg Lys
                85                  90                  95

Leu Leu Val Glu Gln Ala Gly Thr Gln Leu Ser His Gly Glu Glu Lys
            100                 105                 110

Arg Phe Cys Glu Glu Ala Ser Lys Asn Ile Cys Ala Ser Ser Ala Lys
        115                 120                 125

Glu Gln Gln Cys Val Asn Ser Ser Arg Asn Arg Asn Met Ala Gln Thr
    130                 135                 140

Thr Thr
145

<210> SEQ ID NO 35
<211> LENGTH: 71
<212> TYPE: PRT
<213> ORGANISM: Mouse

<400> SEQUENCE: 35

Met Arg Lys Ile Ser Asn Asp Met Glu Glu Met Gly Gly Ile Leu Glu
1               5                   10                  15

Leu Tyr Ile Tyr Glu Asp Leu Asn Tyr Arg Met Asn Thr Glu Phe Asn
            20                  25                  30

Ile Ile Lys Ser Gln His Glu Lys Thr Met Leu Asp Met Asn Glu Met
        35                  40                  45

Ile Gln Ser Ile Ile Val Ser Met Gln Tyr Ser Lys Glu Leu Ile Glu
    50                  55                  60

Asp Asn Tyr Ser Tyr Ser Val
65                  70

<210> SEQ ID NO 36
<211> LENGTH: 114
<212> TYPE: PRT
<213> ORGANISM: Mouse

<400> SEQUENCE: 36

Met Arg Lys Ile Ser Asn Asp Met Glu Glu Met Cys Gly Ile Leu Asp
1               5                   10                  15

Leu Tyr Ile Tyr Glu Asp Leu Asn Tyr Arg Met Asn Thr Glu Phe Asn
            20                  25                  30

Ile Ile Lys Ser Gln His Glu Lys Thr Ile Leu Asp Met Asn Lys Met
         35                  40                  45

Ile Gln Ser Ile Ile Gly Ser Met Gln Tyr Ser Lys Glu Leu Ile Glu
     50                  55                  60

Asp Asn Tyr Ser Tyr Ser Ile Lys Glu Asp His Leu Leu Arg Glu Cys
65                  70                  75                  80

Thr Gln Leu His Glu Asn Val Arg Ile Leu Leu Asn Glu Asn Arg Arg
             85                  90                  95

Leu Leu Val Glu Gln Ala Gly His Lys Cys Pro Val Gly Arg Lys Val
            100                 105                 110

Val Leu

<210> SEQ ID NO 37
<211> LENGTH: 72
<212> TYPE: PRT
<213> ORGANISM: Mouse

<400> SEQUENCE: 37

Met Arg Lys Ile Ser Asn Asp Met Glu Glu Met Cys Gly Ile Leu Asp
1               5                   10                  15

Leu Tyr Met Tyr Glu Asp Leu Asn Tyr Arg Met Asn Thr Glu Phe Asn
            20                  25                  30

Ile Ile Lys Ser Gln His Glu Lys Thr Met Leu Asp Met Asn Lys Met
         35                  40                  45

Ile Gln Ser Ile Ile Gly Ser Met Gln Tyr Ser Lys Glu Leu Ile Glu
     50                  55                  60

Asp Asn Tyr Ser Tyr Ser Val Lys
65                  70

<210> SEQ ID NO 38
<211> LENGTH: 939
<212> TYPE: DNA
<213> ORGANISM: Mouse

<400> SEQUENCE: 38
ggatcccacg ggtccatgag aggctccagg agaggcaccc cagaaaagga ccaagctggg      60
cagaactagt taacaggtag gtcatggcag ttgctagtga catcatcagt aatgccttcc     120
ttggagaatc tcttgtatct aggatagaac tagaatcctc tgcgttgtca cctgtgttgt     180
ggtgacagca actgcctgtg gttcatccct tctgtttgct ctgggttcac cagcaggaat     240
gttttcctgg ctgctcaggc tatttcagaa agagaatggc gatgaaggag agaccagacc     300
aacagagaag gaagagggaa tcctttctca tgaaaaggga agaaggaaat cattctggag     360
aaggcacagg tctgctagaa atacttcaac ccaaaattcc aaaatgacta agaagagatc     420
aaaaataaat gaactagaag aactgaaatt ggatatgagg aagatcagca atgacatgga     480
ggaaatgtgt ggaatcctga acctttacat gtatgaggat ttgaactaca ggatgaacac     540
tgaattcaac atcattaaat cacaacatga aagacaatg ttggatatga ataaatgat      600 ccagtccata attggttcca tgcagtactc aaggaactg atagaagata actattccta     660
cagcattaag gaggaccacc tcctccgtga gtgcactcaa ctcaacgaaa acgtaaggat     720
attactgaat gagaacagaa ggctgctggt ggagcaggct ggccataagt gtcctgtggg     780
gaagaaaaga ggttctctga ggaagccagc aagaacatct gtgtcccaag tgccaaggaa     840
cagcagtgtg aaatagtcca gcagaaagca gaacacggca cagaccacga catgatctcc     900
ctcaaagaga agtgctggag gaagagcact gagtgtgca                            939

<210> SEQ ID NO 39
<211> LENGTH: 939
<212> TYPE: DNA
<213> ORGANISM: Mouse

<400> SEQUENCE: 39

```
ggatcccacg ggtccatgag aggctccagg agaggcaccc cagaaaagga ccaagctggg      60
cagaactagt taacaggtag gtcatggcag ttgctagtga catcatcagt aatgccttcc     120
ttggagaatc tcttgtatct aggataaaac tagaatcctc tgcgttgtca cctgtgttgt     180
ggtgacagca actgcctgtg gttcatccct tctgtttgct ctgggttcac cagcaggaat     240
gttttcctgg ctgctcaggc tatttcagaa agagaatggc gatgaaggag agaccagacc     300
aacagagaag gaagagggaa tcctttctca tgaaaaagga agaaggaaat cattctggag     360
aaggcacagg tctgctagaa atacttcaac ccaaaattcc aaaatgacta agaagagatc     420
aaaaataaat gaactagaag aactgaaatt ggatatgagg aagatcagca atgacatgga     480
ggaaatgtgt ggaatcctga acctttacat gtatgaggat ttgaactaca ggatgaacac     540
tgaattcaac atcattaaat cacaacatga gaagacaatg ttggatatga ataaaatgat     600
ccagtccata attggttcca tgcagtactc caaggaactg atagaagata actattccta     660
cagcattaag gaggaccacc tcctccgtga gtgcactcaa ctcaacgaaa acgtaaggat     720
attactgaat gagaacagaa ggctgctggt ggagcaggct ggctataagt gtcctgtggg     780
gaagaaaaga ggttctctga ggaggccagc aagaacatct gtgtcccaag tgccaaggaa     840
cagcagtgtg aaatagtcca gctgaaagca gaacatggca cagaccagga catgatctcc     900
ctcaaagaga agtgctggag gaagagcact gagtgtgca                            939
```

<210> SEQ ID NO 40
<211> LENGTH: 939
<212> TYPE: DNA
<213> ORGANISM: Mouse

<400> SEQUENCE: 40

```
ggatcccacg ggtccatgag aggctccagg agaggcaccc cagaaaagga ccaagctggg      60
cagaactagt taacaggtag gtcatggcag ttgctagtga catcatcagt aatgccttcc     120
ttggagaatc tcttgtatct aggatagaac tagaatcttc tgtgttgtca cctgtgttgt     180
ggtgacagca actgcctgtg gttcatccct tctgtttgct ctgggttcac cagcaggaat     240
gttttcctgg ctgctcaggc tatttcagaa agagaatggc gatgaaggag agaccagacc     300
aacagagaag gaagagggaa tcctttctca tgaaaaagga agaaggaaat cattctggag     360
aaggcacagg tctgctagaa atacttcaac ccaaaattcc aaaatgacca agaagagatc     420
aaaaataaat gaactagaag aactgaaatt ggatatgagg aagatcagca atgacatgga     480
ggaaatgtgt ggaatcctga acctttacat gtatgaggat ttgaactaca ggatgaacac     540
tgaattcaac atcattaaat cacaacatga gaagacaatg ttggatatga ataaaatgat     600
ccagtccata attggttcca tgcagtactc caaggaactg atagaagata actattccta     660
cagcattaag gaggaccacc tcctccgtga gtgcactcaa ctcaacgaaa acgtaaggat     720
attactgaat gagaacagaa ggctgctggt ggagcaggct ggccataagt gtcctgtggg     780
gaagaaaaga ggttctctga ggaggccagc aagaacatct gtgtcccaag tgccaaggaa     840
cagcagtgtg atatagtcca gcagaaagca gaacatggca cagaccacga catgatctcc     900
```
ctcaaagaga agtgctggag aagagcact gagtgtgca                               939

<210> SEQ ID NO 41
<211> LENGTH: 939
<212> TYPE: DNA
<213> ORGANISM: Mouse

<400> SEQUENCE: 41
ggatcccacg ggtccatgag aggctccagg agaggcaccc cagaaaagga ccaagctggg        60
cagaactagt taacaggtag gtcatggcag ttgctagtga catcatcagt aatgccttcc       120
ttggagaatc tcttgtatct aggatagaac tagaatcctc tgtgttgtca cctgtgttgt       180
ggtgacagca actgcctgtg gttcatccct tctgtttgct ctgggttcac cagcaggaat       240
gttttcctgg ctgctcaggc tatttcagaa agagaatggc gatgaaggag agaccagacc       300
aacagagaag gaagagggaa tcctttctca tgaaaaagga agaaggaaat cattctggag       360
aaggcacagg tctgctagaa atacttcaac ccaaaattcc aaaatgacta agaagagatc       420
aaaaataaat gaactagaag aactgaaatt ggatatgagg aagatcagca atgacatgga       480
ggaaatgtgt ggaatcctga acctttacat gtatgaggat ttgaactaca ggatgaacac       540
tgaattcaac atcattaaat cacaacatga aagacaatg ttggatatga ataaatgat        600 ccagtccata attggttcca tgcagtattc caaggaactg atagaagata actattccta       660
cagcattaag gaggaccacc tcctccgtga gtgcactcaa ctcaacgaaa acgtaaggat       720
attactgaat gagaacagaa ggctgctggt ggagcaggct ggccataagt gtcctgtggg       780
gaagaaaaga ggttctctga ggaggccagg aagtacatct gtgtcccaag tgccaaggaa       840
cagcagtgtg atatagtcca gcagaaagca gaacatggca cagaccacgg catgatctcc       900
ctcaaagaga agtgctggag gaagagcact gagtgtgca                             939

<210> SEQ ID NO 42
<211> LENGTH: 939
<212> TYPE: DNA
<213> ORGANISM: Mouse

<400> SEQUENCE: 42
ggatcacacg ggtccatgag aagctccagg agaggcaccc cagaaaggga ccaagctggg        60
cagaactagt taacaggtag gtcatggcag ttgctagtga catcatcagt aatgccttcc       120
ttggagaatc tcttgtatct aggatagaac tagaatcctc tgcgttgtca cctgtgttgt       180
ggtgacagca actgcctgtg gttcatccct tctgtttgct ctgggttcac cagcaggaat       240
gttttcctgg ctgctcaggc tatttcagaa agagactggc gatgaaggag agaccagacc       300
aacagagaag gaagagggaa tcctttctca tgaaaaagga agaaggaaat cattctggag       360
aaggcacagg tctgctagaa atacttcaac ccaaaattcc aaaatgacca agaagagatc       420
aaaaataaat gaactagaag aactgaaatt ggatatgagg aagatcagca atgacatgga       480
ggaaatgtgt ggaatcctga acctttacat gtatgaggat ttgaactaca ggatgaacac       540
tgaattcaac atcattaaat cacaacatga aagacaatg ttggatatga ataaatgat        600 ccagtccata attggttcca tgcagtactc caaggaactg atagaagata actattccta       660
cagcattaag gaggaccacc tcctccgtga gtgcactcaa ctcaacgaaa acgtaaggat       720
attactgaat gagaacagaa ggctgctggt ggagcaggct ggccataagt gtcctgtggg       780
gaagaaaaga ggttctctga ggaggccagc aagaacatct gtgtcccaag tgccaaggaa       840
cagcagtgtg aaatagtcca acagaaagca gaacatggca cagaccacga catgatctcc       900

```
ctcaaagaga agtgctggag gaagagcact gagtgtgca                                 939
```

<210> SEQ ID NO 43
<211> LENGTH: 769
<212> TYPE: DNA
<213> ORGANISM: Mouse

<400> SEQUENCE: 43

```
ggatcccacg ggtccatgag aggctccagg agaggcaccc cagaaaagga ccaagctgga           60
cagaactagt taacaggaat gttttcctgg ctgctcaggc tatttcagaa agagaatggc          120
gatgaaggag agaccagacc aacagagaag gaagagggaa tcctttctca tgaaaaagga          180
agaaggaaat cattctggag aaggcacagg tctgctagaa atacttcaac ccaaaattcc          240
aaaatgacta agaagagatc aaaaataaat gaactagaag aactgaaatt ggatatgagg          300
aagatcagca atgacatgga ggaaatgtgt ggaatcctga acctttacat gtatgaggat          360
ttgaactaca ggatgaacac tgaattcaac atcattaaat cacaacatga aagacaatg          420
ttggatatga ataaaatgat ccagtccata attggttcca tgcagtactc catggaactg          480
atagaagata actattccta cagcattaag gaggaccacc tcctccgtga gtgcactcaa          540
ctcaacgaaa acgtaaggat attactgaat gagaacagaa ggctgatggt ggagcaggct          600
ggccataagt gtcctgtggg gaagaaaaga ggttctctga ggaggccagc aagaacatct          660
gtgtcccaag tgccaaggaa cagcagtcca gcagaaagca gaacatggca cagaccagga          720
aatgatctcc ctcaaagaga agtgctggag gaagagcact gagtgtgca                     769
```

<210> SEQ ID NO 44
<211> LENGTH: 988
<212> TYPE: DNA
<213> ORGANISM: Mouse

<400> SEQUENCE: 44

```
ggatcacacg ggtccatgag aagctccagg agaggcaccc cagaaaagga ccaagctggg           60
cagaactagt taacaggtag gtcatggcag ttgctagtga catcatcagt aatgccttcc          120
ttggagaatc tcttgtatct aggatagaac tagaatcctc tgcgttgtca cctgtgttgt          180
ggtgacagca actgcctgtg gttcatccct tctgtttgct ctgggttcac cagcaggaat          240
gttttcctgg ctgctcaggc tatttcagaa agagactggc gatgaaggag agaccagacc          300
aacagagaag gaagagggaa tcctttctca tgaaaaagga agaaggaaat cattctggag          360
aaggcacagg tctgctagaa atacttcaac ccaaaattcc aaaatgacca agaagagatc          420
aaaaataaat gaactagaag aactgaaatt ggatatgagg aagatcagca atgacatgga          480
ggaaatgtgt ggaatcctga acctttacat gtatgaggat ttgaactaca ggatgaacac          540
tgaattcaac atcattaaat cacaacatga aagacaatg ttggatatga ataaaatgat          600
ccagtccata attggttcca tgcagtactc caaggaactg atagaagata actattccta          660
cagggccctt gcagggatca taggacttgt aggagtggca agccaatgga atctggctgg          720
gaatcaccaa ttttttcttt g tggatcagca ttaaggagga ccacctcctc cgtgagtgca         780
ctcaactcaa cgaaaacgta aggatattac tgaatgagaa cagaaggctg ctggtggagc          840
aggctggcca taagtgtcct gtggggaaga aaagaggttc tctgaggagg ccagcaagaa          900
catctgtgtc ccaagtgcca aggaacagca gtgtgaaata gtccaacaga aagcagaaca          960
tggcacagac cacgacatga tctccctc                                            988
```

<210> SEQ ID NO 45
<211> LENGTH: 867
<212> TYPE: DNA
<213> ORGANISM: Mouse

<400> SEQUENCE: 45

| | | | | | |
|---|---|---|---|---|---|
| ggatcccacg | ggtccatgag | aggctccagg | agaggcaccc | cagaaaagga | ccaagctggg | 60 |
| cagaactagt | taacagcagg | aatgttttcc | tggctgctca | ggctatttca | gaaagagaat | 120 |
| ggcgatgaag | gagagaccag | accaacagag | aaggaagagg | gaatcctttc | tcatgaaaaa | 180 |
| ggaagaagga | aatcattctg | gagaaggcac | aggtctgcta | gaaatacttc | aacccaaaat | 240 |
| tccaaaatga | ctaagaagag | atcaaaaata | aatgaactag | aagaactgaa | attggatatg | 300 |
| aggaagatca | gcaatgacat | ggaggaaatg | tgtggaatcc | tgaacccttta | catgtatgag | 360 |
| gatttgaact | acaggatgaa | cactgaattc | aacatcatta | atcacaaca | tgagaagaca | 420 |
| atgttggata | tgaataaaat | gatccagtcc | ataattggtt | ccatgcagta | ttccaaggaa | 480 |
| ctgatagaag | ataactattc | ctacagggcc | cttgcaggga | tcataggact | tgtacgagtg | 540 |
| gcaagccaat | ggaatctggc | tgggaatcac | caatttttct | tgtggatca | gcattaagga | 600 |
| ggaccacctc | ctccgtgagt | gcactcaact | caacgaaaac | gtaaggatat | tactgaatga | 660 |
| gaacagaagg | ctgctggtgg | agcaggctgg | ccataagtgt | cctgtgggga | agaaaagagg | 720 |
| ttctctgagg | aggccaggaa | gtacatctgt | gtcccaagtg | ccaaggaaca | gcagtgtgat | 780 |
| atagtccagc | agaaagcaga | acatggcaca | gaccacggca | tgatctccct | caaagagaag | 840 |
| tgctggagga | agagcactga | gtgtgca | | | | 867 |

<210> SEQ ID NO 46
<211> LENGTH: 631
<212> TYPE: DNA
<213> ORGANISM: Mouse

<400> SEQUENCE: 46

| | | | | | |
|---|---|---|---|---|---|
| gactcagaat | ggtctcccct | gcccctgggc | catcaagtat | gcaaattctt | ttgtgtttac | 60 |
| ctatctgcag | ggtctgctag | aaatacttca | acccaaaatt | ccaaaatgac | taagaagaga | 120 |
| tcaaaaataa | atgaactaga | agaactgaaa | ttggatatga | ggaagatcag | caatgacatg | 180 |
| gaggaaatgt | gtggaatcct | gaacctttac | atgtatgagg | atttgaacta | caggatgaac | 240 |
| actgaattca | acatcattaa | atcacaacat | gagaagacaa | tgttggatat | gaataaaatg | 300 |
| atccagtcaa | taattggttc | catgcagtac | tctaaggaac | tgatagaaga | taactattcc | 360 |
| tacagcatta | ggaggaccac | cctcctccgt | gagtgcactc | aactccacga | aaacgtaagg | 420 |
| atattactga | atgagaacag | aaggctgctg | gtggagcagg | ctggccacaa | gtgtcctgtg | 480 |
| gggaagaaaa | gaggttctct | gaggaggcca | gcaagaacat | ctgtgtccca | agtgccaagg | 540 |
| aacagcagtc | cagcagaaag | cagaacatgg | cactgaccac | gacatgatct | ccctcaaaga | 600 |
| gaagtgctgg | aggaagagca | ctgagtgtgc | a | | | 631 |

<210> SEQ ID NO 47
<211> LENGTH: 756
<212> TYPE: DNA
<213> ORGANISM: Mouse

<400> SEQUENCE: 47

| | | | | | |
|---|---|---|---|---|---|
| caggagcagt | ggctaaatgt | tgaactcttc | aaaacttggc | gtatgggctg | ctggtgtacc | 60 |
| accatcatcc | ccaacactcc | tgttcagaag | atgggtgagg | aaagtggaaa | gtctaaccag | 120 |

```
tcagccgatg accagtggga aaaatgagct acaagatcac ctgatcttca tcagtgagaa    180
agctttgcac aagagggtct gctagaaata cttcaaccca aaattccaaa atgactaaga    240
agagatcaaa aataaatgaa ctagaagaac tgaaattgga tatgaggaag atcagcaatg    300
acatggagga aatgtgtgga atcctgaacg tttacatgta tgaggatttg aactacagga    360
tgaacactga attcaacatc attaaatcac aacatgagaa acaatgttg gatatgaata    420 aaatgatcca gtccataatt ggttccatgc agtactccaa ggaactgata aagataact    480 attcctacag cattaaggag gaccacctcc tccgtgagtg cactcaactc cacgaaaacg    540
taaggatatt actgaatgag aacagaaggc tgctggtgga gcaggctggc cacaagtgtc    600
ctgtggggaa gaaaagaggt tctctgagga ggccagcaag aacatctgtg tcccaagtgc    660
caaggaacag cagtccagca gaaagcagaa catggcacag accaggacat gatctccctc    720
aaagagaagt gctggaggaa gagcactgag tgtgca                              756
```

```
<210> SEQ ID NO 48
<211> LENGTH: 631
<212> TYPE: DNA
<213> ORGANISM: Mouse

<400> SEQUENCE: 48
gactcagaat ggtctcccct gccctgggc catcaagtat gcaaattctt ttgtgtttac     60
ctatctgcag ggtctgctag aaatacttca acccaaaatt ccaaaatgac taagaagaga    120
tcaaaaataa atgaactaga gaactgaaa ttggatatga ggaagatcag caatgacatt    180
gaggaaatgt gtggaatcct aaacctttac atgtatgagg atttgaacta caggatgaac    240
actgaattca acatcattaa atcacaacat gagaagacaa tgttggatat gaataaaatg    300
atccagtcaa taattggttc catgcagtac tctaaggaac tgatagaaga taactattcc    360
tacagcatta aggaggacca cctcctccgt gagtgcactc aactccacga aaacgtaagg    420
atattactga atgagaacag aaggctgctg gtggagcagg ctggccacaa gtgtcctgtg    480
gggaagaaaa gaggttctct gaggaggcca gcaagaacat ctgtgtccca agtgccaagg    540
aacagcagtc cagcagaaag cagaacatgg cacagaccag gacatgatct ccctcaaaga    600
gaagtgctgg aggaagagca ctgagtgtgc a                                   631
```

```
<210> SEQ ID NO 49
<211> LENGTH: 648
<212> TYPE: DNA
<213> ORGANISM: Mouse

<400> SEQUENCE: 49
aagcctaacc actcagccga tgacaagtgg gaaaaatgcg ctacaagatc acctgatatt     60
catcagtgag aaagctttgc acaagagggt ctgctagaaa tacttcaacc caaaattcca    120
aaatgactaa gaagagatca aaaataaatg aactagaaga actgaaattg gatatgagga    180
agatcagcaa tgcatggag gaaatgggtg gaatcctgaa cctttacatg tatgaggatt    240
tgaactacag gatgaacact gaattcaaca tcattaaatc acaacatgag aagacaatgt    300
tggatatgaa taaaatgatc cagtcaataa ttggttccat gcagtactct aaggaactga    360
tagaagataa ctattcctac agcattaagg aggaccacct cctccgtgac tgcactcaac    420
tccacgaaaa cgtaaggata ttactgaatg agaacagaag gctgctggtg gagcaggctg    480
gccacaagtg tcctgtgggg aagaaaagag gttctctgag gaggccagca agaacatctg    540
```

```
tgtcccaagt gccaaggaac agcagtccag cagaaagcag aacatggcac agaccaggac    600
atgatctccc tcaaagagaa gtgctggagg aagagcactg agtgtgca                 648
```

<210> SEQ ID NO 50
<211> LENGTH: 631
<212> TYPE: DNA
<213> ORGANISM: Mouse

<400> SEQUENCE: 50

```
gactcagaat ggtctcccct gcccctgggc catcaagtat gcaaattctt ttgtgtttac     60
ctatctgcag ggtctgctag aaatacttca acccaaaatt ccaaaatgac taagaagaga    120
tcaaaaataa atgaactaga gaactgaaa ttggatatga ggaagatcag caatgacatg    180
gaggaaatgt gtggaatcct gaacctttac atgtatgagg atttgaacta caggatgaac    240
actgaattca acatcattaa atcacaacat gagaagacaa tgttggatat gaataaaatg    300
atccagtcca taattggttc catgcagtac tccaaggaac tgatagaaga taactattcc    360
tacagcatta aggaggacca cctcctccgt gagtgcactc aactcaacga aaacgtaagg    420
atattactga tgagaacag aaggctgctg gtggagcagg ctggccataa gtgtcctgtg    480
gggaagaaaa gaggttctgt gaggaggcca gcaagaacat ctgtgtccca agtgccaagg    540
aacagcagtc cagcagaaag cagaacatgg cacagaccag gacatgatct ccctcaaaga    600
gaagtgctgg aggaagagca ctgagtgtgc a                                   631
```

<210> SEQ ID NO 51
<211> LENGTH: 648
<212> TYPE: DNA
<213> ORGANISM: Mouse

<400> SEQUENCE: 51

```
aagtctaacc agtcagccga tgaccagtgg gaacaatgag ctacaagatc acctgatctt     60
catcagtgag aaagctttgc acaagagggt ctgctagaaa tacttcaacc caaaattcca    120
aaatgactaa gaagagatca aaaataaatg aactagaaga actgaaattg gatatgagga    180
agatcagcaa tgacatggag gaaatgtgtg gaatcctgaa cctttacatg tatgaggatt    240
tgaactacag gatgaacact gaattcaaca tcattaaatc acaacatgag aagacaatgt    300
tggatatgaa taaaatgatc cagtccataa ttggttccat gcagtactcc aaggaactga    360
tagaagataa ctattcctac agcattaagg aggaccacct cctccgtgag tgcactcaac    420
tccacgaaaa cgtaaggata ttactgaatg agaacagaag gctgctggtg gagcaggctg    480
gccacaagtg tcctgtgggg aagaaaagag gttctctgag gatgccagat agaacatctg    540
tgtcccaagt gccaaggaac agcagtccag cagaaagcag aacatggcac agaccaggac    600
atgatctccc tcaaagagaa gtgctggagg aagagcactg agtgtgca                 648
```

<210> SEQ ID NO 52
<211> LENGTH: 637
<212> TYPE: DNA
<213> ORGANISM: Mouse

<400> SEQUENCE: 52

```
ggatcacacg ggtccatgag aggctccagg agaggcaccc cagaaaagga ccaagctggg     60
cagaactagt taacagggtc tgctagaaat acttcaaccc aaaattccaa aatgactaag    120
aagagatcaa aagaaatga actagaagaa ctgaaattgg atatgaggaa gatcagcaat    180
gacatggagg aaatgtgtgg aatcctgaac ctttacatgt atgaggattt gaactacagg    240
```

```
atgaacactg aattcaacat cattaaatca caacatgaga agacaatgtt ggatatgaat    300
aaaatgatcc agtccataat tggttccatg cagtattcca aggaactgat agaagataac    360
tattcctaca gcattaagga ggaccacctc ctccgtgagt gcactcaact ccacgaaaat    420
gtaaggatat tactgaatga aacagaagg ctgctggtgg agcaggctgg ccacaagtgt      480
cctgtgggga agaaaagagg ttctctgagg aggccagcaa gaacatctgt gtcccaagtc    540
ccaaggaaca gcagtccagc agaaagcaga acatggcaca gaccaggaca tgatctccct    600
caaagagaag tgctggagga agagcactga gtgtgca                              637
```

```
<210> SEQ ID NO 53
<211> LENGTH: 641
<212> TYPE: DNA
<213> ORGANISM: Mouse

<400> SEQUENCE: 53
gactcagaat ggtctcccct gcccctgggc cttcaagtat gcaaattctt ttgtgtttac     60
ctatctgcag ggtctgctag aaatacttca acccaaaatt ccaaaatgac taagaagaga   120
tcaaaaataa atgaactaga agaactgaaa ttggatatga ggaagatcag caatgacatg   180
gaggaaatgt gtggaatcct gaacctttac atgtatgagg atttgaacta caggatgaac   240
actgaattca acatcattaa atcacaacat gagaagacaa tgttggatat gaataaaatg   300
atccagtcca taattggttc catgcagtac tccaaggaac tgatagaaga taactattcc   360
tacagcatta aggaggacca cctcctccgt gagtgcactc aactcaacga aaagtaagg    420 atattactga atgagaacag aaggctgctg gtggagcagg ctggccataa gtgtcctgtg   480
gggaagaaaa gaggttctct gaggaagcca gcaagaacat ctgtgtccca agtgccaagg   540
aacagcagtg tgaaatagtc cagcagaaag cagaacatgg cactgaccac gacatgatct   600
ccctcaaaga gaagtgctgg aggaagagca ctgagtgtgc a                        641
```

```
<210> SEQ ID NO 54
<211> LENGTH: 940
<212> TYPE: DNA
<213> ORGANISM: Mouse

<400> SEQUENCE: 54
ggatcccacg ggtccatgag aggctccagg agaggcaccc cagaaaagga ccaagctggg    60
cagaactagt taacaggtag gtcatggcag ttgctagtga catcatcagt aatgccttcc   120
ttggagaatc tcttgtatct aggataaaac tagaatcctc tgcgttgtca cctgtgttgt   180
ggtgacagca actgcctgtg gttcatccct tctgtttgct ctgggttcac cagcaggaat   240
gttttcctgg ctgctcaggc tatttcagaa agagaatggc gatgaaggag agaccagacc   300
aacagagaag gaagagggaa tcctttctca tgaaaaagga agaaggaaat cattctggag   360
aaggcacagg tctgctagaa atacttcaac ccaaaattcc aaaaatgact aagaagagat   420
caaaaataaa tgaactagaa gaactgaaat tggatatgag gaagatcagc aatgacatgg   480
aggaaatgtg tggaatcctg aacctttaca tgtatgagga tttgaactac aggatgaaca   540
ctgaattcaa catcattaaa tcacaacatg agaagacaat gttggatatg aataaaatga   600
tccagtccat aattggttcc atgcagtact ccaaggaact gatagaagat aaccattcct   660
acagcattaa ggaggaccac ctcctccgtg agtgcactca actcaacgaa aacgtaagga   720
tattactgaa tgagaacaga aggctgctgg tggagcaggc tggctataag tgtcctgtgg   780
```

```
ggaagaaaag aggttctctg aggaggccag caagaacatc tgtgtcccaa gtgccaagga      840
acagcagtgt gaaatagtcc agctgaaagc agaacatggc acagaccagg acatgatctc      900
cctcaaagag aagtgctgga ggaagagcac tgagtgtgca                             940
```

<210> SEQ ID NO 55
<211> LENGTH: 641
<212> TYPE: DNA
<213> ORGANISM: Mouse

<400> SEQUENCE: 55

```
gactcagaat ggtctcccct gcccctgggc catcaagtat gcaaattctt ttgtgtttac       60
ctatctgcag ggtctgctag aaatacttca acccaaaatt ccaaaatgac caagaagaga      120
tcaaaaataa atgaactaga agaactgaaa ttggatatga ggaagatcag caatgacatg      180
gaggaaatgt gtggaatcct gaacctttac atgtatgagg atttgaacta caggatgaac      240
actgaattca acatcattaa atcacaacat gagaagacaa tgttggatat gaataaaatg      300
atccagtcca taattggttc catgcagtac tccaaggaac tgatagaaga taactattcc      360
tacagcatta aggaggacca cctcctccgt gagtgcactc aactcaacga aaacgtaagg      420
atattactga atgagaacag aaggctgctg gtggagcagg ctggccataa gtgtcctgtg      480
gggaagaaaa gaggttctct gaggaggcca gcaagaacat ctgtgtccca agtgccaagg      540
aacagcagtg tgatatagtc cagcagaaag cagaacatgg cacagaccac gacatgatct      600
ccctcaaaga gaagtgctgg aggaagagca ctgagtgtgc a                          641
```

<210> SEQ ID NO 56
<211> LENGTH: 641
<212> TYPE: DNA
<213> ORGANISM: Mouse

<400> SEQUENCE: 56

```
gactcagaat ggtctcccct gcccctgggc catcaagtat gcaaattctt ttgtgtttac       60
ctatctgcag ggtctgctag aaatacttca acccaaaatt ccaaaatgac taagaagaga      120 tcaaaagaa atgaactaga agaactgaaa ttggatatga ggaagatcag caatgacatg       180
gaggaaatgt gtggaatcct gaacctttac atgtatgagg atttgaacta caggatgaac      240
actgaattca acatcattaa atcacaacat gagaagacaa tgttggatat gaataaaatg      300
atccagtcca taattggttc catgcagtac tccaaggaac tgatagaaga taactattcc      360
tacagcatta aggaggacca cctcctccgt gagtgcactc aactcaacga aaacgtaagg      420
atattactga atgagaacag aaggctgctg gtggagcagt ctggccataa gtgtcctgtg      480
gggaagaaaa gaggttctct gaggaggcca gcaagaacat ctgtgtccca agtgccaagg      540
aacagcagtg tgatatagtc cagcagaaag cagaacatgg cacagaccac gacatgatct      600
ccctcaaaga gaagtgctgg aggaagagca ctgagtgtgc a                          641
```

<210> SEQ ID NO 57
<211> LENGTH: 646
<212> TYPE: DNA
<213> ORGANISM: Mouse

<400> SEQUENCE: 57

```
gactcagaat ggtctcccct gcccctgggc catcaagtat gcaaattctt ttgtgtttac       60
ctatctgcag ggtctgctag aaatacttca accaaaaatt ccaaaatgac taagcagaga      120
tcaaaaataa atgaactaga agaactgaaa ttggatatga ggaagatcag caatgacatg      180
```

```
gaggaaatgt gtggaatcct gaacctttac atgtatgagg atttgaacta caggatgaac    240
actgaattca acatcattaa atcacaacat gagaagacaa tgttggatat gaataaaatg    300
atccagtcca taattggttc catgcagtac tccaaggaac tgatagaaga taactattcc    360
tacagcatta aggaggacca cctcctccgt gagtgcactc aactcaacga aaacgtaagg    420
atattactga tgagaacag aaggctgctg gtggagcagg ctggccataa gtgtcctgtg    480
gggaagaaaa gaggttctct gaggaggcca gcaagaacat ctgtgtccca gtgccaagg    540 aacagcagct aagtgtgaaa tagtccagct gaaagcagaa catggcacag accaggacat    600
gatctccctc aaagagaagt gctggaggaa gagcactgag tgtgca                  646

<210> SEQ ID NO 58
<211> LENGTH: 659
<212> TYPE: DNA
<213> ORGANISM: Mouse

<400> SEQUENCE: 58
aaagtctaat cagtcagccg atgaccagtg ggaaaaatga gctacaagat cacctgatct     60
tcatcagtga gaaagctttg cacaagaggg tctgctagaa atacttcaac ccaaaattcc    120
aaaatgacta agaagagatc aaaaataaat gaactagaag aactgaaatt ggatatgagg    180
aagatcagca atgacatgga ggaaatgtgt ggaatcctga acctttacat gtatgaggat    240
ttgaactaca ggatgaacac tgaattcaac atcattaaat cacaacatga aagacaatg    300 ttggatatga ataaaatgat ccagtccata attggttcca tgcagtactc caaggaactg    360
atagaagata actattccta cagcattaag gaggaccacc tcctccgtga gtgcactcaa    420
ctccacgaaa acgtaaggat attactgaat gagaacagaa ggctgctggt ggagcaggct    480
ggccacaagt gtcctgtggg gaagaaaaga ggttctctga ggaggccagc aagaacatct    540
gtgcctcaag tgccaaggag cagcagtgtg atatagtcca gcagaaagca gaacatggca    600
cagaccacga catgatctcc ctcaaagaga agtgctggag gaagagcact gagtgtgca    659

<210> SEQ ID NO 59
<211> LENGTH: 658
<212> TYPE: DNA
<213> ORGANISM: Mouse

<400> SEQUENCE: 59
aagtctaatc agtcagccga tgaccagtgg gaaaaatgag ctacaagatc acctgatctt     60
catcagtgag aaagctttgc acaagagggt ctgctagaaa tacttcaacc caaaattcca    120
aaatgactaa gaagagatca aaaataaatg aactagaaga actgaaattg gatatgagga    180
agatcagcaa tgacatggag gaaatgtgtg gaatcctgaa cctttacatg tatgaggatt    240
tgaactacag gatgaacact gaattcaaca tcattaaatc acaacatgag aagacaatgt    300
tggatatgaa taaaatgatc cagtccataa ttgtttccat gcagtactcc aaggaactga    360
tagaagataa ctattcctac agcattaagg aggaccacct cctccgtgag tgcactcaac    420
tccacgaaaa tgtaaggata ttactgaatg agaacagaag gctgctggtg gatcaggctg    480
gccacaagtg tcctgtgggg aagaaaagag gttctctgag gaggccagca agaacatctg    540
tgtcccaagt gccaaggaac accagtgtga aatagtccag cagaaagcag aacatggcac    600
agaccaggac atgatctccc tcaaagagaa gtgctggagg aagagcactg agtgtgca     658

<210> SEQ ID NO 60
```

<211> LENGTH: 766
<212> TYPE: DNA
<213> ORGANISM: Mouse

<400> SEQUENCE: 60

| | |
|---|---|
| caggagcagt ggctaaatgt tgaactcttc aaaacttggc gtatgggctg ctggtgtacc | 60 |
| accatcatcc ccaacactcc tgttcagaag atgggtgagg aaagtggaaa gtctacccag | 120 |
| tcagccgatg accagtggga aaaatgagct acaagatcac ctgatcttca tcagtgagaa | 180 |
| agctttgcac aagagggtct gctagaaata cttcaaccca aaattccaaa atgactaaga | 240 |
| agagatcaaa aataaatgaa ctagaagaac tgaaattgga tatgaggaag atcagcaatg | 300 |
| acatggagga aatgtgtgga atcctgaacc tttacatgta tgaggatttg aactacagga | 360 |
| tgaacactga attcaacatc attaaatcac aacatgagaa gacaatgttg gatatgaata | 420 |
| aaatgatcca gtccataatt ggttccatgc agtactccaa ggaactgata aagataact | 480 |
| attcctacag cattaaggag gaccacctcc tccgtgagtg cactcaactc cacgaaaacg | 540 |
| taaggatatt actgaatgag aacagaaggc tgctggtgga gcaggctggc acaagtgtc | 600 |
| ctgtggggaa gaaagaggt tctctgagga ggccagcaag aacatctgtg tcccaagtgc | 660 |
| caaggaacac cagtgtgaaa tagtccagca gaaagcagaa catggcacag accaggacat | 720 |
| gatctccctc aaagagaagt gctggaggaa gagcactgag tgtgca | 766 |

<210> SEQ ID NO 61
<211> LENGTH: 658
<212> TYPE: DNA
<213> ORGANISM: Mouse

<400> SEQUENCE: 61

| | |
|---|---|
| aagtctaatc agtcagccga tgaccagtgg gaaaaatgag ctacaagatc acctgatctt | 60 |
| catcagtgag aaagctttgc acaagagggt gctctagaaa tacttcaacc caaaattcca | 120 |
| aaatgactaa gaagagatcc aaaagaaatg aactagaaga actgaaattg gatatgagga | 180 |
| agatcagcaa tgacatggag gaaatgtgtg gaatcctgaa cctttacatg tatgaggatt | 240 |
| tgaactacag gatgaacact gaattcaaca tcattaaatc acaacatgag aagacaatgt | 300 |
| tggatatgaa taaaatgatc cagtccataa ttggttccat gcagtactcc aaggaactga | 360 |
| taagagataa ctattcctac agcattaagg aggaccacct cctccgtgag tgcactcaac | 420 |
| tccacgaaaa cgtaaggata ttactgaatg agaacagaag gctgctggtg gagcaggctg | 480 |
| gccacaagtg tcctgtgggg aagaaaagag gttctctgag gaggccagca agaacatctg | 540 |
| tgtcccaagt gccaaggaac accagtgtga tatagtccag cagaaagcag aacatggcac | 600 |
| agaccacgac atgatctccc tcaaagagaa gtgctggagg aagagcactg agtgtgca | 658 |

<210> SEQ ID NO 62
<211> LENGTH: 641
<212> TYPE: DNA
<213> ORGANISM: Mouse

<400> SEQUENCE: 62

| | |
|---|---|
| gactcagaat ggtctcccct gccccctgggc catcaagtat gcaaattctt ttgtgtttac | 60 |
| ctatctgcag ggtctgctag aaatacttca acccaaaatt ccaaaatgac taagaagaga | 120 |
| tcaaaaataa atgaactaga agaactgaaa ttggatatga ggaagatcag caatgacatg | 180 |
| gaggaaatgt gtggaatcct gaacctttac atgtatgagg atttgaacta caggatgaac | 240 |
| actgaattca acatcattaa atcacaacat gagaagacaa tgttggatat gaataaaatg | 300 |

| | |
|---|---|
| atccagtcca taattggttc catgcagtac tccaaggaac tgatagaaga taactattcc | 360 |
| tacagcatta aggaggacca cctcctccgt gagtgcactc aactccacga aaacgtaagg | 420 |
| atattactga atgagaacag aaggctgctg gtggagcagg ctggccacaa gtgtcctgtg | 480 |
| gggaagaaaa gaggttctct gaggaggcca gcaagaacat ctgtgtccca agtgccaagg | 540 |
| aacaccagtg tgatatagtc cagcagaaag cagaacatgg cacagaccac gacatgatct | 600 |
| ccctcaaaga gaagtgctgg aggaagagca ctgagtgtgc a | 641 |

<210> SEQ ID NO 63
<211> LENGTH: 766
<212> TYPE: DNA
<213> ORGANISM: Mouse

<400> SEQUENCE: 63

| | |
|---|---|
| caggagcagt ggctaaatgt tgaactcttc aaaacttggc gtatgggctg ctggtgtacc | 60 |
| accatcatcc ccaacactcc tgttcagaag atgggtgagg aaagtggaaa gtctaatcag | 120 |
| tcagccgatg accagtggga aaatgagct acaagatcac ctgatcttca tcagtgagaa | 180 |
| agctttgcac aagagggtct gctagaaata cttcaaccca aaattccaaa atgactaaga | 240 |
| agagatcaaa aagaaatgaa ctagaagaac tgaaattgga tatgaggaag atcagcaatg | 300 |
| acatggagga aatgtgtgga atcctgaacc tttacatgta tgaggatttg aactacagga | 360 |
| tgaacactga attcaacatc attaaatcac aacatgagaa gacaatgttg gatatgaata | 420 |
| aaatgatcca gtccataatt ggttccatgc agtattccaa ggaactgata gaagataact | 480 |
| attcctacag cattaaggag gaccacctcc tccgtgagtg cactcaactc acgaaaatg | 540 |
| taaggatatt actgaatgag aacagaaggc tgctggtgga gcaggctggc acaagtgtc | 600 |
| ctgtggggaa gaaagaggt tctctgagga ggccagcaag aacatctgtg tcccaagtcc | 660 |
| caaggaacag cagtgtgaaa tagtccagca gaaagcagaa catggcacag accaggacat | 720 |
| gatctcccc aaagagaagt gctggaggaa gagcactgag tgtgca | 766 |

<210> SEQ ID NO 64
<211> LENGTH: 640
<212> TYPE: DNA
<213> ORGANISM: Mouse

<400> SEQUENCE: 64

| | |
|---|---|
| gactcagaat ggtctcccct gccctgggc cttcaagtat gcaaattctt ttgtgtttac | 60 |
| ctatctgcag ggtctgctag aaatacttca acccaaaatt ccaaaatgac caagaagaga | 120 |
| tcaaaaagaa atgaactaga gaactgaaa ttggatatga ggaagatcag caatgacatg | 180 |
| gaggaaatgt gtggaatcct gaaccttac atgtatgagg atttgaacta caggatgaac | 240 |
| actgaattca acatcattaa atcacaacat gagaagacaa tgttggatat gaataaaatg | 300 |
| atccagtcca taattggttc catgcagtac tccaaggaac tgatagaaga taactattcc | 360 |
| tacagcatta aggaggacca cctcctccgt gagtgcactc aactcaacga aaacgtaagg | 420 |
| atattactga atgagaacag aaggctgctg gtggagcagg ctggccataa gtgtcctgtg | 480 |
| gggaagaaaa gaggttctct gaggaggcca caagaacatc tgtgtcccaa gtgccaagga | 540 |
| acagcagtgt gatatagtcc agcagaaagc agaacatggc acagaccacg acatgatctc | 600 |
| cctcaaagag aagtgctgga ggaagagcac tgagtgtgca | 640 |

<210> SEQ ID NO 65

<210> SEQ ID NO 65
<211> LENGTH: 640
<212> TYPE: DNA
<213> ORGANISM: Mouse

<400> SEQUENCE: 65

```
gactcagaat ggtctcccct gcccctgggc catcaagtat gcaaattctt ttgtgtttac      60
ctatctgcag ggtctgctag aaatacttca acccaaaatt ccaaaatgac taagaagaga     120
tccaaaagaa atgaactaga agaactgaaa ttggatatga ggaagatcag caatgacatg     180
gaggaaatgt gtggaatcct gaacctttac atgtatgagg atttgaacta caggatgaac     240
actgaattca acatcattaa atcacaacat gagaagacaa tgttggatat gaataaaatg     300
atccagtcca taattggttc catgcagtac tccaaggaac tgatagaaga taactattcc     360
tacagcatta aggaggacca cctcctccgt gagtgcactc aactccacga aaacgtaagg     420
atattactga atgagaacag aaggctgctg gtggagcagg ctggccacaa gtgtcctgtg     480
gggaagaaaa aggttctctg aggaggccag caagaacatc tgtgtcccaa gtgccaagga     540
acaccagtgt gatatagtct agcagaaagc agaacatggc acagaccacg acatgatctc     600
ccacaaagag aagtgctgga ggaagagcac tgagtgtgca                           640
```

<210> SEQ ID NO 66
<211> LENGTH: 647
<212> TYPE: DNA
<213> ORGANISM: Mouse

<400> SEQUENCE: 66

```
aagtctaccc agtcagccga tgaccagtgg gaaaaatgag ctacaagatc acctgatctt      60
catcagtgag aaagctttgc acaagagggt ctgctagaaa tacttcaacc caaaattcca     120
aaatgactaa gaagagatca aaaataaatg aactagaaga actgaaattg gatatgagga     180
agatcagcaa tgcatggag gaaatgtgtg gaatcctgaa cctttacatg tatgaggatt     240
tgaactacag gatgaacact gaattcaaca tcattaaatc acaacatgag aagacaatgt     300
tggatatgaa taaatgatc cagtccataa ttggttccat gcagtactcc aaggaactga     360
tagaagataa ctattcctac agcattaagg aggaccacct cctccgtgag tgcactcaac     420
tccacgaaaa cgtaaggata ttactgaatg agaacgaagg ctgctggtgg agcaggctgg     480
ccacaagtgt cctgtgggga agaaaagagg ttctctgagg aggccagcaa gaacatctgt     540
gtcccaagtg ccaaggaaca gcagtccagc agaaagcaga acatggcaca gaccaggaca     600
tgatctccct caaagagaag tgctggagga agagcactga gtgtgca                  647
```

<210> SEQ ID NO 67
<211> LENGTH: 573
<212> TYPE: DNA
<213> ORGANISM: Mouse

<400> SEQUENCE: 67

```
caggagcagt ggctaaatgt tgaactcttc aaaacttggc gtatgggctg ctggtgtacc      60
accatcatcc ccaacactcc tgttcagaag atgggtgagg aaagtggaaa gtctaatcag     120
tcagccgatg accagtggga aaaatgagct acaagatcac ctgatcttca tcagtgagaa     180
agctttgcac aagagggtct gctagaaata cttcaaccca aaattccaaa atgactaaga     240
agagatcaaa agaaatgaa ctagaagaac tgaaattgga tatgaggaag atcagcaatg     300
acatggagga aatgtgtgga atcctgaacc tttacatgta tgaggatttg aactacagga     360
tgaacactga attcaacatc attaaatcac aacatgagaa gacaatgttg gatatgaata     420
```

```
aaatgatcca gtccataatt ggttccatgc agtattccaa ggaactgata gaagataact    480
attcctacag tccagcagaa agcagaacat ggcacagacc aggacatgat ctccctcaaa    540
gagaagtgct ggaggaagag cactgagtgt gca                                 573
```

<210> SEQ ID NO 68
<211> LENGTH: 658
<212> TYPE: DNA
<213> ORGANISM: Mouse

<400> SEQUENCE: 68

```
aagtctaatc agtcagccga tgaccagtgg gaaaaatgag ctacaagatc acctgatctt     60
catcagtgag aaagctttgc acaagagggt ctgctagaaa tacttcaacc caaaattcca    120
aaatcactaa gcagagatca aaataaatg aactagaaga actgaaattg gatatgagga    180
agatcagcaa tgcatggag gaaatgggtg gaatcctgga actttacata tatgaggatt    240
tgaactacag gatgaacact gaattcaaca tcattaaatc acaacatgag aagacaatgt    300
tggatatgaa tgaaatgatc cagtccataa ttgtttccat gcagtactcc aaggaactga    360
tagaagataa ctattcctac agcattaagg aggaccacct cctccgtgag tgcactcaac    420
tcagcgaaaa agtaaggata ttactgaatg agaacagaaa gctgctagtg gagcaggctg    480
gaacgcaatt gtctcatggg gaagaaaaga ggttctgtga ggaggccagc aagaacatct    540
gtgcctcaag tgccaaggag cagcagtgtg taaactccag tagaaaccgg aacatggcac    600
agaccacgac atgatctccc tcaaagagaa gtgctggagg aggagcactg agtgtgca     658
```

<210> SEQ ID NO 69
<211> LENGTH: 474
<212> TYPE: DNA
<213> ORGANISM: Mouse

<400> SEQUENCE: 69

```
aagtctaatc agtcagccga tgaccagtgg gaaaaatgag ctacaagatc acctgatctt     60
catcagtgag aaagctttgc acaagagggt ctgctagaaa tacttcaacc caaaattcca    120
aaatcactaa gcagagatca aaataaatg aactagaaga actgaaattg gatatgagga    180
agatcagcaa tgcatggag gaaatgggtg gaatcctgga actttacata tatgaggatt    240
tgaactacag gatgaacact gaattcaaca tcattaaatc acaacatgag aagacaatgt    300
tggatatgaa tgaaatgatc cagtccataa ttgtttccat gcagtactcc aaggaactga    360
tagaagataa ctattcctac agtgtgtaaa ctccagtaga aaccggaaca tggcacagac    420
cacgacatga tctccctcaa agagaagtgc tggaggaaga gcactgagtg tgca          474
```

<210> SEQ ID NO 70
<211> LENGTH: 640
<212> TYPE: DNA
<213> ORGANISM: Mouse

<400> SEQUENCE: 70

```
gactcagaat ggtctcccct gcgcctgggc atcaagtat gcaaattctt ttgtgtttat     60
ctatctgcag ggtctgctag aaatacttca acccagaatt ccaaaatcac taagaagaga    120
tcaaaaataa atgaactaga agaattgaaa ttggatatga ggaagatcag caatgacatg    180
gaggaaatgt gtggaatcct ggaccttac atatatgagg atttgaacta caggatgaac    240
actgaattca acatcattaa atcacaacat gagaagacaa tattggatat gaataaaatg    300
```

```
atccagtcca taattggttc catgcagtac tccaaggaac tgatagaaga taactattcc    360
tacagcatta aggaggacca cctcctccgt gagtgcactc aactccacga aaacgtaagg    420
atattactga atgagaacag aaggctgctg gtggagcagg ctggccacaa gtgtcctgtg    480
ggaagaaaag tggttctctg aggaggccag caagaacatc tgtgtcccaa gtgccaagga    540
acagcagtgt gaaatagtcc agcagaaagc agaacatggc acagaccagg acatgatctc    600
cctcaaagag aagtgctgga ggaagagcac tgagtgtgca                         640
```

<210> SEQ ID NO 71
<211> LENGTH: 475
<212> TYPE: DNA
<213> ORGANISM: Mouse

<400> SEQUENCE: 71

```
aagtctaatc agtcagccga tgaccagtgg gaaaaatgag ctacaagatc acctgatctt     60
catcagtgag aaagctttgc acaagaggat ctgctagaaa tacttcaacc caaaagtcca    120
aaatcactaa gcagaaatca aatataaatg aactagaaga attgaatttg gatatgagga    180
agatcagtaa tgcatggag gaaatgtgtg gaatcctgga cctttacatg tatgaggatt    240
tgaactacag gatgaacact gaattcaaca tcattaaatc acaacatgag aagacaatgt    300
tggatatgaa taaaatgatc cagtccataa ttggttccat gcagtactcc aaggaactga    360
tagaagataa ctattcctac agtgtgaaat aggcaggcag aaagcagaac atggcacaga    420
ccaggacatg atctccctca aagagaagtg ctggaggaag agcactgagt gtgca         475
```

<210> SEQ ID NO 72
<211> LENGTH: 20
<212> TYPE: DNA
<213> ORGANISM: Primer

<400> SEQUENCE: 72

```
catccccaac actcctgttc                                                20
```

<210> SEQ ID NO 73
<211> LENGTH: 21
<212> TYPE: DNA
<213> ORGANISM: Primer

<400> SEQUENCE: 73

```
gaggagcata cagcccatta c                                              21
```

<210> SEQ ID NO 74
<211> LENGTH: 29
<212> TYPE: DNA
<213> ORGANISM: Primer

<400> SEQUENCE: 74

```
ctagctagca agatgggtga ggaaagtgg                                      29
```

<210> SEQ ID NO 75
<211> LENGTH: 29
<212> TYPE: DNA
<213> ORGANISM: Primer

<400> SEQUENCE: 75

```
ccgctcgagt gcacactcag tgctcttcc                                      29
```

<210> SEQ ID NO 76
<211> LENGTH: 22

```
<212> TYPE: DNA
<213> ORGANISM: Primer

<400> SEQUENCE: 76
cagctggaag atagcttttc tg                                              22

<210> SEQ ID NO 77
<211> LENGTH: 29
<212> TYPE: DNA
<213> ORGANISM: Primer

<400> SEQUENCE: 77
ctagctagct ccctccatct tcttcttgg                                       29

<210> SEQ ID NO 78
<211> LENGTH: 19
<212> TYPE: DNA
<213> ORGANISM: Primer

<400> SEQUENCE: 78
cccctcaaaa gcacatgac                                                  19

<210> SEQ ID NO 79
<211> LENGTH: 29
<212> TYPE: DNA
<213> ORGANISM: Primer

<400> SEQUENCE: 79
ctagctagcg aaggagaggt tgccaaagg                                       29

<210> SEQ ID NO 80
<211> LENGTH: 20
<212> TYPE: DNA
<213> ORGANISM: Primer

<400> SEQUENCE: 80
actcgtctcg ccacatgaac                                                 20

<210> SEQ ID NO 81
<211> LENGTH: 31
<212> TYPE: DNA
<213> ORGANISM: Primer

<400> SEQUENCE: 81
ctagctagct tcacagagat gtgagatgga g                                    31

<210> SEQ ID NO 82
<211> LENGTH: 19
<212> TYPE: PRT
<213> ORGANISM: Mouse

<400> SEQUENCE: 82

Thr Lys Lys Arg Ser Lys Ile Asn Glu Leu Glu Glu Leu Lys Leu Asp
1               5                   10                  15

Met Arg Lys

<210> SEQ ID NO 83
<211> LENGTH: 19
<212> TYPE: PRT
<213> ORGANISM: Mouse

<400> SEQUENCE: 83

Cys Pro Val Gly Lys Lys Arg Gly Ser Leu Arg Arg Pro Ala Arg Thr
```

```
1               5               10              15

Ser Val Ser

<210> SEQ ID NO 84
<211> LENGTH: 644
<212> TYPE: DNA
<213> ORGANISM: Probe
<220> FEATURE:
<221> NAME/KEY: misc_feature
<222> LOCATION: (525)..(525)
<223> OTHER INFORMATION: n is a, c, g, or t

<400> SEQUENCE: 84
gcatttctct gagtccctt aaatgtgcac tcttcctggg ccagaggcta gatgaaatta    60
aggcctgttc ataccaaaga aacaaaataa aggaggagca tacagcccat tacagccatg   120
gttattaggg atgagaggca acagtggtgt atttcctgtg cacactcagt gctcttcctc   180
cagcacttct ttttgaggga gatcatgtcg tggtctgtgc cgtgttctgc tttctgctgg   240
actatttcac actgctgttc tttggcactt gggacacaga tgttcttgct ggcctcctca   300
gagaacctct tttcttcccc acaggacact tgtggccagc tgctccacc agcagccttc    360 tgttctcatt cagaaatatc cttacgtttt cgttgagttg agtgcactca cggaggaggt   420
ggtcctcctt aatgctgtag aatagttat cttctatcag ttccttggag tactgcatgg    480
aaccaattat ggactgggat cattttatt catatccaac attgncttct catgttgtga    540
tttaatgatg ttgaattcag tgttcatcct gtagttcaaa tcctcataca tgtaaaggtt   600
caggattcca cacatttcct ccatgtcatt gctgatcttc ctca                    644

<210> SEQ ID NO 85
<211> LENGTH: 653
<212> TYPE: DNA
<213> ORGANISM: Mouse

<400> SEQUENCE: 85
tcttcttctt gggactcaga atggtctccc ctgcccctgg tccatcaagt atgcaaattc    60
ttttgtgttt acctatctgc agggtctgct agaaatactt caacccaaaa ttccaaaatg   120
actaagaaga gatcaaaaat aaatgaacta gaagaactga aattggatat gaggaagatc   180
agcaatgaca tggaggaaat gtgtggaatc ctgaaccttt acatgtatga ggatttgaac   240
tacaggatga acactgaatt caacatcatt aaatcacaac atgagaagac aatgttggat   300
atgaataaaa tgatccagtc cataattggt tccatgcagt actccaagga actgatagaa   360
gataactatt cctacagcat taaggaggac cacctcctcc gtgagtgcac tcaactcaac   420
gaaaacgtaa ggatattact gaatgagaac agaaggctgc tggtggagca ggctggctat   480
aagtgtcctg tggggaagaa aagaggttct ctgaggaggc cagcaagaac atctgtgtcc   540
caagtgccaa ggaacagcag tgtgaaatag tccagctgaa agcagaacat ggcacagacc   600
aggacatgat ctccctcaaa gagaagtgct ggaggaagag cactgagtgt gca           653

<210> SEQ ID NO 86
<211> LENGTH: 652
<212> TYPE: DNA
<213> ORGANISM: Mouse

<400> SEQUENCE: 86
cttcttcttg ggactcagaa tggtctcccc tgcccctggg ccatcaagta tgcaaattct    60
tttgtgttta cctatctgca gggtctgcta gaaatacttc aacccaaaat tccaaaatga   120
```

```
ccaagaagag atcaaaaata aatgaactag aagaactgaa attggatatg aggaagatca    180
gcaatgacat ggaggaaatg tgtggaatcc tgaacctta catgtatgag gatttgaact     240
acaggatgaa cactgaattc aacatcatta aatcacaaca tgagaagaca atgttggata    300
tgaataaaat gatccagtca ataattggtt ccatgcagta ctctaaggaa ctgatagaag    360
ataactattc ctacagcatt aaggaggacc acctcctccg tgagtgcact caactcaacg    420
aaaacgtaag gatattactg aatgagaaca aaggctgct ggtggagcag gctggccata    480
agtgtcctgt ggggaagaaa agaggttctc tgaggaggcc agcaagaaca tctgtgtccc    540
aagtgccaag gaacagcagt gtgatatagt ccagcagaaa gcagaacatg gcacagacca    600
cgacatgatc tccctcaaag agaagtgctg gaggaagagc actgagtgtg ca            652

<210> SEQ ID NO 87
<211> LENGTH: 784
<212> TYPE: DNA
<213> ORGANISM: Mouse

<400> SEQUENCE: 87
atgtgagatg gagcaggagc agtggctaaa tgttgaactc ttcaaaactt ggcttatggg     60
ctgctggtgt atcaccatca tccccaacac tcctgttcag aagatgggtg aggaaagtgg    120
aaagcctaac cactcagccg atgaccagtg gaaaaatga gctacaagat cacctgatct    180
tcatcagtga gaaagctttg cacaagaggg tctgctagaa atacttcaac ccaaaattcc    240
aaaatgacca agaagagatc aaaaataaat gaactagaag aactgaaatt ggatatgagg    300
aagatcagca atgacatgga ggaaatgtgt ggaatcctga accttttacat gtatgaggat    360 ttgaactaca ggatgaacac tgaattcaac atcattaaat cacaacatga aagacaatg    420 ttggatatga ataaaatgat ccagtccata attggttcca tgcagtactc caaggaactg    480
atagaagata ctattcctca gcattaagga ggaccacc tcctccgtga gtgcactcaa       540
ctcaacgaaa acgtaaggat attactgaat gagaacagaa ggctgctggt ggagcaggct    600
ggccataagt gtcctgtggg gaagaaaaga ggttctctga ggaggccagc aagaacatct    660
gtgtcccaag tgccaaggaa cagcagctaa gtgtgaaata gtccagctga agcagaaca     720 tggcacagac caggacatga tctccctcaa agagaagtgc tggaggaaga gcactgagtg    780
tgca                                                                  784

<210> SEQ ID NO 88
<211> LENGTH: 643
<212> TYPE: DNA
<213> ORGANISM: Mouse

<400> SEQUENCE: 88
tcttcttctt gggactcaga atggtctccc ctgcccctgg gccatcaagt atgcaaattc      60
ttttgtgttt acctatctgc agggtctgct agaaatactt caacccaaaa ttccaaaatg    120
actaagaaga gatcaaaaat aaatgaacta gaagaactga attggatat gaggaagatc     180 agcaatgaca tggaggaaat gtgtggaatc ctgaaccttt acatgtatga ggatttgaac    240
tacaggatga cactgaattc aacatcatt aaatcacaac atgagaagac aatgttggat     300
atgaataaaa tgatccagtc aataattggt tccatgcagt actctaagga actgatagaa    360
gataactatt cctacagcat taaggaggac cactcctcc gtgagtgcac tcaactccac     420
gaaaacgtaa ggatattact gaatgagaac agaaggctgc tggtggagca ggctggccac    480
```

| aagtgtcctg tggggaagaa aagaggttct ctgaggaggc cagcaagaac atctgtgtcc | 540 |
| caagtcccaa ggaacagcag tccagcagaa agcagaacat ggcacagacc aggacatgat | 600 |
| ctccctcaaa gagaagtgct ggaggaagag cactgagtgt gca | 643 |

<210> SEQ ID NO 89
<211> LENGTH: 650
<212> TYPE: DNA
<213> ORGANISM: Mouse

<400> SEQUENCE: 89

| aaggggatcc cacgggtcca tgagaggctc caggagaggc accccagaaa aggaccaagc | 60 |
| tgggcagaac tagttaacag ggtctgctag aaatacttca acccaaaatt ccaaaatgac | 120 |
| taagaagaga tcaaaaataa atgaactaga gaactgaaa ttggatatga ggaagatcag | 180 |
| caatgacatg gaggaaatgg gtggaatcct gaacctttac atgtatgagg atttgaacta | 240 |
| caggatgaac actgaattca acatcattaa atcacaacat gagaagacaa tgttggatat | 300 |
| gaataaaatg atccagtcaa taattggttc catgcagtac tctaaggaac tgatagaaga | 360 |
| taactattcc tacagcatta aggaggacca cctcctccgt gagtgcactc aactccacga | 420 |
| aaacgtaagg atattactga atgagaacag aaggctgctg gtggagcagg ctggccacaa | 480 |
| gtgtcctgtg ggaagaaaag tggttctctg aggaggccag caagaacatc tgtgtcccaa | 540 |
| gtgccaagga acagcagtgt gaaatagtcc agcagaaagc agaatatggc acagaccacg | 600 |
| acatgatctc cctcaaagag aggtgctgga ggaagagcac tgagtgtgca | 650 |

<210> SEQ ID NO 90
<211> LENGTH: 657
<212> TYPE: DNA
<213> ORGANISM: Mouse

<400> SEQUENCE: 90

| aagtctaatc agtcagccga tgaccagtgg gaaaaatgag ctacaagatc acctgatctt | 60 |
| catcagtgag aaagctttgc acaagagggt ctgctagaaa tacttcaacc caaaattcca | 120 |
| aaatgactaa gaagagatca aaaataaatg aactagaaga actgaaattg gatatgagga | 180 |
| agatcagcaa tgacatggag gaaatgtgtg gaatcctgaa cctttacatg tatgaggatt | 240 |
| tgaactacag gatgaacact gaattcaaca tcattaaatc acaacatgag aagacaatgt | 300 |
| tggatatgaa taaatgatc cagtccataa ttgtttccat gcagtactcc aaggaactga | 360 |
| tagaagataa ctattcctac agcattaagg aggaccacct cctccgtgag tgcactcaac | 420 |
| tcaacgaaaa cgtaaggata ttactgaatg agaacagaag gctgctggtg agcaggctg | 480 |
| gccataagtg tcctgtgggg aagaaaagag gttctctgag gaggccacaa gaacatctgt | 540 |
| gtcccaagtg ccaaggaaca gcagtgtgat atagtccagc agaaagcaga acatggcaca | 600 |
| gaccacgaca tgatctccct caaagagaag tgctggagga gagcactga gtgtgca | 657 |

<210> SEQ ID NO 91
<211> LENGTH: 150
<212> TYPE: PRT
<213> ORGANISM: Mouse

<400> SEQUENCE: 91

```
Met Thr Lys Lys Arg Ser Lys Ile Asn Glu Leu Glu Glu Leu Lys Leu
1               5                   10                  15
Asp Met Arg Lys Ile Ser Asn Asp Met Glu Glu Met Cys Gly Ile Leu
            20                  25                  30
```

Asn Leu Tyr Met Tyr Glu Asp Leu Asn Tyr Arg Met Asn Thr Glu Phe
                35                  40                  45

Asn Ile Ile Lys Ser Gln His Glu Lys Thr Met Leu Asp Met Asn Lys
     50                  55                  60

Met Ile Gln Ser Ile Ile Gly Ser Met Gln Tyr Ser Lys Glu Leu Ile
 65                  70                  75                  80

Glu Asp Asn Tyr Ser Tyr Ser Ile Lys Glu Asp His Leu Leu Arg Glu
                 85                  90                  95

Cys Thr Gln Leu Asn Glu Asn Val Arg Ile Leu Leu Asn Glu Asn Arg
                100                 105                 110

Arg Leu Leu Val Glu Gln Ala Gly Tyr Lys Cys Pro Val Gly Lys Lys
            115                 120                 125

Arg Gly Ser Leu Arg Arg Pro Ala Arg Thr Ser Val Ser Gln Val Pro
        130                 135                 140

Arg Asn Ser Ser Val Lys
145                 150

<210> SEQ ID NO 92
<211> LENGTH: 150
<212> TYPE: PRT
<213> ORGANISM: Mouse

<400> SEQUENCE: 92

Met Thr Lys Lys Arg Ser Lys Ile Asn Glu Leu Glu Glu Leu Lys Leu
 1               5                  10                  15

Asp Met Arg Lys Ile Ser Asn Asp Met Glu Glu Met Cys Gly Ile Leu
            20                  25                  30

Asn Leu Tyr Met Tyr Glu Asp Leu Asn Tyr Arg Met Asn Thr Glu Phe
                35                  40                  45

Asn Ile Ile Lys Ser Gln His Glu Lys Thr Met Leu Asp Met Asn Lys
     50                  55                  60

Met Ile Gln Ser Ile Ile Gly Ser Met Gln Tyr Ser Lys Glu Leu Ile
 65                  70                  75                  80

Glu Asp Asn Tyr Ser Tyr Ser Ile Lys Glu Asp His Leu Leu Arg Glu
                 85                  90                  95

Cys Thr Gln Leu Asn Glu Asn Val Arg Ile Leu Leu Asn Glu Asn Arg
                100                 105                 110

Arg Leu Leu Val Glu Gln Ala Gly His Lys Cys Pro Val Gly Lys Lys
            115                 120                 125

Arg Gly Ser Leu Arg Arg Pro Ala Arg Thr Ser Val Ser Gln Val Pro
        130                 135                 140

Arg Asn Ser Ser Val Ile
145                 150

<210> SEQ ID NO 93
<211> LENGTH: 148
<212> TYPE: PRT
<213> ORGANISM: Mouse

<400> SEQUENCE: 93

Met Thr Lys Lys Arg Ser Lys Ile Asn Glu Leu Glu Glu Leu Lys Leu
 1               5                  10                  15

Asp Met Arg Lys Ile Ser Asn Asp Met Glu Glu Met Cys Gly Ile Leu
            20                  25                  30

Asn Leu Tyr Met Tyr Glu Asp Leu Asn Tyr Arg Met Asn Thr Glu Phe
                35                  40                  45

```
Asn Ile Ile Lys Ser Gln His Glu Lys Thr Met Leu Asp Met Asn Lys
         50                  55                  60

Met Ile Gln Ser Ile Ile Gly Ser Met Gln Tyr Ser Lys Glu Leu Ile
 65                  70                  75                  80

Glu Asp Asn Tyr Ser Tyr Ser Ile Lys Glu Asp His Leu Leu Arg Glu
                 85                  90                  95

Cys Thr Gln Leu Asn Glu Asn Val Arg Ile Leu Leu Asn Glu Asn Arg
            100                 105                 110

Arg Leu Leu Val Glu Gln Ala Gly His Lys Cys Pro Val Gly Lys Lys
            115                 120                 125

Arg Gly Ser Leu Arg Arg Pro Ala Arg Thr Ser Val Ser Gln Val Pro
    130                 135                 140

Arg Asn Ser Ser
145

<210> SEQ ID NO 94
<211> LENGTH: 172
<212> TYPE: PRT
<213> ORGANISM: Mouse

<400> SEQUENCE: 94

Met Thr Lys Lys Arg Ser Lys Ile Asn Glu Leu Glu Glu Leu Lys Leu
  1               5                  10                  15

Asp Met Arg Lys Ile Ser Asn Asp Met Glu Glu Met Cys Gly Ile Leu
             20                  25                  30

Asn Leu Tyr Met Tyr Glu Asp Leu Asn Tyr Arg Met Asn Thr Glu Phe
         35                  40                  45

Asn Ile Ile Lys Ser Gln His Glu Lys Thr Met Leu Asp Met Asn Lys
         50                  55                  60

Met Ile Gln Ser Ile Ile Gly Ser Met Gln Tyr Ser Lys Glu Leu Ile
 65                  70                  75                  80

Glu Asp Asn Tyr Ser Tyr Ser Ile Lys Glu Asp His Leu Leu Arg Glu
                 85                  90                  95

Cys Thr Gln Leu His Glu Asn Val Arg Ile Leu Leu Asn Glu Asn Arg
            100                 105                 110

Arg Leu Leu Val Glu Gln Ala Gly His Lys Cys Pro Val Gly Lys Lys
            115                 120                 125

Arg Gly Ser Leu Arg Arg Pro Ala Arg Thr Ser Val Ser Gln Val Pro
    130                 135                 140

Arg Asn Ser Ser Pro Ala Glu Ser Arg Thr Trp His Arg Pro Gly His
145                 150                 155                 160

Asp Leu Pro Gln Arg Glu Val Leu Glu Glu His
                165                 170

<210> SEQ ID NO 95
<211> LENGTH: 131
<212> TYPE: PRT
<213> ORGANISM: Mouse

<400> SEQUENCE: 95

Met Thr Lys Lys Arg Ser Lys Ile Asn Glu Leu Glu Glu Leu Lys Leu
  1               5                  10                  15

Asp Met Arg Lys Ile Ser Asn Asp Met Glu Glu Met Gly Gly Ile Leu
             20                  25                  30

Asn Leu Tyr Met Tyr Glu Asp Leu Asn Tyr Arg Met Asn Thr Glu Phe
         35                  40                  45
```

```
Asn Ile Ile Lys Ser Gln His Glu Lys Thr Met Leu Asp Met Asn Lys
        50              55              60

Met Ile Gln Ser Ile Ile Gly Ser Met Gln Tyr Ser Lys Glu Leu Ile
65              70              75              80

Glu Asp Asn Tyr Ser Tyr Ser Ile Lys Glu Asp His Leu Leu Arg Glu
                85              90                  95

Cys Thr Gln Leu His Glu Asn Val Arg Ile Leu Leu Asn Glu Asn Arg
            100             105             110

Arg Leu Leu Val Glu Gln Ala Gly His Lys Cys Pro Val Gly Arg Lys
            115             120             125

Val Val Leu
        130

<210> SEQ ID NO 96
<211> LENGTH: 148
<212> TYPE: PRT
<213> ORGANISM: Mouse

<400> SEQUENCE: 96

Met Thr Lys Lys Arg Ser Lys Ile Asn Glu Leu Glu Glu Leu Lys Leu
1               5               10              15

Asp Met Arg Lys Ile Ser Asn Asp Met Glu Glu Met Cys Gly Ile Leu
            20              25              30

Asn Leu Tyr Met Tyr Glu Asp Leu Asn Tyr Arg Met Asn Thr Glu Phe
            35              40              45

Asn Ile Ile Lys Ser Gln His Glu Lys Thr Met Leu Asp Met Asn Lys
        50              55              60

Met Ile Gln Ser Ile Ile Val Ser Met Gln Tyr Ser Lys Glu Leu Ile
65              70              75              80

Glu Asp Asn Tyr Ser Tyr Ser Ile Lys Glu Asp His Leu Leu Arg Glu
                85              90                  95

Cys Thr Gln Leu Asn Glu Asn Val Arg Ile Leu Leu Asn Glu Asn Arg
            100             105             110

Arg Leu Leu Val Glu Gln Ala Gly His Lys Cys Pro Val Gly Lys Lys
            115             120             125

Arg Gly Ser Leu Arg Arg Pro Gln Glu His Leu Cys Pro Lys Cys Gln
            130             135             140

Gly Thr Ala Val
145
```

METHOD FOR SCREENING FOR COMPOUNDS THAT MODULATE P16 MEDIATED REGULATION OF NMDA RECEPTORS

RELATED APPLICATION

Benefit of priority under 35 U.S.C. 119(e) is claimed herein to U.S. Provisional Application No.: 60/494,017, filed Aug. 8, 2003. The disclosure of the above referenced application is incorporated by reference in its entirety herein.

STATEMENT REGARDING FEDERALLY SPONSORED RESEARCH

This invention was made in part with the United States government support under Grant Numbers P01 HD29587 and R01 EY05477 from the NIH\NICHD. The U.S. government may have certain rights in this invention.

FIELD OF THE INVENTION

This invention relates to the discovery of a novel protein, termed p16 and variants thereof, and the discovery that when expressed, p16 causes an increased efflux of cations through the NMDA receptor. The invention also relates to the discovery of novel nucleotide sequences that encode p16. The discovery of the current invention is useful for methods for diagnosing, treating and screening to identify agents useful for treating NMDA receptor dysregulation related diseases and pathological conditions and to compositions having an improved therapeutic profile identified using such screening methods.

BACKGROUND OF THE INVENTION

Ionotropic glutamate receptors activate ligand-gated cation channels that mediate the predominant component of excitatory neurotransmission in the central nervous system (CNS). These receptors have been classified based on their preference for the glutamate-like agonists (RS)-2-amino-3-(3-hydroxy-5-methyl-4-isoxazolyl)propionic acid (AMPA), kainate (KA), and N-methyl-D-aspartate (NMDA). All three glutamate receptor subtypes are heteromultimeric complexes, and many of the subunits that comprise them have been identified and characterized. To date, six NMDA receptor subunits (NR1, NR2A-2D and NR3A) have been reported.

The NMDA receptor (NMDAR) has unique properties distinguishing it from the other glutamate receptor subtypes. First, the activation of NMDAR requires the presence of dual agonists, glutamate (or NMDA) and glycine. The ligand-gated ion channel of the NMDA receptor is, thus, under the control of at least two distinct allosteric sites. In addition, the NMDA receptor controls the flow of both divalent ($Ca^{2+}$) and monovalent ($Na^+$, $K^+$) ions into the postsynaptic neural cell through a receptor associated channel. (Foster et al., "Taking apart NMDA receptors", Nature, 329:395-396, 1987; Mayer et al., "Excitatory amino acid receptors, second messengers and regulation of intracellular $Ca^{2+}$ in mammalian neurons," Trends in Pharmacol. Sci., 11:254-260, 1990). The activation of these receptors is regulated by $Mg^{2+}$ in a voltage-dependent manner (i.e., the NMDAR is blocked at resting membrane potential and activated when depolarized). Most importantly; however, the NMDAR is extremely permeable to $Ca^{2+}$, a key regulator of cell function.

NMDARs are believed to play a pivotal role in the transmission of excitatory signals from primary sensory neurons to the brain through the spinal cord (A. H. Dickenson (1990) Trends Pharmacol. Sci., 11. 307-309). NMDA receptors mediate $Ca^{2+}$ influx into neurons, and its receptor-gated channel activity is blocked by $Mg^{2+}$ in a voltage-dependent manner. These unique properties allow NMDARs to play a critical role in development of the nervous system, synaptic plasticity, memory, and other physiological processes in the CNS.

However, excessive stimulation of NMDARs has also been implicated in many pathological conditions including stroke, ischemia, head and spinal trauma, headache, epilepsy, neuropathic pain syndromes including diabetic neuropathy, glaucoma, depression and anxiety, drug addiction/withdrawal/tolerance, and in chronic neurodegenerative states, such as Alzheimer's disease, Huntington's disease, HIV-associated dementia, Parkinson's disease, multiple sclerosis, and amyotrophic lateral sclerosis (ALS).

The molecular cloning and functional analysis of expressed NMDAR subunits, coupled with the examination of their temporal and spatial expression patterns in vivo, has led to significant advances in our understanding of NMDAR function at the molecular level. However, the identification of these subunits alone has failed to explain the observed diversity in NMDAR function, particularly in motor neurons. Thus there is a need to further understand the role of NMDAR subunits in regulating these diverse functions.

Due to its broad-spectrum of neurological involvement, yet non-universal distribution, investigators are interested in the identification and development of drugs acting at the NMDA receptor. Drugs acting on the NMDA receptor are, therefore, expected to have enormous therapeutic potential. For instance, U.S. Pat. No. 4,904,681, issued to Cordi et al. (Cordi I), describes the use of D-Cycloserine, which was known to modulate the NMDA receptor, to improve/enhance memory and to treat cognitive deficits linked to a neurological disorder. D-Cycloserine is described as a glycine agonist which binds to the strychnine-insensitive glycine receptor.

U.S. Pat. No. 5,061,721, issued to Cordi et al. (Cordi II), describes the use of a combination of D-cycloserine and D-alanine to treat Alzheimer's disease, age-associated memory impairment, learning deficits, and psychotic disorders, as well as to improve memory or learning in healthy individuals.

U.S. Pat. No. 5,086,072, issued to Trullas et al., describes the use of 1-aminocyclopropanecarboxylic acid (ACPC), which was known to modulate the NMDA receptor as a partial agonist of the strychnine-insensitive glycine binding site, to treat mood disorders including major depression, bipolar disorder, dysthymia and seasonal effective disorder. It is also therein described that ACPC mimics the actions of clinically effective antidepressants in animal models. In addition, a copending U.S. patent application is cited that describes that ACPC and its derivatives may be used to treat neuropharmacological disorders resulting from excessive activation of the NMDA receptor.

None of the foregoing offers, however, a satisfactory mechanism for modulating NMDA receptor function. Development of drugs targeting the NMDA receptor, although desirous, has been hindered because the molecular pathway surrounding the NMDA receptor has not yet been completely elucidated. As mentioned above, the NMDAR consists of several protein chains (subunits) embedded in the postsynaptic membrane. Subunits NR1A and NR2A-D from a large extracellular region which probably contains most of the allosteric binding sites, several transmembrane regions looped and folded to form a pore or channel which is permeable to Ca.sup.2+, and a carboxyl terminal region. It is believed that the channel is in constant motion, alternating between a cation passing (open) and a cation blocking (closed) state. The opening and closing of the channel is regulated by the binding of various ligands to domains of the protein residing on the extracellular surface and separate from the channel. As such, these ligands are all known as allosteric ligands. The binding of two co-agonist ligands—glycine and glutamate—is thought to effect a conformational change in the overall structure of the protein which is ultimately reflected in the channel opening, partially opening, partially closing, or closing. The binding of other allosteric ligands modulates the conformational change caused or effected by glutamate and glycine. The recently characterized subunit NR3A has been found to act in a novel manner, as compared to subunits NR1A-2D. NR3A downmodulates the NMDAR and this downmodulation has been correlated with a decreased unitary current and Ca.sup.2+ permeability of the channel. This unique regulatory behavior associated with the NR3A subunit is believed to have therapeutic importance. For example, studies in mice have shown that the NR3A subunit may protect the young nervous system from excitotoxic damage during development. Thus, it is desirable to further understand the NR3A molecular pathway, thereby allowing for the discovery of therapeutic compounds that modulate this same pathway.

SUMMARY OF THE INVENTION

NR3A represents a dominant-interfering subunit of the conventional NMDA receptors (Das et al., Nature 393:377). NR3A expression is developmentally regulated, with its peak expression occurring during the first two weeks after birth. NR3A expression persists into adulthood at low levels in restricted areas of the brain. Neurons in NR3A knockout mice manifest increased NMDA-induced currents. Therefore, these mice allow us to identify signal transduction pathways downstream to NMDAR hyperactivation. To this end, Inventors identified genes whose expression is altered in NR3A-deficient brains using gene microarrays. Briefly, mRNAs were extracted from WT and NR3A-KO brains at postnatal day 15, and genes that displayed different levels of expression between the two samples were identified. Differential expression of these candidate genes was confirmed using real-time PCR and in situ hybridization. One gene identified in this manner encodes an ORF of 150 amino acids, representing a protein with a predicted MW of 16 kD. This gene was tentatively designated p16. Interestingly, p16 expression was up-regulated in NR3A-KO brains. As expected, up-regulation of p16 occurred in brain areas where NR3A expression is usually observed. These areas included the hippocampus; layer V of the cerebral cortex; and the amygdala. Exogenous p16 was then overexpressed in cultured cortical and hippocampal neurons. In the transfected neurons, Inventors observed that p16 protein was localized at synapses, and resulted in an increase in NMDA- but not AMPA- or GABA-induced currents. Intrestingly, p16 is a member of a large gene family. Based on the analysis of the mouse genome sequence, the estimated number of the gene family is 40-60. This gene family was named Takusan; however, in this current document the term "p16" will be used regardless of the actual molecular weight of the gene products. At least 32 different variants of p16 are expressed in the mouse brain. In addition, it is herein demonstrated that p16 can dimerize itself in cells, and, furthermore, select variants of p16 bind to PSD-95, a protein known to associate with NMDAR subunit 2 (NR2), while other variants do not. Therefore, there is a functional diversity among p16 variants.

Thus, the invention provides nucleotide sequences and amino acid sequences encoding and forming p16 and the variants thereof (hereinafter "p16"). The invention also provides methods for diagnosing and treating abnormalities in the p16:NMDAR molecular pathway. In addition, the invention provides a method of screening for modulators of said pathway which will increase or decrease signaling through an NMDA receptor. In a still further embodiment the invention provides a method of modulating NMDA receptor dysregulation associated with p16 using agents including, but not limited to, peptides, nucleic acids, small molecules and antibodies.

In one embodiment, the invention provides a method of modulating a cellular response to glycine or glutamate by introducing a nucleic acid molecule encoding a p16 polypeptide or functional fragment into a cell, and expressing the p16 functional fragment encoded by the nucleic acid molecule in the cell. In another embodiment, the invention provides a method of modulating a cellular response to glycine or glutamate by introducing an antisense nucleic acid molecule, a ribozyme molecule or a small interfering RNA (siRNA) molecule into the cell, wherein the molecule hybridizes to a p16 nucleic acid molecule and prevents translation of the encoded p16 polypeptide.

BRIEF DESCRIPTION OF THE DRAWINGS

FIGS. 4a and 4b. From the 90 cDNA clones amplified by RT-PCR of the C57BL/6 WT mouse brain (male, 6 week old); 34 variants of p16-related proteins were identified. FIG. 4a shows these 34 amino-acid sequences, (SEQ ID Nos.: 4 through 37). In FIG. 4a, amino acid sequences are aligned against each other for comparison and, thus, are shown in 3 parts; line 1 of 3, line 2 of 3 and line 3 of 3. The nucleotide sequences for all clones are shown in FIG. 4b, (SEQ ID Nos.: 38 through 71). In FIG. 4b, the nucleotide sequences are again aligned for comparison, and, thus, must again be shown in parts. Due to the size of the nucleotide sequences there are 18 parts.

DETAILED DESCRIPTION OF THE INVENTION

Figure 1:
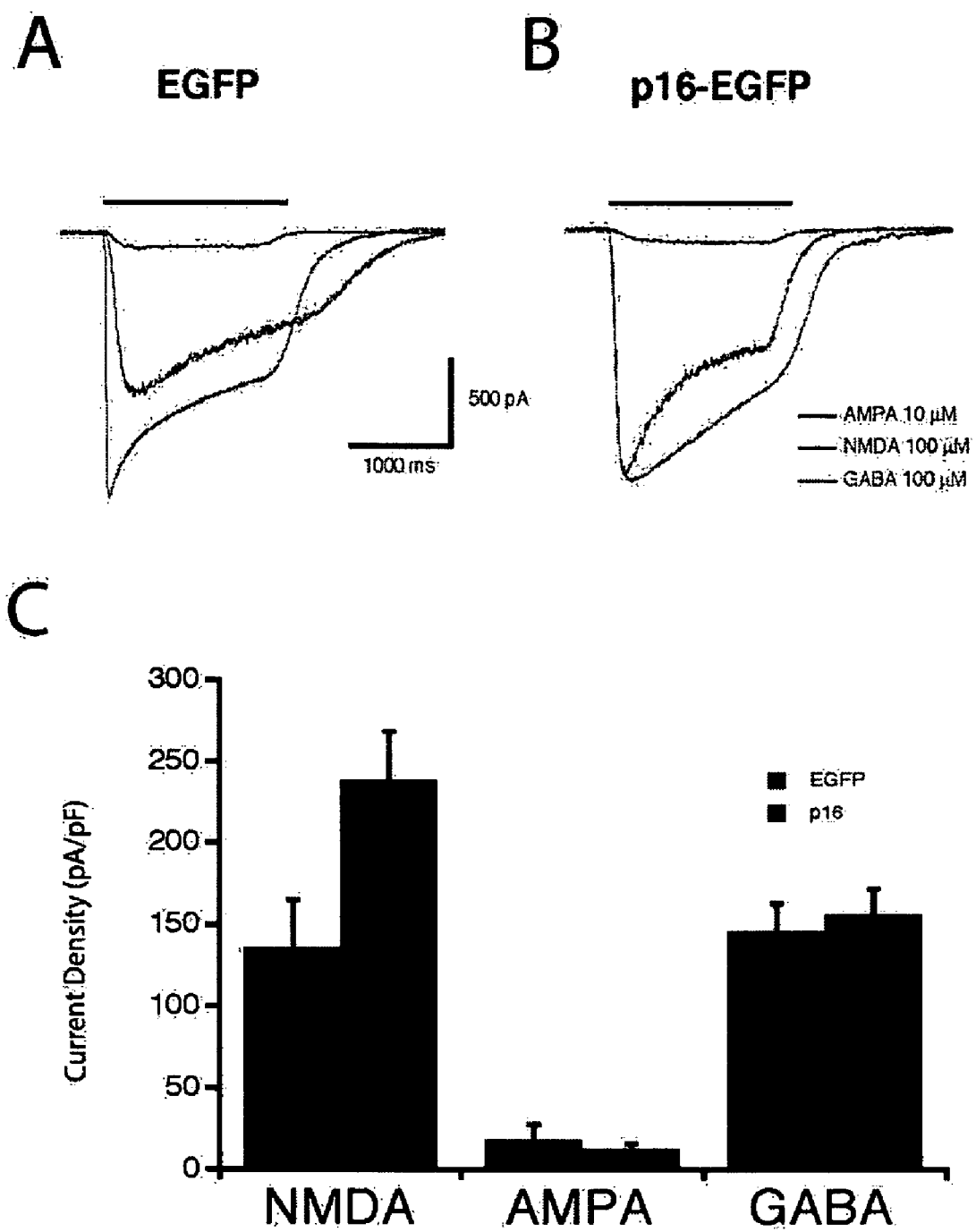
FIGS. 1a, 1b and 1c. Expression of p16 enhances NMDA currents in cultured hippocampal neurons. Representative NMDA, AMPA, and GABA currents from a control neuron (EGFP) and a neuron containing p16 (p16-EGFP) are shown in FIGS. 1a and 1b. NMDA, AMPA and GABA current densities in p16-EGFP neurons is shown in FIG. 1c.

Definitions:

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

As used herein, the terms "polypeptide" and "polypeptides" refer to a genus of polypeptide or peptide fragments that encompass the amino acid sequences identified herein, as well as smaller fragments. Alternatively, a polypeptide may be defined in terms of its antigenic relatedness to any peptide encoded by the nucleic acid sequences of the invention. Thus, in one embodiment, a polypeptide within the scope of the invention is defined as an amino acid sequence comprising a linear or 3-dimensional epitope shared with any peptide encoded by the nucleic acid sequences of the invention. Alternatively, a polypeptide within the scope of the invention is recognized by an antibody that specifically recognizes any peptide encoded by the nucleic acid sequences of the invention.

As used herein, the term "isolated," in reference to polypeptides or proteins, means that the polypeptide or protein is substantially removed from polypeptides, proteins, nucleic acids, or other macromolecules with which it, or its analogues, occurs in nature. Although the term "isolated" is not intended to require a specific degree of purity, typically, the protein will be at least about 75% pure, more typically at least about 90% pure, preferably at least about 95% pure, and more preferably at least about 99% pure.

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general references which are provided throughout this document, as well as: Maniatis et al., Molecular Cloning: A Laboratory Manual (1989), 2nd Ed., Cold Spring Harbor, N.Y.; and Berger and Kimmel, Methods in Enzymology, Volume 152, Guide to Molecular Cloning Techniques (1987), Academic Press, Inc., San Diego, Calif., which are incorporated herein by reference. Oligonucleotides can be synthesized on an Applied Bio Systems oligonucleotide synthesizer according to specifications provided by the manufacturer. The procedures are believed to be well known in the art and are provided for the convenience of the reader. All the information contained therein is incorporated herein by reference.

As used herein, the term "agonist" refers to an agent which produces activation of p16 and provides for a substantial increase in NMDAR activation.

As used herein, the term "antagonist" refers to an agent which opposes the agonist activity of a known agonist of p16.

The term "candidate compound" refers to any molecule that potentially acts as a ligand, agonist or antagonist in the screening methods disclosed herein. A candidate compound can be a naturally occurring macromolecule, such as a polypeptide, amino acid, nucleic acid, carbohydrate, lipid, or any combination thereof. A candidate compound also can be a partially or completely synthetic derivative, analog or mimetic of such a macromolecule, or a small organic molecule prepared by combinatorial chemistry methods. If desired in a particular assay format, a candidate compound can be detectably labeled or attached to a solid support.

Methods for preparing large libraries of compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., Curr. Opin. Chem. Biol. 2:422-428 (1998); Tietze et al., Curr. Biol., 2:363-371 (1998); Sofia, Mol. Divers. 3:75-94 (1998); Eichler et al., Med. Res. Rev. 15:481-496 (1995); and the like. Libraries containing large numbers of natural and synthetic compounds also can be obtained from commercial sources.

The number of different candidate compounds to test in the methods of the invention will depend on the application of the method. For example, one or a small number of candidate compounds can be advantageous in manual screening procedures, or when it is desired to compare efficacy among several predicted ligands, agonists or antagonists. However, it is generally understood that the larger the number of candidate compounds, the greater the likelihood of identifying a compound having the desired activity in a screening assay. Additionally, large numbers of compounds can be processed in high-throughput automated screening assays. Therefore, "one or more candidate compounds" can be, for example, 2 or more, such as 5, 10, 15, 20, 50 or 100 or more different compounds, such as greater than about 103, 105 or 107 different compounds, which can be assayed simultaneously or sequentially The term "detectable label" refers to any moiety that can be selectively detected in a screening assay. Examples include without limitation, radiolabels, (e.g., $^3H$, $^{14}C$, $^{35}S$, $^{125}I$, $^{131}I$), affinity tags (e.g. biotin/avidin or streptavidin, binding sites for antibodies, metal binding domains, epitope tags, FLASH binding domains—See U.S. Pat. Nos. 6,451,569; 6,054,271; 6,008,378 and 5,932,474—glutathione or maltose binding domains) fluorescent or luminescent moieties (e.g. fluorescein and derivatives, GFP, rhodamine and derivatives, lanthanides etc.), and enzymatic moieties (e.g. horseradish peroxidase, $\beta$-galactosidase, $\beta$-lactamase, luciferase, alkaline phosphatase). Such detectable labels can be formed in situ, for example, through use of an unlabeled primary antibody which can be detected by a secondary antibody having an attached detectable label.

The methods of detecting a p16 nucleic acid molecule or peptide in a sample can be either qualitative or quantitative, and can detect the presence, abundance, integrity or structure of the nucleic acid molecule, as desired for a particular application. Suitable hybridization-based assay methods include, for example, in situ hybridization, Northern blots, RNase protection assays, Western blots and Southern blots, which can be used to determine the copy number and integrity of DNA. A hybridization probe can be labeled with any suitable detectable moiety such as those listed directly above. These methods are well known to those of ordinary skill in the art.

The term "DNA binding domain" or "DBD" refers to protein domain capable of binding to a specific DNA sequence, and comprising at least one zinc finger sequence.

The term "functional fragment" refers to a portion of a full-length p16 polypeptide that retains at least one biological activity characteristic of the full-length polypeptide. A functional fragment can contain, for example, at least about 6, 8, 10, 12, 15, 20, 25, 30, 35, 40, 50, 60, 70, 80, 90, 100, 110, 125, 150, 200 or more amino acids of a polypeptide. The remaining amino acid sequence is identical to, or exhibits substantial identity to, the corresponding positions in the naturally-occurring sequence.

As used herein, the term "functionally expressed" refers to a coding sequence which is transcribed, translated, post-translationally modified (if relevant), and positioned in a cell such that the protein provides the desired function. With reference to a reporter cassette, functional expression generally means production of a sufficient amount of the encoded cell surface reporter protein to provide a statistically significant detectable signal to report transcriptional effects of a reporter polynucleotide.

As used herein, the term "LBD" or "ligand-binding domain" refers to the protein domain of a receptor, such as a NMDA receptor or other suitable receptor as discussed herein, which binds a physiological ligand and thereupon undergoes a conformational change and/or altered intermolecular interaction with an associated protein so as to confer a detectable activity.

As used herein, the term "ligand" refers to any biological or chemical compound that binds the recited polypeptide, fragment or receptor with high affinity. High affinity binding refers to binding with a Kd of less than about $10^{-3}$ M, such as less than $10^{-5}$ M, and often less than $10^{-7}$ M. p16 antibodies are examples of ligands of p16. As used herein, antibodies are defined to be "specifically binding" to a polypeptide if they bind polypeptides of the current invention with a $K_a$ of greater than or equal to about $10^7$ times $M^{-1}$.

A "p16 ligand" can further be an agonist or antagonist of p16, as described below, or can be a compound having little or no effect on p16 biological activity. For example, a ligand without agonistic or antagonistic activity can be used to specifically target a diagnostic or therapeutic moiety to cells and tissues that express an excitatory glycine receptor. Thus, an identified ligand can be labeled with a detectable moiety, such as a radiolabel, fluorochrome, ferromagnetic substance, or luminescent substance, and used to detect normal or abnormal expression of an excitatory glycine receptor in an isolated sample or in in vivo diagnostic imaging procedures. Likewise, an identified ligand can be labeled with a therapeutic moiety, such as a cytotoxic or cytostatic agent or radioisotope, and administered in an effective amount to arrest proliferation or kill a cell or tissue that aberrantly expresses an excitatory glycine receptor for use in therapeutic applications described further below.

Binding assays, including high-throughput automated binding assays, are well known in the art and can be used in the invention methods. The assay format can employ a cell, cell membrane, artificial membrane system, or purified polypeptide, fragment or receptor, either in solution or attached to a solid phase. If desired, the binding assay can be performed in the presence of a known ligand of p16.

Suitable assays that can be used for detecting ligand binding include, for example, scintillation proximity assays (SPA) (Alouani, Methods Mol. Biol. 138:135-41 (2000)), UV or chemical cross-linking (Fancy, Curr. Opin. Chem. Biol. 4:28-33 (2000)), competition binding assays (Yamamura et al., Methods in Neurotransmitter Receptor Analysis, Raven Press, New York, 1990), biomolecular interaction analysis (BIA) (Weinberger et al., Pharmacogenomics 1:395-416 (2000)), mass spectrometry (MS) (McLafferty et al., Science 284:1289-1290 (1999) and Degterev, et al., Nature Cell Biology 3:173-182 (2001)), nuclear magnetic resonance (NMR) (Shuker et al., Science 274:1531-1534 (1996), Hajduk et al., J. Med. Chem. 42:2315-2317 (1999), and Chen and Shapiro, Anal. Chem. 71:669A-675A (1999)), fluorescence polarization assays (FPA) (Degterev et al., supra, 2001); surface plasmon resonance (SPR)(Liparoto et al., J. Mol Recognit. 12:316-321 (1999)); protein chip proteomic array analysis (e.g. ProteinChip™ System from Ciphergen Biosystems, which can be used in tandem with mass spectrometry analysis for sequence or structure determination), and in silico screening, whereby a library of compounds are screened using a computer based platform for an efficient method for filtering large virtual compound libraries.

An exemplary assay that has been used successfully to identify ligands of an NMDA receptor is phage display (see Li et al., Nature Biotech. 14:986-991 (1996)). A similar phage display approach can be applied to determine p16 ligands and excitatory glycine receptor ligands.

Exemplary high-throughput receptor binding assays are described, for example, in Mellentin-Micelotti et al., Anal. Biochem. 272:P182-190 (1999); Zuck et al., Proc. Natl. Acad. Sci. USA 96:11122-11127 (1999); and Zhang et al., Anal. Biochem. 268:134-142 (1999). Other suitable methods are well known in the art.

As used herein, "linked" means in polynucleotide linkage (i.e., phosphodiester linkage) or polypeptide linkage, depending upon the context of usage. "Unlinked" means not linked to another polynucleotide or polypeptide sequence; hence, two sequences are unlinked if each sequence has a free 5' terminus and a free 3' terminus.

As used herein, the term "modulator" refers to a wide range of candidate compounds, including, but not limited to natural, synthetic or semi-synthetic organic molecules, proteins, oligonucleotides and antisense, that directly or indirectly influence the activity of the p16 and or NR3A pathway. Furthermore, the precursor of a modulator (i.e., a compound that can be converted into a modulator) is also considered to be a modulator. Similarly, a compound which converts a precursor into a modulator is also considered to be a modulator.

"Naturally fluorescent protein" refers to proteins capable of forming a highly fluorescent, intrinsic chromophore either through the cyclization and oxidation of internal amino acids within the protein or via the enzymatic addition of a fluorescent co-factor. Typically such chromophores can be spectrally resolved from weakly fluorescent amino acids such as tryptophan and tyrosine. Endogenously fluorescent proteins have been isolated and cloned from a number of marine species including the sea pansies *Renilla reniformis*, *R. kollikeri* and *R. mullerei* and from the sea pens *Ptilosarcus*, *Stylatula* and *Acanthoptilum*, as well as from the Pacific Northwest jellyfish, *Aequorea victoria*; Szent-Gyorgyi et al. (SPIE conference 1999), D.C. Prasher et al., Gene, 111:229-233 (1992) and red and yellow fluorescent proteins from coral. A variety of mutants of the GFP from *Aequorea Victoria* have been created that have distinct spectral properties, improved brightness and enhanced expression and folding in mammalian cells compared to the native GFP, (*Green Fluorescent Proteins*, Chapter 2, pages 19 to 47, edited Sullivan and Kay, Academic Press, U.S. Pat. No. 5,625,048 to Tsien et al., issued Apr. 29, 1997; U.S. Pat. No. 5,777,079 to Tsien et al., issued Jul. 7, 1998; and U.S. Pat. No. 5,804,387 to Cormack et al., issued Sep. 8, 1998). In many cases these functional engineered fluorescent proteins have superior spectral properties to wild-type proteins and are preferred for use as reporter genes in the present invention. Preferred naturally fluorescent proteins include without limitation, EGFP, YFP, Renilla GFP and DS red.

The terms "nucleotide sequence" "nucleic acid" or "nucleic acid molecule," as used herein, refer to a deoxyribonucleotide or ribonucleotide polymer in either single-ordouble-stranded form, and unless otherwise limited, would fully encompass known analogs of natural nucleotides that can function in a similar manner as naturally occurring nucleotides.

Accordingly, a designated sequence identifier, unless specified otherwise, is intended to refer to the single-stranded molecule having the recited sequence, the single-stranded complement of the recited sequence, or a double stranded (or partially double-stranded) molecule in which one strand has the recited sequence. A nucleic acid molecule can optionally include one or more non-native nucleotides, having, for example, modifications to the base, the sugar, or the phosphate portion, or having a modified phosphodiester linkage. Such modifications can be advantageous in increasing the stability of the nucleic acid molecule. Furthermore, a nucleic acid molecule can include, for example, a detectable moiety, such as a radiolabel, a fluorochrome, a ferromagnetic substance, a luminescent tag or a detectable binding agent such as biotin. Such modifications can be advantageous in applications where detection of a hybridizing nucleic acid molecule is desired.

Some of the nucleic acid molecules of the present invention are derived from DNA or RNA isolated at least once in substantially pure form and in a quantity or concentration enabling identification, manipulation, and recovery of its component nucleotide sequence by standard biochemical methods. Examples of such methods, including methods for PCR, RT-PCR, SSCP analysis and coupled PCR transcription and translation analysis protocols that may be used herein, are disclosed in Sambrook et al. Molecular Cloning: A Laboratory Manual, 2nd ed., Cold Spring Harbor Laboratory Press, New York (1989), Ausubel, F. A., et al., eds., Current Protocols in Molecular Biology, John Wiley and Sons, Inc., New York (1987), and Innis, M., et al. (Eds.) PCR Protocols: A Guide to Methods and Applications, Academic Press, San Diego, Calif. (1990). Reference to a nucleic acid molecule also includes its complement as determined by the Standard Watson-Crick base-pairing rules, with Uracil (U) in RNA replacing Thymine (T) in DNA, unless the complement is specifically excluded.

As used herein, the nucleic acid molecules of the invention include DNA in both single-stranded and double-stranded form, as well as the DNA or RNA complement thereof (e.g., sense or antisense). DNA includes, for example, DNA, genomic DNA, chemically synthesized DNA, DNA amplified by PCR, and various combinations thereof. Genomic DNA, including translated, non-translated and control regions, may be isolated by conventional techniques, e.g., using any one of the cDNAs of the invention, or suitable fragments thereof, as a probe to identify a piece of genomic DNA which can then be cloned using methods commonly known in the art.

Polypeptides encoded by the nucleic acids of the invention are fully encompassed by the invention. As used herein, reference to a nucleic acid "encoding" a protein or a polypeptide encompasses not only cDNAs and other intronless nucleic acids, but also DNAs, such as genomic DNA, with introns, on the assumption that the introns included have appropriate splice donor and acceptor sites that will ensure that the introns are spliced out of the corresponding transcript when the transcript is processed in a eukaryotic cell. Due to the degeneracy of the genetic code, wherein more than one codon can encode the same amino acid, multiple DNA sequences can code for the same polypeptide. Such variant DNA sequences can result from genetic drift or artificial manipulation, such as occurring during PCR amplification or as the product of deliberate mutagenesis of a native sequence. Deliberate mutagenesis of a native sequence can be carried out using numerous techniques well known in the art. For example, oligonucleotide-directed site-specific mutagenesis procedures can be employed, particularly where it is desired to mutate a gene such that predetermined restriction nucleotides or codons are altered by substitution, deletion, or insertion. Exemplary methods of making such alteration are disclosed by Walder et al. (Gene 42:133, 1986); Bauer et al. (Gene 37:73, 1985); Craik (BioTechniques, Jan. 12-19, 1985); Smith et al. (Genetic Engineering: Principles and Methods, Plenum Press, 1981); Kunkel (Proc. Natl. Acad. Sci. USA 82:488, 1985); Kunkel et al. (Methods in Enzymol. 154:367, 1987). The present invention thus fully encompasses any nucleic acid capable of encoding a protein of the current invention.

As used herein, the term "variant" refers to a polypeptide substantially homologous to a native polypeptide, but which has an amino acid sequence different from that encoded by any of the nucleic acid sequences of the invention because of one or more deletions, insertions or substitutions. Variants may be naturally occurring or artificially constructed. Variants can comprise conservatively substituted sequences, meaning that a given amino acid residue is replaced by a residue having similar physiochemical characteristics. See Zubay, Biochemistry, Addison-Wesley Pub. Co., (1983).

It is a well-established principle of protein and peptide chemistry that certain amino acids substitutions, entitled "conservative" amino acid substitutions, can frequently be made in a protein or a peptide without altering either the confirmation or the function of the protein or peptide. Such changes include substituting any of isoleucine (I), valine (V), and leucine (L) for any other of these amino acids; aspartic acid (D) for glutamic acid (E) and vice versa; glutamine (Q) for asparagine (N) and vice versa; and serine (S) for threonine (T) and vice versa.

The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments.

The effects of such substitutions can be calculated using substitution score matrices such as PAM120, PAM-200, and PAM-250 as discussed in Altschul, (J. Mol. Biol. 219:55565 (1991)). Other such conservative substitutions, for example, substitutions of entire regions having similar hydrophobicity characteristics, are well known.

Naturally-occurring and artificially constructed peptide variants are also encompassed by the present invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

As used herein, the term "splice variant" refers to a polypeptide generated from one of several RNA transcripts resulting from splicing of a primary transcript. Naturally-occurring and artificially constructed peptide splice variants are also encompassed by the present invention.

As used herein, the terms "hybridization" and "in situ hybridization" refer to conditions and washes under which nucleotide sequences that are significantly identical or homologous to each other remain bound to each other. Appropriate hybridization conditions can be selected by those skilled in the art with minimal experimentation as exemplified in Ausubel, F. A., et al., eds., Current Protocols in Molecular Biology Vol. 2, John Wiley and Sons, Inc., New York (1995). Additionally, stringency conditions are described in Sambrook et al. Molecular Cloning: A Laboratory Manual, 2nd ed., Cold Spring Harbor Laboratory Press, New York (1989). Variations on the conditions for low, moderate, and high stringency are well known in the art and may be used with the current invention.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence using the coding sequence as a template. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous. A structural gene (e.g., a HSV tk gene) which is operably linked to a polynucleotide sequence corresponding to a transcriptional regulatory sequence of an endogenous gene is generally expressed in substantially the same temporal and specific pattern as is the naturally-occurring gene. Methods for operatively linking a nucleic acid to a desired promoter are well known in the art and include, for example, cloning the nucleic acid into a vector containing the desired promoter, or appending the promoter to a nucleic acid sequence using PCR.

A vector of the invention can include a variety of elements useful for cloning and/or expression of the encoded nucleic acid molecule in the desired host cell, such as promoter and/or enhancer sequences, which can provide for constitutive, inducible or cell-specific RNA transcription; transcription termination and RNA processing signals, including polyadenylation signals, which provide for stability of a transcribed mRNA sequence; an origin of replication, which allows for proper episomal replication; selectable marker genes, such as a neomycin or hygromycin resistance gene, useful for selecting stable or transient transfectants in mammalian cells, or an ampicillin resistance gene, useful for selecting transformants in prokaryotic cells; and versatile multiple cloning sites for inserting nucleic acid molecules of interest.

Cloning vectors of the invention include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art.

Thus, an invention nucleic acid molecule operatively linked to a promoter can be used to express p16 transcripts and polypeptides in a desired host cell, or in an in vitro system, such as an extract or lysate that supports transcription and translation.

For use in the gene therapy applications described further below, a nucleic acid molecule of the invention can be incorporated into suitable gene therapy vector, such as a viral vector or plasmid. Viral based vectors are advantageous in being able to introduce relatively high levels of a heterologous nucleic acid into a variety of cells, including nondividing cells.

Suitable viral vectors for gene therapy applications are well known in the art, and include, for example, Herpes simplex virus vectors (U.S. Pat. No. 5,501,979), Vaccinia virus vectors (U.S. Pat. No. 5,506,138), Cytomegalovirus vectors (U.S. Pat. No. 5,561,063), Modified Moloney murine leukemia virus vectors (U.S. Pat. No. 5,693,508), adenovirus vectors (U.S. Pat. Nos. 5,700,470 and 5,731,172), adeno-associated virus vectors (U.S. Pat. No. 5,604,090), constitutive and regulatable retrovirus vectors (U.S. Pat. Nos. 4,405,712; 4,650,764 and 5,739,018, 5,646,013, 5,624,820, 5,693,508 and 5,674,703), papilloma virus vectors (U.S. Pat. Nos. 5,674,703 and 5,719,054), lentiviral vectors (Kafri et al., Mol. Ther. 1:516-521 (2000), and the like. For targeting neural cells in the treatment of neuronal diseases, adenoviral vectors, Herpes simplex virus vectors and lentiviral vectors are particularly useful.

For gene therapy applications, the nucleic acid molecule can be administered to a subject by various routes. For example, local administration at the site of a pathology can be advantageous because there is no dilution effect and, therefore, the likelihood that a majority of the targeted cells will be contacted with the nucleic acid molecule is increased. This is particularly true in the eye, where either intravitreal or intraretinal administration is possible. In addition, administration can be systemic, such as via intravenous or subcutaneous injection into the subject. For example, following injection, viral vectors will circulate until they recognize host cells with the appropriate target specificity for infection.

Receptor-mediated DNA delivery approaches also can be used to deliver a nucleic acid molecule into cells in a tissue-specific manner using a tissue-specific ligand or an antibody that is non-covalently complexed with the nucleic acid molecule via a bridging molecule. Direct injection of a naked nucleic acid molecule or a nucleic acid molecule encapsulated, for example, in cationic liposomes also can be used for stable gene transfer into non-dividing or dividing cells. In addition, a nucleic acid molecule can be transferred into a variety of tissues using the particle bombardment method.

Contemplated promoters and expression vectors provide for expression in bacterial cells, yeast cells, insect cells, amphibian cells, plant cells, mammalian cells (including human, non-human primate and rodent cells) and other vertebrate cells. A variety of promoters and expression vectors suitable for such purposes are commercially available, and can be further modified, if desired, to include appropriate regulatory elements to provide for the desired level of expression or replication in the host cell.

A "reporter gene" includes any gene that directly or indirectly produces a specific reporter gene product, detectable label, enzymatic moiety, or cellular phenotype, such as drug resistance that can be used to monitor transcription of that gene. Preferred reporter genes include proteins with an enzymatic activity that provides enzymatic amplification of gene expression such as .beta.-lactamase, luciferase, .beta.-galactosidase, catalytic antibodies and alkaline phosphatase. Other reporter genes include proteins such as naturally fluorescent proteins or homologs thereof, cell surface proteins or the native or modified forms of an endogenous gene to which a specific assay exists or can be developed in the future. Preferred reporter genes for use in the present invention provide for multiplexed analysis.

As used herein, the term "sample" is intended to mean any biological fluid, cell, tissue, organ or portion thereof that contains or potentially contains a p16 nucleic acid molecule or polypeptide. For example, a sample can be a histologic section of a specimen obtained by biopsy, or cells that are placed in or adapted to tissue culture. A sample further can be a subcellular fraction or extract, or a crude or substantially pure nucleic acid or protein preparation. A sample can be prepared by methods known in the art suitable for the particular format of the detection method employed.

As used herein, the phrase "system" refers to an intact organism or a cell-based system containing the various components required for analyzing the p16, NR3A and or p16/NR3A cellular pathway in response to the test compounds described herein.

The term "serial analysis" means that a test compound is analyzed and ranked based on a single activity. For example, compounds selected based solely on binding affinity, efficacy, ability to promote co-activator recruitment, ability to cause co-repressor dissociation or any other single factor, without reference to any other assay result or characteristic, are considered for the purposes here to be subject to "serial analysis." A compound may be subject to multiple rounds of serial analysis, each round being based on data created from a single activity. For purposes here this analysis strategy is not considered to be equivalent to parallel analysis so long as each analysis or ranking step is completed independently of each other.

The phrases "substantially identical," "substantial identity," "substantially similar" or "substantial similarity" mean that a relevant sequence is at least 70%, 75%, 80%, 85%, 90%, 92%, 95% 96%, 97%, 98%, or 99% identical to a given sequence. By way of example, such sequences may be allelic variants, sequences derived from various species, sequences derived from various loci within the same species, or they may be derived from the given sequence by truncation, deletion, amino acid substitution or addition. Percent identity between two sequences is determined by standard alignment algorithms such as ClustalX, GAP or BESTFIT when the two sequences are in best alignment according to the alignment algorithm. Preferably, residue positions which are not identical differ by conservative amino acid substitutions. Conservative amino acid substitutions refer to the interchangeability of residues having similar side chains.

"Treating" or "treatment" as used herein covers the treatment of a disease-state associated with activity as disclosed herein, and includes:
a) preventing a disease-state associated with p16 activity from occurring;
b) inhibiting a disease-state associated with p16 activity, i.e., arresting its development; or
c) relieving a disease-state associated with p16 activity, i.e., causing regression of the condition.

The term "transcription activation domain" is used herein refers to a protein, or protein domain with the capacity to enhance transcription of a structural sequence in-trans. The ability to enhance transcription may affect the inducible transcription of a gene, or may effect the basal level transcription of a gene, or both. For example, a reporter polynucleotide may comprise a minimal-promoter driving transcription of a sequence encoding a reporter gene. Such a reporter polypeptide may be transferred to a cell line for use in the creation of a modified host cell. Cloned sequences that silence expression of the reporter gene in cells cultured in the presence of an agonist also may be included (e.g., to reduce basal transcription and ensure detectable inducibility). Numerous other specific examples of transcription regulatory elements, such as specific minimal promoters and response elements are known to those of skill in the art and may be selected for use in the methods and polynucleotide constructs of the invention on the basis of the practitioner's desired application. Literature sources and published patent documents, as well as GenBank and other sequence information data sources can be consulted by those of skill in the art in selecting suitable transcription regulatory elements and other structural and functional sequences for use in the invention. Where necessary, a transcription regulatory element may be constructed by synthesis (and ligation, if necessary) of oligonucleotides made on the basis of available sequence information (e.g., GenBank sequences for a UAS, response element, minimal promoter etc).

Unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As used herein, the term "transcriptional regulatory sequence" refers to a polynucleotide sequence or a polynucleotide segment which, when placed in operable linkage to a transcribable polynucleotide sequence, can produce transcriptional modulation of the operably linked transcribable polynucleotide sequence. A positive transcriptional regulatory element is a DNA sequence which activates transcription alone or in combination with one or more other DNA sequences. Typically, transcriptional regulatory sequences comprise a promoter, or minimal promoter and frequently a response element, and may include other positive and/or negative response elements as are known in the art or as can be readily identified by conventional transcription activity analysis (e.g., with "promoter trap" vectors, transcription rate assays, and the like). Often, transcriptional regulatory sequences include a promoter and a transcription factor recognition site and/or response elements. The term often refers to a DNA sequence comprising a functional promoter and any associated transcription elements (e.g., enhancer, CCAAT box, TATA box, SP1 site, etc.) that are essential for transcription of a polynucleotide sequence that is operably linked to the transcription regulatory region. Enhancers and promoters include, but are not limited to, herpes simplex thymidine kinase promoter, cytomegalovirus (CMV) promoter/enhancer, SV40 promoters, pga promoter, regulatable promoters and systems (e.g., metallothionein promoter, the ecdysone promoter, the Tet on/Tet-off system, the PIP on/PIP off system, etc) adenovirus late promoter, vacinia virus 7.5 K promoter, and the like, as well as any permutations and variations thereof.

Since the list of technical and scientific terms cannot be all encompassing, any undefined terms shall be construed to have the same meaning as is commonly understood by one of skill in the art to which this invention belongs. Reference to a "restriction enzyme" or a "high fidelity enzyme" may include mixtures of such enzymes and any other enzymes fitting the stated criteria, or reference to the method includes reference to one or more methods for obtaining cDNA sequences which will be known to those skilled in the art or will become known to them upon reading this specification.

Discovery—Cloning and Characterization of a Novel Peptide

The present invention relates to the cloning and characterization of a novel peptide, termed p16. The present invention also relates to the identification of amino acid sequences and nucleotide sequences comprising p16 and variants thereof (hereinafter "p16"). The present invention also relates to the determination that p16 is involved in the activation of NMDA receptors. The invention provides molecules and methods for screening candidate compounds to discover modulators of p16, NMDAR, NR3A and other proteins involved in the regulation of p16 mediates cation efflux in NMDAR. The invention provides molecules and methods that can be used to prevent or ameliorate conditions in which inappropriate NMDA receptor activation, or inappropriate responses to glycine or glutamate, are involved. The invention also provides molecules and methods used to diagnose conditions related to the dysregulation of p16 mediated cation efflux in NMDAR.

NR3A represents a dominant-interfering subunit of the conventional NMDA receptors (Das et al., Nature 393:377). NR3A expression is developmentally regulated, with its peak expression occurring during the first two weeks after birth. NR3A expression persists into adulthood at low levels in restricted areas of the brain. Neurons in NR3A knockout mice manifest increased NMDA-induced currents. Therefore, these mice allow Inventors to identify signal transduction pathways downstream to NMDAR hyperactivation. To this end, Inventors searched for genes having altered expression in NR3A-deficient brains. Inventors' selected to search using gene microarrays. Gene chips were obtained from the Ontario Cancer Center for microarray analysis between the NR3A knockout cells and wildtype cells (WT). mRNAs were extracted from WT and NR3A-KO brains at postnatal day 15, and genes that displayed different levels of expression between the two samples were identified. Inventors confirmed differential expression of these candidate genes using real-time PCR and in situ hybridization. One gene that was identified in this manner encodes an ORF of 150 amino acids, representing a protein with a predicted MW of 16 kD. The gene has the following sequence (SEQ ID No.: 1):

```
   1 ggcttggatc ccagagccca gcctgggagg aaccggggct cctggtgtac catcatcatc
  61 cccaacactc ctgttcagaa gatgggtgag gaaagtggaa agtctaacca gtcagccgat
 121 gaccagtggg aaaaatgagc tacaagatca cctgatcttc atcagtgaga aagctttgca
 181 caagagggtc tgctagaaat acttcaaccc aaaattccaa aatgaccaag aagagatcaa
 241 aaataaatga actagaagaa ctgaaattgg atatgaggaa gatcagcaat gacatggagg
 301 aaatgtgtgg aatcctgaac ctttacatgt atgaggattt gaactacagg atgaacactg
 361 aattcaacat cattaaatca caacatgaga agacaatgtt ggatatgaat aaaatgatcc
 421 agtccataat tggttccatg cagtactcca aggaactgat agaagataac tattcctaca
 481 gcattaagga ggaccacctc ctccgtgagt gcactcaact caacgaaaac gtaaggatat
 541 tactgaatga gaacagaagg ctgctggtgg agcaggctgg ccataagtgt cctgtgggga
 601 agaaaagagg ttctgtgagg aggccagcaa gaacatctgt gtcccaagtg ccaaggaaca
 661 gcagtgtgat atagtccagc agaaagcaga acatggcaca gaccacgaca tgatctccct
 721 caaagagaag tgctggagga agagcactga gtgtgcacag gaaatacacc actgttgcct
 781 ctcatcccta ataaccatgg ctgtaatggg ctgtatgctc ctctttatt ttgtttcttt
 841 ggtatgaaca ggccttaatt tcatctagcc tctggcccag gaagagtgca catttaaagg
 901 gactcagaga aatgctgaga cacatcaaga gctgctgggc atccaggaag attctgagag
 961 tttatattta tcttttcctg atgggtcatc atcaataatt acatggagat cagtcaacaa
1021 aattgtaaaa ccttggatcc aagtctacaa catgtgttct gctttgactt gggaggccat
1081 atccttcaga cccacactcc aaaaggagag tgttgcttaa atttctcctg caaagtttgt
1141 tacctccagg aactactttt ctactaagtt gccaaggaca gccacaggct gtaagtctgt
1201 gctacaaaat gagcagacta agaattttgc tttgcacaat ttttgtggtt tgattttggt
1261 ttgagttttg attagtttag ttatttgttt tttcttgttt tcattcaaag ttttgttatt
1321 tattggttat ttattgttct tttaattaat ttgatatttt gataaggtta tacacagtac
1381 atattgactg tcagctttca gttacaattg agtacattgc attttttctt atgactaaca
1441 cagtgatctc caactcttca ctctaagagc cttgttattt cagttgtgat catgaaatcc
1501 cacagatatc agacccagat ggatctctgc actcttcatg ggacttgggc tccatagttt
1561 cttctgagcc ggacttaact acaaagtcct tcatacattc agtatggaga gtttttctaa
```

```
-continued
1621 ctgtctgtat aggaacttaa tgatggaaaa cttacccatg ctgcatcgtt gctgtcaaat 1681 atttagctac tgtgaaaatc ctgtggatta tggtgttgaa cgcattaatg gcaaatacat 1741 cagtatttct gtaatagctc tcattaaatc aaagcatagt ctaagggaat aaaaagctgt 1801 cagaaaacac agcagtgtat gcttctgcgt tccttcaaat atacaatcac tggtaattgc 1861 aagtggtttc tgtgggggtc cttcaatgtt cattttatta ctttatgatt cacctgtgtc 1921 tgccaaaaaa catcactcaa aaacaatgaa gattgtaatt aggtatcatc ctataaaatc 1981 ctaacaaatg cc
```

The ORF within SEQ ID No.: 1 has the following sequence (SEQ ID No.: 2):

ATGACCAAGAAGAGATCAAAAATAAATGAACTAGAAGAACTGAAATTGG

ATATGAGGAAGATCAGCAATGACATGGAGGAAATGTGTGGAATCCTGAAC

CTTTACATGTATGAGGATTTGAACTACAGGATGAACACTGAATTCAACAT

CATTAAATCACAACATGAGAAGACAATGTTGGATATGAATAAAATGATCC

AGTCCATAATTGGTTCCATGCAGTACTCCAAGGAACTGATAGAAGATAAC

TATTCCTACAGCATTAAGGAGGACCACCTCCTCCGTGAGTGCACTCAACT

CAACGAAAACGTAAGGATATTACTGAATGAGAACAGAAGGCTGCTGGTGG

AGCAGGCTGGCCATAAGTGTCCTGTGGGGAAGAAAAGAGGTTCTGTGAGG

AGGCCAGCAAGAACATCTGTGTCCCAAGTGCCAAGGAACAGCAGTGTGAT

ATAG

The amino acid sequence of the p16 protein corresponding to SEQ ID No.: 2 is as follows (SEQ ID No.: 3):

MTKKRSKINELEELKLDMRKISNDMEEMCGILNLYMYEDLNYRMNTEFNI

IKSQHEKTMLDMNKMIQSIIGSMQYSKELIEDNYSYSIKEDHLLRECTQL

NENVRILLNENRRLLVEQAGHKCPVGKKRGSVRRPARTSVSQVPRNSSVI

This gene, ORF and protein were tentatively designated p16; however, as is discussed below, because the discovered variants of this protein do not necessarily share the 16 kD molecular weight with SEQ ID No.: 3, Inventors have selected the more suitable name for the genes, ORFs and proteins of the current discovery: "Takusan". Nonetheless, for this disclosure the term p16 will be used herein to refer to the discovered genes, ORFs and proteins regardless of whether the molecular weight of a protein species is actually 16 kD.

The Inventors of the current application have discovered that the overexpression of p16 in cells having NMDA receptors (NMDAR) causes hyper-excitation of these cells and an increased efflux of cations through the associated ligand gated cation channel. The overexpression of endogenous p16 was further found to localize to the same areas of the brain where expression of the NMDAR subunit NR3A normally occurs, and p16 expression is up-regulated in NR3A-KO brains. Thus, the up-regulation of p16 occurred in brain areas where NR3A expression is usually observed. These areas included the hippocampus, layer V of the cerebral cortex, and the amygdala. The fact that p16 mRNA is up-regulated in NR3A-KO brains is consistent with the notion that p16 plays a role in the positive-feedback loop that allows sustained activation of NMDARs. Thus, Inventors have discovered a novel molecular pathway allowing for the diagnosis and treatment of NMDAR dysregulation and further providing a method of screening for agents that modulate NMDAR excitation.

Inventors have overexpressed exogenous p16 in cultured cortical and hippocampal neurons. In the transfected neurons, it is observed that p16 protein localizes at synapses, and results in an increase in NMDA- but not AMPA- or GABA-induced currents.

Low density primary hippocampal cultures were prepared from newborn rats, and maintained in cell culture for 1-3 weeks. Hippocampi were enzymatically (papain, Worthington Biochemical Corporation (Lakewood, N.J.) Catalogue #3126) and mechanically dissociated into a single cell suspension, and plated onto glass coverslips coated with collagen/poly-D-lysine. Cells were then transfected with pSFV1-EGFP (control) or pSFV1/p16-EGFP (fusion protein between p16 and EGFP). Transfected cells were identified by fluorescence under microscopy. The vector pSFV1 is available from Invitrogen, Corp. (Carlsbad, Calif.) as catalogue no. 18488-019. The procedure to create pSFV1/p16-EGFP or pSFV1/EGFP is as follows: (1) the cDNA fragment corresponding to the coding region of p16 was subcloned into pEGFP-C3 (BD Biosciences Clontech, La Jolla, Calif., catalogue no.: 6082-1) at Xho I/BamH I cloning sites. The resulting construct encodes the EGFP coding region fused at the N-terminal of p16 in frame; (2) the pEGFP-C3/EGFP-p16 was then digested with Nhe I and BamH I, which released a fragment encoding EGFP-p16 fusion protein. The cohesive ends of the fragment were blunted by the Klenow fragment of E.coli DNA polymerase I and then cloned into the Sma I site of the pSFV1 vector. The resulting plasmid is named pSFV1/p16-EGFP. pSFV1/EGFP was constructed by the same method without EGFP fused to p16.

For HEK293 cells, recombinant NR1/NR2A subunits were co-transfected with pSFV1/EGFP, or pSFV1/p16-EGFP. Whole cell recordings were made 18-25 hours after the transfection. NR1 and NR2A subunits were inserted into pCDNA 1.1/Amp from Invitrogen (Carlsbad, Calif.). Catalogue number is V46020.

Whole cell recording of NMDA, AMPA, and GABA currents were made from cultured hippocampal neurons (DIV 8-10), 19 to 27 hours after being transfected with pSFV1/EGFP, or pSFV1/p16-EGFP. The patch pipettes (4-6 M.ohm.) were filled with an internal solution consisting of (in mM): 140 potassium gluconate, 17.5 KCl, 9 NaCl, 1 $MgCl_2$, 10 Hepes, and 0.2 EGTA, at pH 7.4. The standard external solution contained 150 mM NaCl, 3 mM KCl, 10 mM Hepes, 5 mM glucose, 2 mM $CaCl_2$, and 1 μM TTX. To isolate NMDA currents, 10 .micro.M CNQX (chemical name: 6-cyano-7-nitroquinoxaline-2,3-dione; which is available from numerous vendors, including A.G. Scientific, Inc., San Diego, Calif. 92121 as catalogue number C1053), 10

µM glycine, and 10 µM biccuculine were added to the solution. To isolate AMPA currents, 50 µM APV and 10 µM biccuculine were added to the solution. To isolate GABA currents, 10 µM CNQX and 50 µM APV were added to the solution. NMDA (100 µM), AMPA (10 µM), or GABA (100 µM) were applied every 15 seconds at a holding potential of −75 mV.

Solution exchange was made with computer controlled gravity-fed flow tubes, which is essentially comprised of a computer controlled, valve controller (Warner Instrument Co, Hamden Conn., VC-6) controlling 3-way valves (The Lee Co, Essex, Conn., LFAA1203618H). The flow tube is from Polymicro Technologies, Phoenix, Ariz., 2000625). Data acquisition and analysis were made with PClamp 8 (Axon Instruments, Union City, Calif.). Currents were normalized to cell capacitance. Results are expressed as mean±SEM in FIGS. 1a-c. All experiments were performed at room temperature.

Expression of the p16 protein enhances NMDA currents in cultured hippocampal neurons. Representative NMDA, AMPA, and GABA currents from a control neuron (EGFP) and a neuron containing p16 (p16-EGFP) are shown in FIGS. 1a and 1b. The straight, horizontal line in both FIG. 1a and FIG. 1b indicates the duration of agonist applications. Traces are averages of 4-5 responses. In FIGS. 1a and 1b, the tracing that remains the uppermost tracing during the duration of agonist application represents AMPA, the middle tracing during the duration of agonist application represents NMDA, and the lowermost tracing during the duration of agonist application represent GABA. FIG. 1c shows that NMDA current density, measured in pA/pF, in p16-EGFP neurons (n=10) was significantly larger than that of control neurons having EGFP only (n=10, $p<0.05$). In contrast, AMPA and GABA currents were not altered by p16 transfection.

Figure 2:
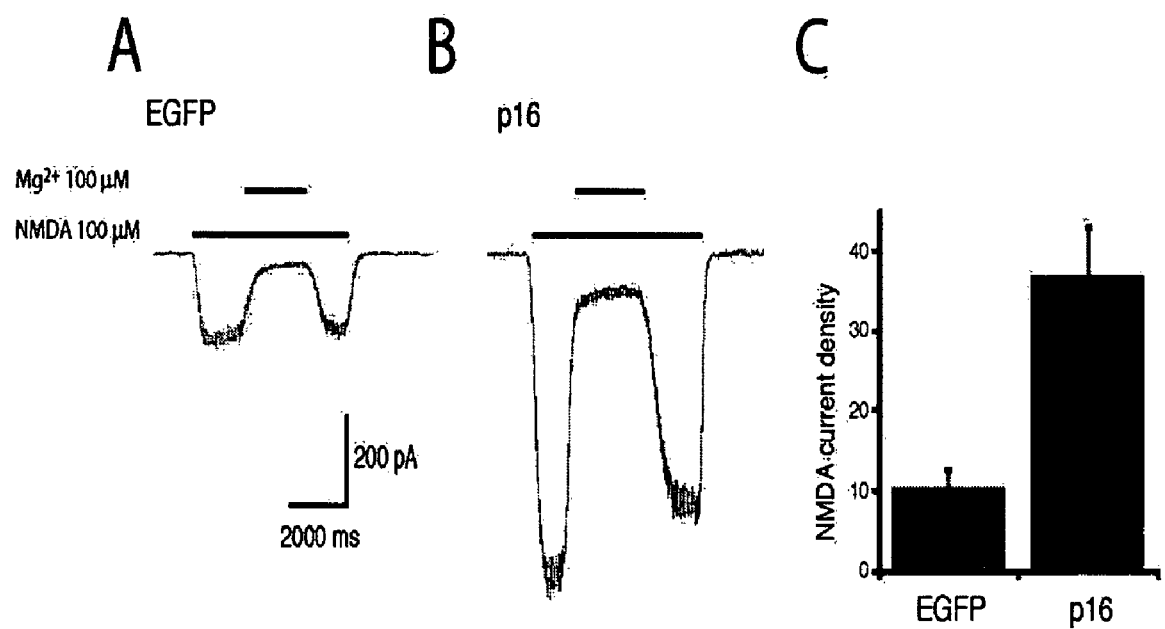
FIGS. 2a, 2b and 2c show that expression of p16 enhances recombinant NR1/NR2A currents in HEK293 cells.

FIG. 2. Expression of p16 enhances recombinant NR1/NR2A currents in HEK293 cells. Representative NMDA currents from a HEK293 cell containing EGFP (FIG. 2a) or p16-EGFP (FIG. 2b) are shown. NMDA current density in cells containing p16-EGFP (n=7) was significantly larger than that of cells containing on EGFP (n=8, $p<0.01$) (FIG. 2c).

Electrophysiological methods for detecting monovalent cation currents through an NMDA receptor are well known in the art. Exemplary methods for recording whole-cell and single-channel currents in *Xenopus oocytes*, brain slices, mammalian cells and cell-free membrane patches are described in Das et al., Nature 393:377-381 (1998); Sakmann and Neher, in Single-Channel Recording, 2nd ed., Ch. 15, pp. 341-355, (1995), edited by Bert Sakmann and Erwin Neher, Plenum Press, New York; Penner, in Single-Channel Recording, 2nd ed., Ch. 1, pp. 3-28; Hamill et al., Pflugers Arch. 391:85-100 (1981); Ilers et al., in Single-Channel Recording, 2nd ed., Ch. 9, pp. 213-229, (1995), edited by Bert Sakmann and Erwin Neher, Plenum Press, New York.

Ionic currents can also be detected using suitable detectably labeled ion indicators. Ion indicators and methods for their use are known in the art. For example, monovalent cation currents through the NMDA receptor can be detected using $Na^+$ or $K^+$ ion indicators, which can be fluorescently labeled or radiolabeled (see, for example, Moore et al., Proc. Natl. Acad. Sci. USA 90:8058-8062 (1993); Paucek et al., J. Biol. Chem. 267:26062-26069 (1992); Xu et al., J. Biol. Chem. 270: 19606-19612 (1995)). Exemplary ion indicators include: SBFI sodium indicator, Sodium Green sodium indicator; CoroNa Red sodium indicator; PBFI potassium indicator; 6-Methoxy-N-(3-sulfopropyl)quinolinium (SPQ) chloride indicator; N-(Ethoxycarbonylmethyl)-6-methoxyquinolinium bromide (MQAE) chloride indicator; 6-Methoxy-N-ethylquinolinium iodide (MEQ) chloride indicator; Lucigenin chloride indicator, which are available from Molecular Probes, Inc.

Subsequent to NMDA receptor activation and membrane depolarization, an influx of $Ca^{2+}$ ions occurs if voltage-dependent $Ca^{2+}$ channels are present in the cell being studied. If the cell of interest does not endogenously express voltage-dependent $Ca^{2+}$ channels, the cell can be recombinantly engineered to express such channels, using voltage-dependent $Ca^{2+}$ channel subunit gene sequences and molecular biology methods known in the art. Accordingly, ionic currents through the NMDA receptor can also be detected, indirectly, using detectably labeled $Ca^{2+}$ ion indicators, which can be fluorescently labeled or radiolabeled. Exemplary $Ca^{2+}$ ion indicators include FLUO-3 AM, FLUO-4 AM, FURA-2, INDO-1, FURA RED, CALCIUM GREEN, CALCIUM ORANGE, CALCIUM CRIMSON, BTC, and OREGON GREEN BAPTA (see, for example, Grynkiewitz et al., J. Biol. Chem. 260:3440-3450 (1985); Sullivan et al., in Calcium Signal Protocol, Methods in Molecular Biology 114: 125-133, Edited by David G. Lambert, Human Press, Totowa, N.J. (1999); Miyawaki et al., Proc. Natl. Acad. Sci. USA 96:2135-2140 (1999); and Coward et al., Analyt. Biochem. 270:242-248 (1999)).

Figure 3:
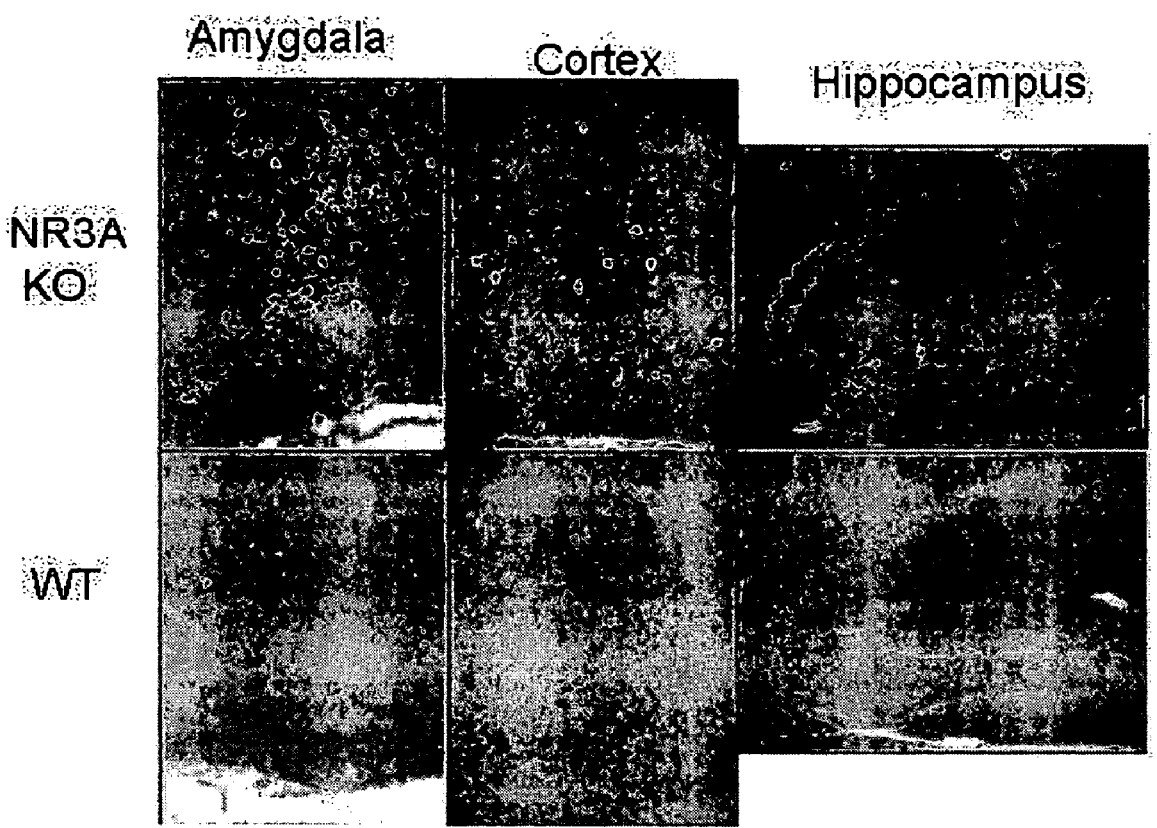
FIG. 3 shows that p16 expression is upregulated in NR3A knockout mice as compared to wild type using a p16 probe for in-situ hybridization.

FIG. 3 shows that p16 expression is upregulated in NR3A knockout mice. In this example, p16 was used as a hybridization probe to perform an in-situ hybridization. An anti sense RNA probe was used for this in-situ hybridization. The probe sequence (SEQ ID No. 84) was produced from pCRII-TOPO included in TOPO-TA cloning kits (Invitrogen, Carlsbad, Calif., Catalogue # KNM4500-40z). The difference in RNA levels between NR3A KO and WT was visually compared on the pictures taken from the brain tissue sections performed with in situ hybridization. The experiments for both NR3A KO and WT were performed under same conditions and at the same time. The pictures were taken under same exposusre conditions. Inventors have identified p16 as a gene whose expression is higher in NR3A knockout mice than WT mice using DNA microarray. The data shown here in FIG. 3 confirms that p16 expression is upregulated in the amygdala, cerebral cortex and hippocampus of NR3A KO mice compared to the NR3A wild type. These three areas (amygdala, cerebral cortex and hippocampus) are where NR3A expression normally occurs for WT mice.

Inventors' discovery of this novel genes, ORF and protein in the NMDAR molecular pathway presents a variety of uses, including, but not limited to: diagnosing the cause of disorders associated with NMDAR function; treating disorders associated with NMDAR function; and screening for novel agents that modulate the function of p16.

Screening of Complete Mouse Genome for p16 Loci

Inventors then examined the completed mouse genome sequence to identify sequences related to p16. Using the coding region (SEQ ID No.: 2) of the discovered p16 DNA sequence (SEQ ID No.: 1) as a query for BLASTN against the mouse genome found at the National Center for Biotechnology Information (www.ncbi.nlm.nih.gov), Inventors discovered 40-60 different loci encoding putative proteins that are highly homologous to p16. Furthermore, a search of Genbank reveals multiple sequences highly related to p16. Some of these sequences are putative transcription units based on the genome sequence. Others are cDNAs isolated by the FANTOM Consortium and the RIKEN Genome Exploration Research. These cDNAs were isolated from embryonic whole body and various organs such as testis, ovary, uterus, mammary tumors and spinal cord. None of the cDNAs had been assigned functions prior to Inventors' current work.

To determine if any of these p16-related sequences are expressed in the mouse brain, RT-PCR was performed using whole brain of a wild-type C57BL6/J mouse (male, 6 week old). Briefly, total RNA was isolated from the mouse brain using RNA STAT-60 for the RNA extraction (TEL-TEST, INC., Friendswood, Tex.; Catalogue #CS-110) and using RNeasy midi kit for RNA purification (Qiagen, Hilden, Germany; Catalogue #75144). cDNAs were synthesized using Superscript II RNase H.sup.—Reverse Transcriptase (Invitrogen Life Technologies, Carlsbad, Calif., catalogue no.: 18064-022), and PCR was performed using PfuUltra High Fidelity DNA Polymerase (Stratagene, Inc., La Jolla, Calif., catalogue no.: 600384). In order to amplify p16 and its related proteins, primer sequences were designed against the untranslated regions of the genomic and cDNA sequences that were deposited in Genbank. Four different 5' primers and one common 3' primer were used to set up four different PCR reactions. These four PCR reactions were further amplified using nested primers, again having four different 5' primers and one common 3' primer. Thus, reaction 1 used 5' primer CATCCCCAACACTCCTGTTC (SEQ ID No.: 72) and 3' primer GAGGAGCATACAGCCCATTAC (SEQ ID No.: 73), followed by 5' nested primer CTAGCTAGCAAGATGGGT-GAGGAAAGTGG (SEQ ID No.: 74) and 3' nested primer CCGCTCGAGTGCACACTCAGTGCTCTTCC (SEQ ID No.: 75). Reaction 2 used 5' primer CAGCTGGAAGAT-AGCTTTTCTG (SEQ ID No.: 76) and 3' primer SEQ ID No.: 73, followed by 5' nested primer CTAGCTAGCTCCCTC-CATCTTCTTCTTGG (SEQ ID No.: 77) and 3' nested primer SEQ ID No.: 75. Reaction 3 used 5' primer CCCCT-CAAAAGCACATGAC (SEQ ID No.: 78) and 3' primer SEQ ID No.: 73, followed by 5' nested primer CTAGCTAGC-GAAGGAGAGGTTGCCAAAGG (SEQ ID No.: 79) and 3' nested primer SEQ ID No.: 75. Reaction 4 used 5' primer ACTCGTCTCGCCACATGAAC (SEQ ID No.: 80) and 3' primer SEQ ID No.: 73, followed by 5' nested primer CTAGCTAGCTTCACAGAGATGTGAGATGGAG (SEQ ID No.: 81) and 3' nested primer SEQ ID No. 75.

In order to minimize the occurrence of mutations during the PCR, a DNA polymerase with proof-reading ability (PfuUltra—Stratagene, Inc.) was used and the number of PCR cycles was reduced. In addition, several lines of evidence suggest that most of these variations are authentic and were not introduced by PCR. First, variations occur at certain positions of the PCR products. Second, variations are reproducible from one PCR reaction to another. Third, most of these variations are present in genomic and Riken cDNA sequences that have been deposited to Genbank.

PCR products were cloned into pcDNA3.1/myc-His (Invitrogen, Corp., Carlsbad, Calif., catalogue number V855-20) and the DNA sequences of the cloned products were determined for both strands using a capillary ABI 3730 sequencer. DNA sequences were determined for 90 cDNA clones, 34 of which encoded different nucleotide sequences in their coding regions. All 34 deduced amino acid sequences are substantially similar to the amino acid sequence of SEQ ID No.: 3. These amino-acid sequences are presented in FIG. 4a, and are listed in the Sequence Listing below as Sequence ID Nos.: 4-37. In this FIG. 4a, the clone identification numbers are listed at the left, the sizes (number of amino acids) of the proteins are at the right. Note that the prototypical p16 starts at the position 56 in this alignment. In other words, there are multiple variants that contain as many as 55 amino acids at the N-termini. As mentioned above, there are 40-60 multiple loci encoding p16 and its related proteins in the mouse genome.

Therefore, the multiplicity of these loci is likely a major contributor of the variations among p16 and its related proteins. Another likely source of the variations is alternative splicing, although it appears this occurs frequently via the usage of different acceptors (intronic GT sequences) from a single exon. As a result of these variations, the encoded p16 proteins differ in the following fashions: (1) at the N-terminal, the presence or absence of termination codons at the 5'-UTR creates variations in the starting ATG position; (2) multiple single amino-acid changes are present in the middle of the sequences, although many are conservative and may not alter protein functions; and (3) c-terminals vary in multiple forms, for example, many forms contain -SVI at the C-terminus, which is a motif that is likely to bind to a class I PDZ domain, while other forms contain C-terminal sequences (such as -SVK) that are unlikely to bind to a PDZ domain.

PDZ domains are regions of sequence homology found in diverse signaling proteins (Cho, K. O. et al. (1992) Neuron 9:929-942; Woods, D. F. and Bryant, P. J. (1993), Mech Dev 44:889, Kim, E. et al. (1995) Nature 378:85-88). The name "PDZ" derives from the first three proteins in which these domains were identified: PSD-95, a protein involved in signaling at the post-synaptic density; DLG, the *Drosophila* Discs Large protein; and ZO-1, the zonula occludens 1 protein. PDZ domains are also sometimes called DH domains or GLGF repeats.

These hypotheses were tested, and it has been determined that, indeed, some p16 variants bind to a PDZ-containing protein, while other variants do not (see discussion below).

FIG. 4b shows the nucleotide sequences for the clones shown in FIG. 4a. Again, the clone identification is on the left; however, the number of nucleic acid residues is along the top. In FIG. 4b, the nucleotide sequences are again aligned for comparison. The nucleotide sequences are also listed in the Sequence Listing below as Sequence ID Nos.: 38-71.

Figure 5:
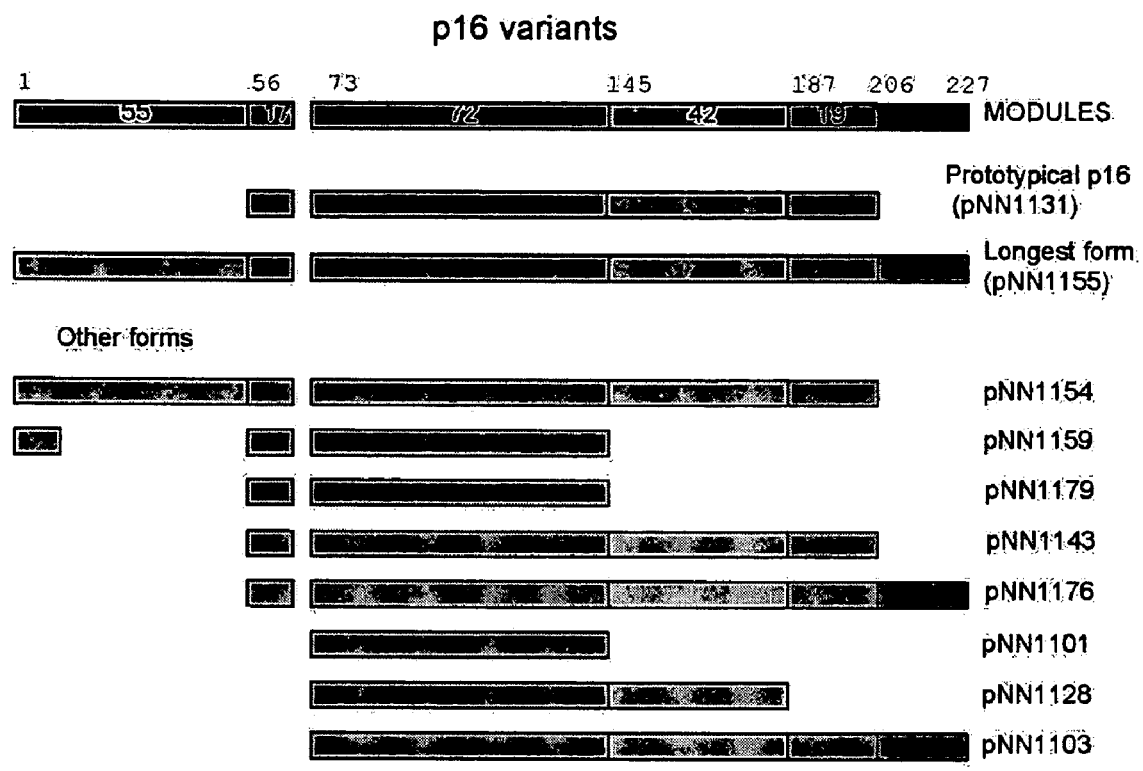
FIG. 5 is a schematic representation of many of the p16 variants identified in the current invention.

FIG. 5 is a schematic representation of many of the p16 variants identified in the current invention. The various forms of p16 are shown in modular form, having one or more of six modules. The module sizes are, from n-terminus to c-terminus, 55 aa, 17 aa, 72 aa, 42 aa, 19 aa and 22 aa. The prototypical p16 protein in the C57BL/6 mouse strain is PNN1131 (SEQ ID No.: 21), which has four modules. PNN1155 (SEQ ID No.: 9) is the longest variant having all six modules. Other p16 variants are also shown having different modules, which will vary in size, shape and, thus, interactions. These additional representative p16 variants are PNN1154 (SEQ ID No.: 4), PNN1159 (SEQ ID No.: 10); PNN1179 (SEQ ID No.: 33); PNN1143 (SEQ ID No.: 19); PNN1176 (SEQ ID No.: 13); PNN1101 (SEQ ID No.: 35); PNN1128 (SEQ ID No.: 36); and PNN1103 (SEQ ID No.: 34).

Figure 6:
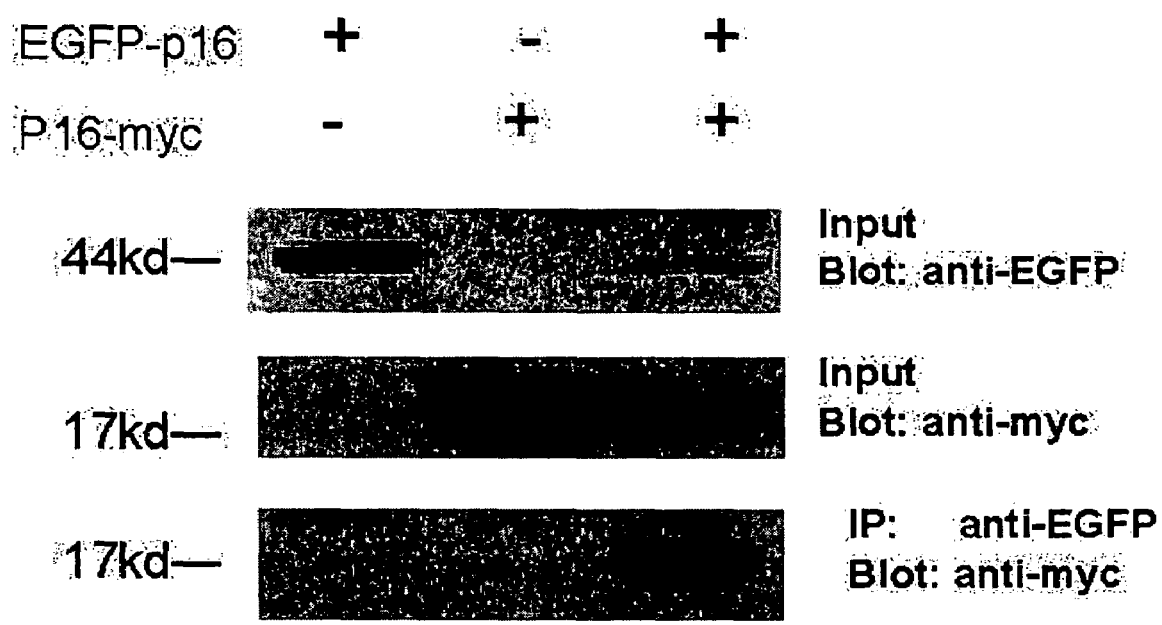
FIG. 6 is an immunoblot showing that p16 protein can dimerize in cells.

P16 is predicted to contain a coiled-coil domain, which is often used for self dimerization or oligomerization of proteins. To test if p16 dimerizes, oligomerizes or otherwise associates with a second p16 molecule, the following experiments were performed (see FIG. 6). Prototypical p16 (SEQ ID No.: 21) was tagged with either myc or EGFP. The tagged p16 proteins were transfected separately into COS-7 cells or co-transfected into COS-7 cells. The p16-myc and p16-EGFP proteins were expressed within their respective cells, and following expression, the cells were lysed. Protein lysates were precipitated and the extracts were subjected to western immunoblot using anti-EGFP or anti-myc in a two-stage antibody detection reaction. In FIG. 6, lane 1 represents COS-7 transfected with p16-EGFP, lane 2 represents COS-7 transfected with p16-myc and lane 3 represents COS-7 transfected with both p16-EGFP and p16-myc. Also in FIG. 6, the top and middle panels represent an immunoblot of the cell lysates using anti-EGFP and anti-myc, respectively. In the bottom panel, the immunoprecipitates with anti-EGFP were blotted on the membrane and probed with anti-myc.

The top and middle panels of FIG. 6 show that p16-EGFP and p16-myc are expressed in COS-7 cells. Lane 3 of the bottom panel of FIG. 6 shows that p16-myc is co-immunoprecipitated with p16-EGFP. Both p16-EGFP and p16-myc stayed in the same complex during the procedure of immunoprecipitation. Before they were subjected to SDS-PAGE for the immunoblot, they were treated with SDS and mercaptoethanol for denaturation. By probing with anti-myc antibody on this blot, the monomerized p16-myc was visualized. The fact that p16-myc is present in the fraction precipitated by anti-GFP suggests p16-myc and p16-EGFP dimerizes, oligomerizes or otherwise associate in cells.

Figure 7:
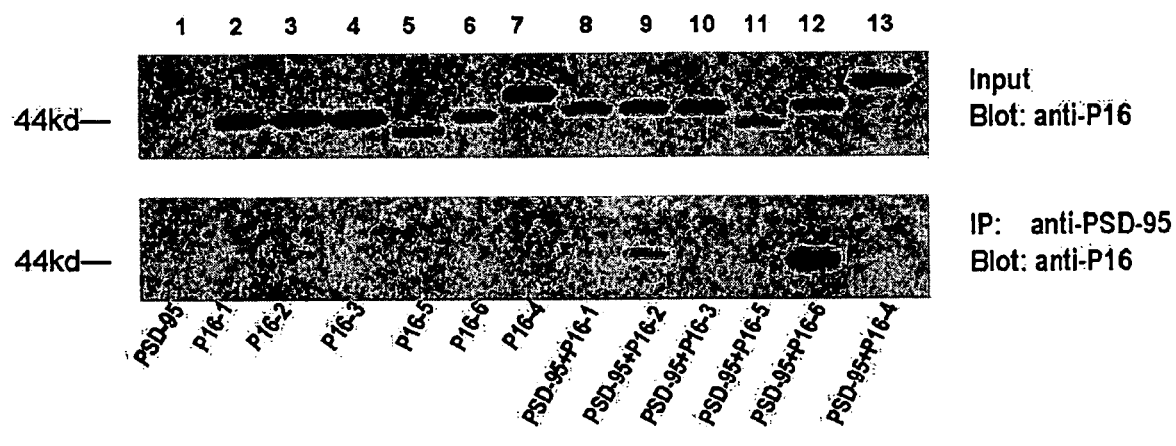
FIG. 7 is an immunoblot showing that select p16 variants can associate with PSD-95

As discussed above, some p16 variants contain C-terminal sequences that are predicted to bind a class I PDZ domain, while other variants do not. PDZ domains are contained in proteins such as PSD-95, which is known to bind and regulate NMDAR-receptor subunit 2 (NR2). In FIG. 7, the ability of p16 variants to bind PSD-95 was tested in co-immunoprecipitation experiments.

Six p16 variants were subjected to co-immunoprecipitation experiments with PSD-95. Briefly, six variants (p16-1 to p16-6) were cloned by RT-PCR as described above from NR3A KO mice whose genetic background is 129SV/J. Both DNA (SEQ ID Nos.: 85-90) and deduced-amino-acid sequences (SEQ ID Nos.: 91-96) of these clones are provided in the Sequence Listing, below. The sequences of p16 are slightly divergent from strain to strain, which is not surprising considering the unusual size of this gene family. COS-7 cells were then transfected with PDS-95 alone (lane 1 in FIG. 7), p16-EGFP variants alone (lanes 2-7 in FIG. 7), or the combination of PSD-95 and one of the p16-EGFP variants (Lanes 8-13 in FIG. 7). Based on antigenicity plots, it was determined to raise rabbit antisera against the following two peptides: N-terminal (2-20) TKKRSKINELEELKLDMRK (SEQ ID No.: 82) and C-terminal (123-141) CPVGKKRGSLRRPARTSVS (SEQ ID No.: 83). Antibodies against these peptides were predicted to recognize p16 and its structurally related proteins. The antibodies were produced by ABGENT (San Diego, Calif.). Briefly, the two peptides were synthesized and conjugated to keyhole limpet hematocyanin (KLH). Conjugated peptides were used to immunize two rabbits per peptide. Each rabbit was immunized 8 times with 100-200 mg antigen in the span of 10 weeks. Antisera against C-terminal and N-terminal peptides were named anti-p16N and p16C, respectively. These sera are useful for binding antibody against p16, which in turn is useful for a variety of purposes, including but not limited to immunoblotting and immunohistochemistry. For the immunoblot experiments presented in FIG. 7, a mixture of anti-p16N and p16C sera was used and generally termed "anti-p16". In the top panel of FIG. 7 the lysates were blotted with anti-p16 antibody in a two stage detection reaction to verify the expression of p16 in the transfected COS cells. In the lower panel of FIG. 7 the lysates were immunoprecipitated with anti PSD-95 antibody and then detected using a two stage antibody detection reaction, wherein the first stage was anti p16 and the second stage had a detectable label. Consistent with the predictions made by Scansite 2.0 program (available from Massachusetts Institute of Technology via their website at http://scansite.mit.edu/), the p16 variants that contain the C-terminal sequences such as -SVI (p16-2 (SEQ ID No.: 92)) and -VVL (p16-5 (SEQ ID No.: 95)) associate with PSD-95, while other p16 variants did not.

Figure 8:
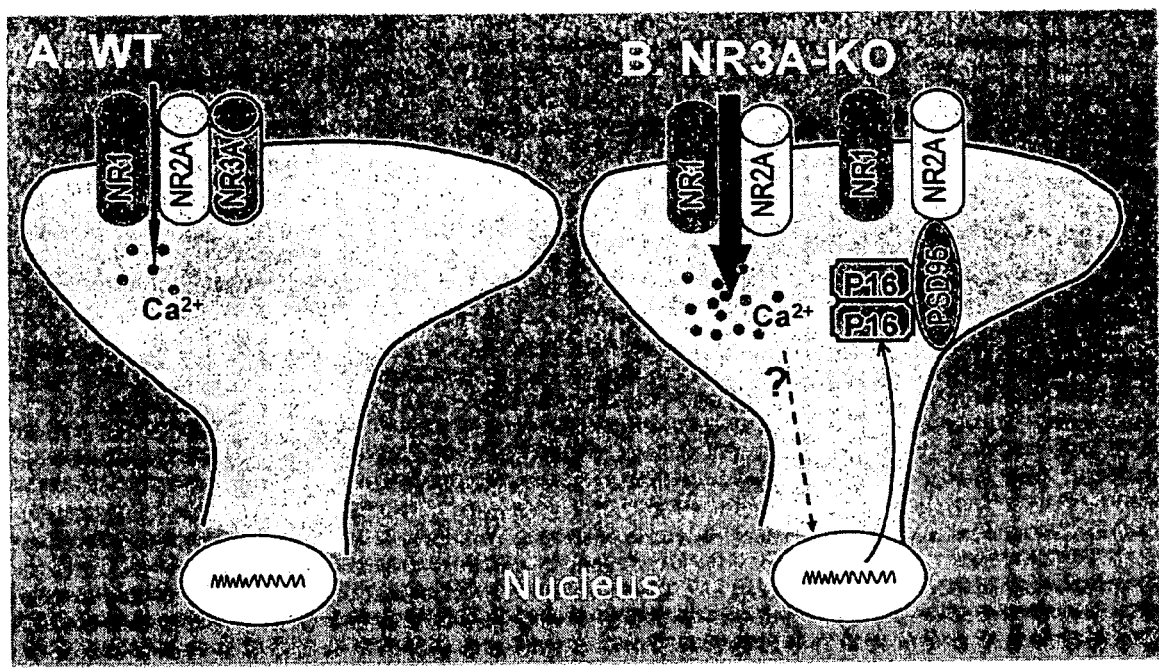
FIG. 8 is an illustration of a model for p16 function in a putative positive-feedback loop regulating NMDA receptor activity.

From these data, and without being held to any theory, Inventors have proposed the molecular mechanism presented in FIG. 8. Briefly, p16 is upregulated in NR3A KO mice. The mechanism by which NR3A KO leads to the upregulation of p16 is possibly mediated by the increased $Ca^{2+}$ permeability through the NMDA receptor. P16, in turn, dimerizes and binds to PSD-95 which is known to associate with NR2. These interactions underlie the mechanisms by which p16 upregulates NMDAR activity. The observation that p16 comes in many variant forms, some of which do not bind PSD-95 adds another layer of regulation diversity in the activity of this molecule.

Inventors have screened the human genome for a p16 homologue and have discovered that there is not a human homologue of p16. This is remarkable given the extensive expansion of p16 gene family in the rodents. It is possible that mouse and human sequences diverged quickly so that they no longer are homologous. It is also possible that p16 is unique to rodents (rats carry p16 orthologues) and mammals below human. Regardless, since NMDAR and its associated molecules such as PSD-95 are conserved between mouse and human, mouse p16 is still an effective reagent for regulating human NMDAR activity. In fact, the lack of endogenous p16 in human may account for increased efficiency of p16 in NMDAR regulation when applied to the human system, for example, through gene therapy techniques.

Endogenous p16

In the methods of the current invention, p16 can be endogenously and/or exogenously expressed in cells. Using NR3A knockout studies, endogenous expression of p16 was shown to occur in the hippocampus, in layer V of the cerebral cortex and in the amygdala. Endogenous expression of p16 can be regulated using modulators (e.g., compounds that either directly or indirectly increase or reduce the expression of p16).

Exogenous p16

Exogenous expression of p16 is accomplished using techniques well known in the art. The invention provides an isolated nucleic acid molecule that encodes a functional fragment of a p16 polypeptide. For example, using knowledge of the rat or mouse p16-encoding nucleic acid sequences and polypeptides disclosed herein, those skilled in the art can readily clone p16-encoding nucleic acids from other mammalian or vertebrate species using conventional cDNA or expression library screening methods, or using the polymerase chain reaction (PCR). Additionally, using knowledge of the rat or mouse p16-encoding nucleic acid sequences and polypeptides disclosed herein, those skilled in the art can readily determine cDNA and coding sequences from other species from an analysis of ESTs and genomic sequences present in available databases.

Interference with p16 Expression

In addition to the effects a sequence mutation may have on the expression and/or function of p16, one may use a variety of other techniques well known in the art for disrupting p16 activity on the NMDAR, including, but not limited to siRNA, anti-sense RNA and ribozymes.

a. siRNA

Small interfering RNAs (siRNAs), which are short duplex RNAs with overhanging 3' ends, directed against p16 can also be effective in preventing or reducing p16 expression. Methods of preparing and using siRNAs are known in the art and described, for example, in Elbashir et al., Nature 411:494-498 (2001).

b. Anti-sense

Antisense nucleotide sequences that are complementary to a nucleic acid molecule encoding a p16 polypeptide can be used to prevent or reduce p16 expression. Therefore, the method can be practiced with an antisense nucleic acid molecule complementary to at least a portion of the nucleotide sequence of p16. For example, the antisense nucleic acid molecule can be complementary to a region within the N-terminus of p16 such as within nucleotides 1-1000, 1-500, 1-100 or 1-18, and can optionally include sequences 5' to the start codon. Methods of preparing antisense nucleic acids molecules and using them therapeutically are known in the art and described, for example, in Galderisi et al., J. Cell Physiol. 181:251-257 (1999).

c. Ribozyme

Likewise, ribozymes that bind to and cleave p16 can also be effective in preventing or reducing p16 expression. Methods of preparing ribozymes and DNA encoding ribozymes, including hairpin and hammerhead ribozymes, and using them therapeutically are known in the art and described, for example, in Lewin et al., Trends Mol. Med. 7:221-228 (2001).

SCREENING METHODS AND EXAMPLES

Applicant's discovery of a novel pathway leading to NMDAR function is useful in a variety of methods for diagnosing and treating disorders and conditions relating to said pathway, and in screening for compounds that modulate said pathway.

The following non-limiting examples are useful in describing Applicant's discovery, and are in no way meant to limit the current invention. Those of ordinary skill in the art will readily adopt the underlying principles of applicant's discovery to design a variety of screening assays without departing from the spirit of the current invention.

Example One

A first example shows a method wherein p16 modulators are discovered. Assay methods for identifying compounds (candidate compounds) that modulate p16 activity involve comparison to a control (modulators of p16 alter its biological activity, and can include, but are not limited to those that directly bind to the p16 protein, those that affect p16 gene expression and/or translation, and those that have an indirect effect on p16). For example, identical cells, both expressing p16, are plated in two separate tissue culture wells and one well is exposed to the candidate compound, while the control well is not exposed to the candidate compound. In this situation, the response of the test cell to a candidate compound is compared to the response (or lack of response) of the control cell to the same compound under substantially the same reaction conditions.

The effect of the candidate compound on the cell lines can be measure using a variety of techniques well known in the art. In the preferred embodiment, NMDAR channel current is measured to indicate the effect of a control compound. Techniques for measuring channel current, including but not limited to that described herein above are well known in the art.

Candidate compounds shown to have an effect on the channel current of NMDAR (e.g., modulators) are useful in treating the conditions associated with NMDAR dysregulation.

Example Two

In a further assay, candidate compounds are screened for their ability to bind p16 (e.g., agonists, antagonists, ligands, etc). Assay methods for identifying compounds (candidate compounds) that bind to p16 involve comparison to a control. For example, identical cells, both expressing p16, are plated in two separate tissue culture wells and one well is exposed to the candidate compound, while the control well is not exposed to the candidate compound. In this situation, the response of the test cell to a candidate compound is compared to the response (or lack of response) of the control cell to the same compound under substantially the same reaction conditions.

The effect of the candidate compound on the cell lines can be measure using a variety of techniques well known in the art. In the current embodiment, ligand binding is measured to indicate the effect of a control compound. Techniques for measuring ligand binding, including but not limited to those described herein above are well known in the art.

Candidate compounds shown to bind p16 are useful in treating the conditions associated with NMDAR dysregulation.

Example Three

In a further example, treatments for the prevention and/or amelioration of conditions associated with inappropriate NMDAR activation, or inappropriate responses to glycine or glutamate are discussed.

Using the methods disclosed herein, it is possible to characterize and treat conditions associated with inappropriate NMDAR activation, or inappropriate responses to glycine or glutamate. For example, it is possible to isolate and sequence p16 from a sample belonging to one suffering from such conditions. It is further possible to screen for NMDA receptor subunits, including NR3A and knock-outs thereof. Nucleotide and/or protein sequence mutation are compared to the library of mutations and associated effects, described above. Alternatively, quantitative studies can be performed to uncover up or down regulation of p16 expression. Such studies are readily performed by those of skill in the art using numerous well known techniques, including but not limited to RT-PCR, Northern Blot or Western Blot. The information is then used to determine a treatment.

Depending on the results from the sequencing studies, treatment options may include: gene therapy to introduce a functional wild-type p16; or the use of p16 antagonists or agonists, (which may be small molecules, nucleic acids, such as siRNA, anti-sense RNA or the like, proteins or other discovered modulators).

Those of ordinary skill in the art will uncover a number of treatments using the above disclosed invention. Such treatments are all within the spirit of the current invention.

P16 Protein and Conditions of NMDAR:

P16 is a cytoplasmic protein that causes excitation in cells expressing NMDAR. Upregulation of p16 expression, as is observed with the NR3A knockouts is knocked out, or when NMDAR otherwise loses its biological activity, causes NMDAR bearing cells to become hyperexcited, leading to a variety of conditions. Conditions in which inappropriate NMDAR activation, or inappropriate responses to glycine or glutamate, are implicated include, for example, acute neurologic condition, such as cerebral ischemia; stroke; hypoxia; anoxia; poisoning by carbon monoxide, manganese, cyanide or domoic acid; hypoglycemia; mechanical trauma to the nervous system such as trauma to the head or spinal cord; or epileptic seizure. Other conditions include, for example, chronic neurodegenerative disease, such as Huntington's disease; a disorder of photoreceptor degeneration such as retinitis pigmentosa; acquired immunodeficiency syndrome (AIDS) dementia complex (HIV-associated dementia); a neuropathic pain syndrome such as causalgia or a painful peripheral neuropathy; olivopontocerebellar atrophy; Parkinsonism; amyotrophic lateral sclerosis; a mitochondrial abnormality or other biochemical disorder such as MELAS syndrome, MERRF, Leber's disease, Wernicke's encephalopathy, Rett syndrome, homocysteinuria, hyperhomocysteinemia, hyperprolinemia, nonketotic hyperglycinemia, hydroxybutyric aminoaciduria, sulfite oxidase deficiency, combined systems disease, lead encephalopathy, Alzheimer's disease, hepatic encephalopathy, Tourette's syndrome, drug addiction/tolerance/dependency, glaucoma, depression, anxiety, multiple sclerosis and other demyelinating disorders. Other conditions are known in the art and reviewed, for example, in Lipton et al., New Engl. J. Med. 330:613-622 (1994) and Cull-Candy et al., Curr. Opin. Neurobiol. 11:327-335 (2001). Thus, Applicant's current invention is useful in diagnosing and treating disorders and screening for modulating compounds relating to p16.

Pharmaceutical Compositions

Methods of using the compounds and pharmaceutical compositions of the invention are also provided herein. The methods involve both in vitro and in vivo uses of the compounds and pharmaceutical compositions for altering preferred nuclear receptor activity, in a cell type specific fashion.

In certain embodiments, the claimed methods involve the discovery and use of modulating compounds including agonists, antagonists, ligands and nucleic acid molecules.

Once identified as a modulator using a method of the current invention, an agent can be put in a pharmaceutically acceptable formulation, such as those described in Remington's Pharmaceutical Sciences, 18th ed., Mack Publishing Co., Easton, Pa. (1990), incorporated by reference herein, to generate a pharmaceutical composition useful for specific treatment of diseases and pathological conditions.

Agents identified by the methods taught herein can be administered to a patient either by themselves or in pharmaceutical compositions where it is mixed with suitable carriers or excipient(s). In treating a patient exhibiting a disorder of interest, a therapeutically effective amount of agent or agents such as these is administered. A therapeutically effective dose refers to that amount of the agent resulting in amelioration of symptoms or a prolongation of survival in a patient.

The agents also can be prepared as pharmaceutically acceptable salts. Examples of pharmaceutically acceptable salts include, but are not limited to acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the agent is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipients can be used to facilitate administration of the agent, for example, to increase the solubility of the agent. Examples of carriers and excipients include calcium carbonate, calcium phosphate, various sugars or types of starch, cellulose derivatives, gelatin, vegetable oils, polyethylene glycols and physiologically compatible solvents.

For applications that require the compounds and compositions to cross the blood-brain barrier, or to cross the cell membrane, formulations that increase the lipophilicity of the compound are particularly desirable. For example, the compounds of the invention can be incorporated into liposomes (Gregoriadis, Liposome Technology, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer. Additionally, the therapeutic compound can be conjugated to a peptide that facilitates cell entry, such as penetratin (also known as Antennapedia peptide), other homeodomain sequences, or the HIV protein Tat.

Toxicity and therapeutic efficacy of such agents can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents which exhibit large therapeutic indices are preferred. The data obtained from these cell culture assays and animal studies can be used in formulating a range of dosage for use in humans. The dosage of such agents lies preferably within a range of circulating concentrations that include the $ED_{50}$ with little or no toxicity. The dosage may vary within this range depending upon the dosage form employed and the route of administration utilized.

For any agent identified by the methods taught herein, the therapeutically effective dose can be estimated initially from cell culture assays. For example, a dose can be formulated in animal models to achieve a circulating plasma concentration range that includes the $IC_{50}$ as determined in cell culture (i.e., the concentration of the test agent which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g Fingl et al., in *The Pharmacological Basis of Therapeutics*, Ch. 1 p. 1 (1975)). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may also be used in veterinary medicine.

Depending on the specific conditions being treated, such agents may be formulated and administered systemically or locally. Techniques for formulation and administration may be found in *Remington's Pharmaceutical Sciences,* 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the agents herein disclosed into dosages suitable for systemic administration is contemplated. With proper choice of carrier and suitable manufacturing practice, these agents, in particular, those formulated as solutions, may be administered parenterally, such as by intravenous injection. The agents can be formulated readily using pharmaceutically acceptable carriers well known in the art into dosages suitable for oral administration. Such carriers enable the agents of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, and then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the context of the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active agents into preparations which can be used pharmaceutically. The preparations formulated for oral administration may be in the form of tablets, dragees, capsules, or solutions. The pharmaceutical compositions contemplated by the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active agents in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the agents to allow for the preparation of highly concentrated solutions.

Pharmaceutical preparations for oral use can be obtained by combining the active agents with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agent doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added.

Some methods of delivery that may be used include:
a. encapsulation in liposomes,
b. transduction by retroviral vectors,
c. localization to nuclear compartment utilizing nuclear targeting site found on most nuclear proteins,
d. transfection of cells ex vivo with subsequent reimplantation or administration of the transfected cells,
e. a DNA transporter system.

What is claimed is:

1. A method for screening compounds that modulate p16 activity, comprising:
   (a) providing an in vitro format having an NMDA receptor that is detectably capable of cation efflux;
   (b) providing at least one amino acid sequence comprising at least 95% identity to SEQ ID NO: 3 (p16);
   (c) introducing a candidate compound; and
   (d) selecting those compounds that modulate cation efflux activity of the NMDA receptor,
   wherein the in vitro format that provides the NMDA receptor that is detectably capable of cation efflux is a human cell.

2. The method of claim 1 wherein the NMDA receptor comprises all subunits.

3. The method of claim 1 wherein the NR3A subunit is knocked out.

4. The method of claim 1 wherein said compound is selected from the group consisting of a peptide, polypeptide, peptidomimetic, an antibody or antibody fragment, siRNA, anti-sense RNA, gene therapy products and a nucleotide sequence.

5. The method of claim 4 wherein said compound increases cation efflux activity of the NMDA receptor.

6. The method of claim 4 wherein said compound decreases cation efflux activity of the NMDA receptor.

7. The method of claim 1, wherein the format that provides the NMDA receptor that is detectably capable of cation efflux is a neuronal cell selected from the group consisting of amygdala cells, hippocampus cells and cerebral cortex cells.

* * * * *